(12) United States Patent
Rau et al.

(10) Patent No.: US 12,274,737 B2
(45) Date of Patent: *Apr. 15, 2025

(54) PEGYLATED RECOMBINANT HUMAN GROWTH HORMONE COMPOUNDS

(71) Applicant: Ascendis Pharma Endocrinology Division A/S, Hellerup (DK)

(72) Inventors: Harald Rau, Dossenheim (DE); Susanne Kindermann, Liestal (CH); Torben Leßmann, Neustadt an der Weinstrasse (DE); Grethe Norskov Rasmussen, Farum (DK); Ulrich Hersel, Heidelberg (DE); Thomas Wegge, Heidelberg (DE); Kennett Sprogøe, Holte (DK)

(73) Assignee: Ascendis Pharma Endocrinology Division A/S, Hellerup (DK)

( * ) Notice: Subject to any disclaimer, the term of this patent is extended or adjusted under 35 U.S.C. 154(b) by 159 days.

This patent is subject to a terminal disclaimer.

(21) Appl. No.: 17/215,991

(22) Filed: Mar. 29, 2021

(65) Prior Publication Data

US 2021/0220442 A1    Jul. 22, 2021

Related U.S. Application Data

(63) Continuation of application No. 16/146,253, filed on Sep. 28, 2018, now Pat. No. 10,960,053, which is a continuation of application No. 15/000,242, filed on Jan. 19, 2016, now Pat. No. 10,098,930, which is a continuation of application No. 12/990,101, filed as application No. PCT/EP2009/055194 on Apr. 29, 2009, now Pat. No. 9,272,048.

(30) Foreign Application Priority Data

| Apr. 29, 2008 | (EP) | ................................ 08155408 |
| Aug. 22, 2008 | (EP) | ................................ 08162865 |
| Oct. 22, 2008 | (EP) | ................................ 08167289 |

(51) Int. Cl.
| *A61K 38/27* | (2006.01) |
| *A61K 47/60* | (2017.01) |
| *A61K 47/65* | (2017.01) |
| *C07K 14/61* | (2006.01) |

(52) U.S. Cl.
CPC .............. *A61K 38/27* (2013.01); *A61K 47/60* (2017.08); *A61K 47/65* (2017.08); *C07K 14/61* (2013.01)

(58) Field of Classification Search
CPC ........ A61K 38/27; A61K 47/60; A61K 47/65; C07K 14/61; A61P 1/00; A61P 1/04; A61P 1/16; A61P 3/00; A61P 3/04; A61P 5/06; A61P 5/10; A61P 9/00; A61P 11/00; A61P 13/12; A61P 15/08; A61P 15/10; A61P 19/02; A61P 19/08; A61P 19/10; A61P 21/00; A61P 25/00; A61P 25/24; A61P 25/28; A61P 29/00; A61P 31/18; A61P 35/00; A61P 37/06; A61P 39/06; A61P 43/00

See application file for complete search history.

(56) References Cited

U.S. PATENT DOCUMENTS

| 4,179,337 | A | 12/1979 | Davis et al. |
| 5,057,417 | A | 10/1991 | Hammonds et al. |
| 5,073,627 | A | 12/1991 | Curtis et al. |
| 5,171,220 | A | 12/1992 | Morimoto |
| 5,179,080 | A | 1/1993 | Rothkopf et al. |
| 5,472,706 | A | 12/1995 | Friedman et al. |
| 5,478,925 | A | 12/1995 | Wallach et al. |
| 5,645,010 | A | 7/1997 | Lundstrom |
| 5,971,953 | A | 10/1999 | Bachynsky |
| 6,284,282 | B1 | 9/2001 | Maa et al. |
| 7,144,978 | B2 | 12/2006 | Huang et al. |
| 7,879,588 | B2 | 2/2011 | Vetter et al. |
| 7,968,085 | B2 | 6/2011 | Hersel et al. |
| 9,272,048 | B2 | 3/2016 | Rau et al. |
| 9,511,122 | B2 | 12/2016 | Rau et al. |
| 9,919,033 | B2 | 3/2018 | Rau et al. |
| 10,098,930 | B2 | 10/2018 | Rau et al. |
| 10,682,395 | B2 | 6/2020 | Rau et al. |
| 10,799,563 | B2 | 10/2020 | Rau et al. |
| 10,960,053 | B2 | 3/2021 | Rau et al. |

(Continued)

FOREIGN PATENT DOCUMENTS

| EP | 0 211 257 | 2/1987 |
| EP | 0 022 242 | 11/1992 |

(Continued)

OTHER PUBLICATIONS

Adis Insight, Drug Profile, Lonapegsomatropin, Ascendis Pharma, https://adisinsight.springer.com/print/drugs/800031668, updated (Jan. 22, 2021).

Alam et al., "Synthesis and purification of a deleted human growth hormone, hGHA135-146: sensitivity to plasmin cleavage and in vitro and in vivo bioactivities", J. of Biotechnology, 78, 49-59, 2000, Elsevier.

Antezak et al., "A New Acivicin Prodrug Designed for Tumor-Targeted Delivery", Bioorganic & Medicinal Chemistry, 9, 2843-2848, 2001, Elsevier.

Barbour et al., " Population Pharmacokinetic Modeling and Simulation of Amprenavir Following Forsamprenavir/Ritonavir Administration for Dose Optimization in HIV Infected Pediatric Patients," Pediatric Pharmacol. 54(2): 206-214, (2013).

Bowie et al., Deciphering the Message in Rotein Sequences: Tolerance to Amino Acid Substitutions: Science, 247, 1306-1310, 1990, Highwire Press.

(Continued)

*Primary Examiner* — Marcela M Cordero Garcia

(74) *Attorney, Agent, or Firm* — Alston & Bird LLP

(57) ABSTRACT

A chemically modified human Growth Hormone (rhGH) prepared by attaching a transient linker which comprises a polyethylene glycol. The chemically modified protein may have a much longer lasting rhGH activity than that of the unmodified rhGH, enabling reduced dose and scheduling opportunities and the modified rhGH may not cause lipoatrophy. Also includes methods of use for the treatment and/or prevention of diseases or disorders in which use of growth hormone is beneficial.

18 Claims, 11 Drawing Sheets

(56) References Cited

U.S. PATENT DOCUMENTS

| | | | | |
|---|---|---|---|---|
| 12,133,883 | B2* | 11/2024 | Kurpiers | A01G 2/00 |
| 2003/0171285 | A1* | 9/2003 | Finn | A61K 47/60 |
| | | | | 530/399 |
| 2006/0135427 | A1 | 6/2006 | Hays et al. | |
| 2006/0183198 | A1 | 8/2006 | Buechler et al. | |
| 2006/0257479 | A1 | 11/2006 | Jensen et al. | |
| 2006/0275252 | A1 | 12/2006 | Harris et al. | |
| 2008/0063727 | A1 | 3/2008 | Kim et al. | |
| 2008/0113914 | A1 | 5/2008 | Hays et al. | |
| 2008/0241102 | A1 | 10/2008 | Hersel et al. | |
| 2010/0197573 | A1 | 8/2010 | Dorwald et al. | |
| 2010/0291021 | A1 | 11/2010 | Vetter et al. | |
| 2011/0009315 | A1 | 1/2011 | Hersel et al. | |
| 2011/0053848 | A1 | 3/2011 | Cleemann et al. | |
| 2011/0112021 | A1 | 5/2011 | Rau et al. | |
| 2011/0172390 | A1 | 7/2011 | Vetter et al. | |
| 2011/0223230 | A1 | 9/2011 | Hersel et al. | |
| 2012/0035101 | A1 | 2/2012 | Fares et al. | |
| 2012/0058084 | A1 | 3/2012 | Rau et al. | |
| 2012/0156259 | A1 | 6/2012 | Rau et al. | |
| 2012/0156260 | A1 | 6/2012 | Rau et al. | |
| 2012/0322721 | A1 | 12/2012 | Rasmussen et al. | |
| 2017/0312342 | A1* | 11/2017 | Sprogøe | A61K 38/27 |
| 2020/0261544 | A1* | 8/2020 | Rasmussen | A61K 47/18 |
| 2020/0390864 | A1 | 12/2020 | Rau et al. | |
| 2022/0088147 | A1 | 3/2022 | Sprogoe et al. | |

FOREIGN PATENT DOCUMENTS

| | | | |
|---|---|---|---|
| EP | 0 809 996 | | 12/1997 |
| EP | 0 975 369 | | 12/2003 |
| EP | 1 196 443 | | 5/2004 |
| EP | 1 579 873 | | 9/2005 |
| EP | 1 625 855 | | 2/2006 |
| EP | 1 562 634 | | 8/2006 |
| EP | 1 715 887 | | 6/2007 |
| EP | 2 113 256 | | 11/2009 |
| EP | 2 119 726 | | 11/2009 |
| JP | H-1067800 | | 3/1998 |
| JP | 2007-515463 | | 6/2007 |
| JP | 2007-530485 | A | 11/2007 |
| RU | 2229288 | C2 | 5/2004 |
| WO | WO 1994/10308 | | 5/1994 |
| WO | WO 1999/30727 | | 6/1999 |
| WO | WO 2001/047562 | | 7/2001 |
| WO | WO 2001/78683 | | 10/2001 |
| WO | WO-02055532 | A2 * | 7/2002 ............. A61K 47/60 |
| WO | WO 2002/083180 | | 10/2002 |
| WO | WO 2002/089789 | | 11/2002 |
| WO | WO 2003/044056 | | 11/2003 |
| WO | WO 2004/043493 | | 5/2004 |
| WO | WO 2005/027978 | | 3/2005 |
| WO | WO 2005/034909 | | 4/2005 |
| WO | WO 2005/061005 | | 4/2005 |
| WO | WO 2006/084888 | | 8/2005 |
| WO | WO 2005/079838 | | 9/2005 |
| WO | WO 2005/099768 | | 10/2005 |
| WO | WO 2006/0003014 | | 1/2006 |
| WO | WO 2006/071840 | | 7/2006 |
| WO | WO 2006/076471 | | 7/2006 |
| WO | WO 2006/102659 | | 9/2006 |
| WO | WO 2006/136586 | | 12/2006 |
| WO | WO 2007/025988 | | 3/2007 |
| WO | WO 2007/075534 | A2 | 3/2007 |
| WO | WO 2007/114881 | | 10/2007 |
| WO | WO 2008/112155 | | 9/2008 |
| WO | WO 2008/155134 | | 12/2008 |
| WO | WO 2009/095479 | | 8/2009 |
| WO | WO 2009/133137 | | 11/2009 |
| WO | WO 2011/03234 | A2 | 6/2011 |
| WO | WO 2011/073234 | | 6/2011 |
| WO | WO 2011/073234 | A2 | 6/2011 |
| WO | WO 2011/123813 | | 10/2011 |
| WO | WO 2011/144756 | | 11/2011 |
| WO | WO 2014/060512 | | 4/2014 |
| WO | WO 2016/079114 | A1 | 5/2016 |
| WO | WO 2016/079302 | A1 | 5/2016 |
| WO | WO 2016/109823 | A1 | 7/2016 |
| WO | WO 2017/136583 | A1 | 8/2017 |
| WO | WO 2020/178273 | A1 | 9/2020 |
| WO | WO 2022/2077798 | A1 | 10/2022 |
| WO | WO 2004/019993 | | 3/2023 |
| WO | WO 2008/084237 | | 3/2023 |

OTHER PUBLICATIONS

Buyukgebiz et al., "Localized Lipoatrophy due to Recombinant Growth Hormone Therapy in a Child with 6.7 Kilobase Gene Deletion Isolated Growth Hormone Deficiency", J. of Pediatric Endocrinology & Metabolism, 12, 95-97, 1999, Freund Publishing House Ltd., London.

Cheng et al., "Synthesis of Linear, fl-Cyclodextrin-Based Polymers and Their Camptothecin Conjugates", Bioconjugate Chem., 14, 1007-1017, 2003, American Chemical Society.

Clark et al., "Long-acting Growth Hormones Produced by Conjugation with Polyethylene Glycol", J. Biol. Chem., 271:36, 21969-21977, Sep. 1996, American Society for Biochemistry and Molecular Biology, Inc.

Dag, et al., "Preparation of 3-Arm Star Polymers (A3) via Diels-Alder Click Reaction," Journal of Polymer Science: Part A: Polymer Chemistry, 46, 302-313, (2007).

Davis, et al., "The effect of bovine somatotroin in a sustained release preparation (Somidobove) on milk production of cows at pasture in New Zealand," New Zealand Journal of Agricultural Research, vol. 42, 315-323, (1999).

Garman et al., "The preparation and properties of novel reversible polymer-protein conjugates", FEBS Letters, 223:2, 361-365, Nov. 1987, Elsevier.

Genotropin insert, Pharmacia & Upjohn Co. LAB-0222-9.0, 2006.

Gohil, "Long-Acting Therapies Will Expand Growth Hormone Deficiency Market," Pipeline Plus vol. 40(11): 772-773, 2015.

Greenwald et al., "Drug Delivery Systems Employing 1,4- or 1,6-Elimination: Poly (ethylene glycol) Prodrugs of Amine-Containing Compounds", J. Med. Chem., 42, 3657-3667, 1999, American Chemical Society.

Grigorian et al., "Extraordinarily stable disulfide-linked homodimer of human growth hormone", Protein Sci., 14, 902-913, Mar. 1, 2005, Cold Spring Harbor Laboratory Press.

Haffner et al., "Metabolic Clearance of Recombinant Human Growth Hormone in Health and Chronic Renal Failure", J. Clin. Invest,, 93, 1163-1171, Mar. 1994, American Society for Clinical Investigation, Inc.

Hoybye, et al., "A Phase 2, Multiple-Dose, Open-Label, Parallel-Group, Active Controlled, Safety, Tolerability, Pharmacokinetic and Pharmacodynamic Study of ACP-001 in Adult Patients with Growth Hormone Deficiency (AGHD) : What's New in Diagnosis & Treatment of GH Dysfunction? (Clinical)", The Endocrine Society's 94th Annual Meeting and Expo, Jun. 23-26, 2012—Houston, Tx-, (Jun. 23, 2012), pp. OR29-4, XP055246166 [Y] 3,4,38,39, abstract only.

Kemp, et al., "Pharmacokinetic and Pharmacodynamic Characteristics of a Long-Acting Growth Hormone (GH) Preparation (Nutropin Depot) in GH-Deficient Children," The Journal of Clinical Endocrinology & Metabolism, 89(7): 3234-3240, (Jul. 2004).

Lee et al., "Drug Delivery Systems Employing 1,6-Elimination: Releasable Poly(ethylene glycol) Conjugates of Proteins", Bioconjugate Chan, 12, 163-169, 2001, American Chemical Society.

Luo et al., "A Hyaluronic Acid-Taxol Antitumor Bioconjugate Targeted to Cancer Cells", Biomacromolecules, 1, 208-218, 2000, American Chemical Society.

MacGillivray, et al., "Current Dosing of Growth Hormone in Children with Growth Hormone Deficiency: How Physiologic?," Pediatrics, 102: 527-530, (1998).

Machlin, L,J., "Effect of Porcine Growth Hormone on Growth and Carcass Composition of the Pig", J. of Animal Science, 35, 794-800, 1972, ASAS.

(56) References Cited

OTHER PUBLICATIONS

Mehta, et al., "The Use of Somatropin (Recombinant Growth Hormone) in Children of Short Stature," Pediatr Drugs, 4(1): 37-47, (2002).
Monfardini et al., "A Branched Monotnethoxypoly (Ethylene Glycol) for Protein Modification," 6 Bioconjugate Chemistry p. 62-69 (1995).
Neutropin Depot, "2.B Clean Packge Insert," FDA.gov, XP055185385, (Dec. 1999).
Nishiguchi, "What is PEG-IFN?" Strategy of New Interferon Therapy, Mebio (2002) pp. 20-23 (w/English Translation).
Nutropin Depot, Clean package insert (1999).
Palchuk et al., Weight-based Pediatric Prescribing in Ambulatory Setting, AMIA 2006, SymposiumProceedings p. 1055.
Pasut et al., "A New PEG-fl-Alanine Active Derivative for Releasable Protein Conjugation", Bioconjugate Chem., 19, 2427-2431, 2008, American Chemical Society.
Peleg-Shulman et al., "Reversible PEGylation: A Novel Technology to Release Native Interferon a2 over a Prolonged Time Period", J. Med. (hem., 47, 4897-4904, 2004, American Chemical Society.
Ranke, et al., "Derivation and Validation of a Mathematical Model for Predicting the Response to Exogenous Recombinant Human Growth Hormone (GH) in Prepubertal Children with Idiopathic GH Deficiency," The Journal of Clinical Endocrinology & Metaboliam, vol. 84, No. 4, 1174-1183, (1999).
Ron et al., "Expression of Biologically Active Recombinant Keratinocyte Growth Factor", J. of Biological Chemistry, 268:4, 2984-2988, 1993, NTH, Bethesda, Maryland.
Said et al., "Comparison on Efficacy and Safety of Three Inpatient Insulin Regimens for Management of Non-Critical Patients with Type 2 Diabetes," Pharmacol. & Pharmacy, 4: 556-565, (2013).
Sengupta et al., "An audit of primary surgical treatment for women with ovarian cancer referred to a cancer centre", British J. of Cancer, 80:3/4, 444-447, 1999, Cancer Research Campaign.
Shechter et al., "New Technologies to Prolong Life-time of Peptide and Protein Drugs In vivo", International Journal of Peptide Research and Therapeutics, 13:1-2, 105-117, Jun. 2007, Springer Science+Business Media, Inc.
Shechter et al., "Reversible PEGylation of peptide YY3-36 prolongs its inhibition of food intake in mice", FEBS Letters, 579, 2439-2444, 2005, Elsevier B.V.
Skytrofatm, Highlights of Prescribing Information, Reference ID: 4846899, revised (Aug. 2021).
Swanson, "How to Dose Acetaminophen or Ibuprofen," Seattle Mama Doc. 2011.
Testa, Chapter 8 of Hydrolysis in Drug and Prodrug Metabolism, 419-523, Aug. 1, 2003, John Wiley & Sons. Clinical Focus: 45th Annual Meeting of the ESPE, Hormone Red 2006, 65 (suppl 4) 29-34. Clinical Focus: 45th Annual Meeting of the ESPE, Hormone Red 2006, 65 (suppl 4) 115-154.
Thorner, et al., "Growth Hormone GH Receptor Blockade with a PEG-Modified GH (B2036-PEG) lowers Serum Insulin-Like Growth Factro-I but Does Not Acutely Stimulate Serum GH," The Journal of Cinical Endocrinology & Metabolism, Jun. 1999; 84-6, 2098-2103.
Veronese, "Enzymes for human therapy: surface structure modifications", Chimicaoggi, 53-56, Jan.-Feb. 1989.
Veronese, Peptide and protein PEGylation: a review of problems and solutions,: Biomaterials, 22, 405-417, (2001).
Zalipsky et al., "Thiolytically Cleavable Dithiobenzyl Urethane-Linked Polymer-Protein Conjugates as Macromolecular Prodrugs: Reversible PEGylation of Proteins", Bioconjugate Chan., 18, 1869-1878, 2007, American Chemical Society.
English Translation of International Russian Office Action issued in corresponding International Application No. 2017121203 dated Oct. 15, 2019.
English Translation of Official Action dated Mar. 4, 2014 in counterpart Japanese Patent Application No. 2011-506705.
EP 21201573 European Search Report dated Mar. 16, 2022.

PCT/EP2015/077229 International Search Report dated Feb. 6, 2016.
U.S. Appl. No. 13/515,621, Advisory Action dated Dec. 29, 2014.
U.S. Appl. No. 13/515,621, Final Office Action dated Sep. 23, 2015.
U.S. Appl. No. 13/515,621, Final Office Action dated Oct. 7, 2014.
U.S. Appl. No. 13/515,621, Non-Final Office Action dated Jan. 20, 2016.
U.S. Appl. No. 13/515,621, Non-Final Office Action dated Apr. 14, 2015.
U.S. Appl. No. 13/515,621, Non-Final Office Action dated Apr. 25, 2013.
U.S. Appl. No. 13/515,621, Requirement for Restriction/Election dated Jan. 2, 2013.
U.S. Appl. No. 15/340,595, Notice of Allowance dated Nov. 1, 2017.
U.S. Appl. No. 15/528,350, Final Office Action dated Jan. 6, 2022.
U.S. Appl. No. 15/528,350, Non-Final Office Action dated Nov. 20, 2022.
U.S. Appl. No. 15/901,350, Final Office Action dated Oct. 31, 2019.
U.S. Appl. No. 15/901,350, Non-Final Office Action dated Apr. 16, 2019.
U.S. Appl. No. 15/901,350, Notice of Allowance dated Feb. 7, 2020.
U.S. Appl. No. 16/515,621, Notice of Allowance dated Aug. 2, 2016.
U.S. Appl. No. 16/866,764, Final Office Action dated Oct. 12, 2022.
U.S. Appl. No. 16/866,764, Non-Final Office Action dated Mar. 2, 2023.
U.S. Appl. No. 17/006,589, Non-Final Office Action dated Jan. 24, 2023.
U.S. Appl. No. 17/006,589, Requirement for Restriction/Election dated Nov. 9, 2022.
WIPO Application No. PCT/2010/069710, PCT Written Opinion of the International Searching Authority dated Feb. 28, 2012.
WIPO Application No. PCT/EP2010/069710, PCT International Preliminary Report on Patentability dated Jul. 3, 2012.
WIPO Application No. PCT/EP2010/069710, PCT International Search Report dated Feb. 28, 2012.
Cleland et al., "A Novel Long-Acting Human Growth Hormone Fusion Protein (VRS-317): Enhanced In Vivo Potency and Half-Life," Journal of Pharmaceutical Sciences, vol. 101, No. 8, pp. 2744-2754, (Aug. 2012).
U.S. Appl. No. 17/310,993, Requirement for Restriction/Election dated Apr. 27, 2023.
U.S. Appl. No. 15/528,350, Final Office Action dated Apr. 27, 2023.
U.S. Appl. No. 17/006,589, Notice of Allowance dated Jul. 17, 2023.
U.S. Appl. No. 16/866,764, Final Office Action dated Aug. 2, 2023.
WIPO Application No. PCT/EP2020/055513, PCT International Search Report dated May 13, 2020.
WIPO Application No. PCT/EP2009/055194, PCT International Preliminary Report on Patentability dated Nov. 2, 2010.
WIPO Application No. PCT/EP2009/055194, PCT International Search Report dated Nov. 9, 2009.
WIPO Application No. PCT/EP2015/076813, PCT International Search Report dated Apr. 18, 2016.
WIPO Application No. PCT/EP2015/076913, PCT International Preliminary Report on Patentability dated May 23, 2017.
WIPO Application No. PCT/EP2015/077229, PCT International Preliminary Report on Patentability dated May 23, 2017.
WIPO Application No. PCT/EP2015/077229, PCT International Search Report dated Feb. 11, 2016.
Lee et al., "Targeted Enzyme-responsive Drug Carriers: Studies on the Delivery of a Combination of Drugs", Angew. Chem., 116, 1707-1710, 2004, Wiley-VCR.
Shabat et al., "Chemical Adaptor Systems", Chem. Eur. J., 10, 2626-2634, 2004, Wiley-VCH.
Tsubery et al., "Prolonging the Action of Protein and Peptide Drugs by a Novel Approach of Reversible Polyethylene Glycol Modification", J. of Biological Chemistry, 279:37, 38118-38124, Sep. 2004, American Society for Biochemistry and Molecular Biology, Inc.

(56) References Cited

OTHER PUBLICATIONS

Belikov, "Farmazevtit'cheskaya Khimia (Pharmaceutical chemistry)", Part I, Moscov "Vysshaya shkola", pp. 43-45 (1993). English translation.
Genentech Inc., Nutropin AQ0, obtained from http://www.accessdata.fda.gov/drugsatfda docs/label/2005/020522s021,0221bl.pdf, p. 1-27 (2004).
Graham, et al., "AAS, Growth Hormone, And Insulin Abuse: Psychological and Neuroendocrine Effects," 4(3) Therapeutics and Clinical Risk Management 587-597 (2008).
Greenwald et al., "Drug Delivery Systems Based on Trimethyl Lock Lactonization: Poly(ethylene glycol) Prodrugs of Amino-Containing Compounds," 43 J. Med. Chemistry 475-487 (2000).
Greenwald et al., "A New Aliphatic Amino Prodrug System for the Delivery of Small Molecules and Proteins Utilizing Novel PEG Derivatives," 47 J. Med. Chemistry 726-734 (2004).
Kumar et al., "Effect of Trehalose on Protein Structure, " 18 Protein Sc'. 24-36 (2009).
Kalia et al., "Hydrolytic Stability of Hydrazones and aames," 47 Angewandte Creme Int'l Edition 7523-7526 (2008).
Kidder et al., "Effects of Growth Hormone and Low Dose Estrogen on Bone Growth and Turnover in Long Bones of Hypophysectomized Rats," 61 Calcified Tissue Int'l 327-335 (1997).
Pfizer, Highlights of Prescribing Information, obtained from http://www.accessdataida.gov/scripts/cder/drugsatfda/index.cfm, p. 1-24 (2008).
A. Semlaty et al., Properties and Formulation of Oral Drug Delivery Systems of Protein and Peptides, 69(6) Indi'n J. Pharmaceutical Sci. 741-747 (2007).
Wang, "Lyophilixation and Development of Solid Protein Pharmaceuticals," 203 Int'l J. Pharmaceutics 1-60 (2002).
Wolf et al., "Growth Hormone and Insulin Reverse Net Whole Body and Skeletal Muscle Protein Catabolismin Cancer Patients," 216(3) Annals Surgery 280-288 (1992).
Populyarnaya medicinskaya enciklopediya, gl. Red. V. I. Pokrovskij, 4-e izd., UI. "Knigochej", 1997, str. 317 (lekarstvennye sredstva) (= Popular medical encyclopedia, chief editor V. I. Pokrovskij, fourth edition, "KNIGOCHEJ", 1997, p. 317 (drugs) English translation.
Dyson, "Khimiya sintetitcheskikh lekarstvennykh veshhestv (May's Chemistry of synthethic drugs)," Lang., Moscow: "Mir", 1964, p. 12-19, English translation.
U.S. Appl. No. 17/310,993, Non-Final Office Action mailed Sep. 26, 2023.
Cleveland Clinic, "Growth Hormone Deficiency (GHD)," https://my.clevelandclinic.org/health/diseases/23343-gorwth-hormone-deficiency-ghd, pp. 1-17, accessed Sep. 21, 2023, (2023).
Pipelinereview, "Handok-Genexine Long-Acting hGH Therapeutic "GX-H9 Receives Approval for Phase I Trial in Europe, pp. 1-2, Aug. 20, 2013, (2013).
Reiter et al., "A multicenter study of the efficacy and safety of sustained release GH in the treatment of naïve pediatric patients with GH deficency," J Clin Endocrinol Metab. 2001; 86(10):4700-6.
U.S. Appl. No. 15/528,350, Notice of Allowance mailed Oct. 27, 2023.
Miccoli et al., "Height Outcome of Recombinant Human Growth Hormone Treatment in Achondroplasia Children: A Meta-Analysis," Horm Res Paediatr, DOI: 10.1159/000446958 (Jun. 2016).
Chatelain et al., "A Randomized Phase 2 Study of Long-Acting TransCon GH vs Daily GH in Childhood GH Deficiency," J Clin Endocrinal Metab, 102(5): 1673-1682, (May 2017).
History of Changes for Study: NCT02781727, "A Phase 3 Trial of the Safety, Tolerability and Efficacy of TransCon hGH Weekly Versus Daily hGH in Children With Growth HormoneDeficiency (GHD)," ClinicalTrials.gov archive, submitted Dec. 6, 2021.
History of Changes for Study: NCT03305016, "A Safety, Tolerability and Efficacy Study of TransCon hGH in Children with Growth Hormone Deficiency," ClinicalTrials.gov archive, submitted Dec. 7, 2021.
Lal, "Perspectives on long-acting growth hormone therapy in children and adults," Arch Endocrinol Metab., 63/6, (Sep. 2019).
Pan et al., "Effect of recombinant human growth hormone on liver fat content in young adults with nonalcoholic fatty liver disease," Clinical Endocrinology., vol. {0} 94, No. {0} 2, Feb. 1, 2021 (Feb. 1, 2021), p. 183-192, Abstract only.
Takahashi et al., "Growth Hormone Reverses Nonalcoholic Steatohepatitis in a Patient With Adult Growth Hormone Deficiency," GASTROENTEROLOGY, 32:938-943, (Mar. 2007).
Takahashi, "The Role of Growth Hormone and Insulin-Like Growth Factor-I in the Liver," Int. J. Mol. Sci, 18, 1447, https://doi.org/10.3390/ijms 18071447, (2017).
Verzijl et al., "Pegbelfermin (BMS-986036): an investigational PEGylated fibroblast growth factor21 analogue for the treatment of nonalcoholic steatohepatitis," Epert Opinion on Investigational Drugs, vol. 27, No. 2, 125-133, https://doi.org/10.1080/13543784.2020.1708898 (2020).
U.S. Appl. No. 16/866,764, Non-Final Office Action mailed Feb. 14, 2024.
U.S. Appl. No. 17/006,589, Non-Final Office Action mailed Jan. 5, 2024.
U.S. Appl. No. 15/528,350, Notice of Allowance mailed Feb. 23, 2024.
WIPO Application No. PCT/EP2022/058584, PCT International Preliminary Report on Patentability mailed Oct. 3, 2023.
WIPO Application No. PCT/EP2022/058584, PCT International Search Report and Written Opinion of the International Searching Authority mailed Jun. 17, 2022.
Thornton et al., "Weekly Lonapegsomatropin in Treatment-Naïve Children With Growth Hormone Deficiency: The Phase 3 heiGHt Trial," The Journal of Clinical Endocrinology & Metabolism, vol. 106, No. 11, 3184-3195, (Jul. 2021).
U.S. Appl. No. 17/006,589, Notice of Allowance and Interview Summary mailed Jun. 20, 2024.
U.S. Appl. No. 17/310,993, Final Office Action mailed Jun. 27, 2024.

\* cited by examiner

Critical Distance = 18

PEGYLATED RECOMBINANT HUMAN GROWTH HORMONE COMPOUNDS

CROSS-REFERENCE TO RELATED APPLICATIONS

The present application is a continuation application of U.S. patent application Ser. No. 16/146,253 filed on Sep. 18, 2018, which is a continuation application of U.S. patent application Ser. No. 15/000,242 filed on Jan. 19, 2016, which is a continuation application of U.S. patent application Ser. No. 12/990,101 filed on Dec. 22, 2010, now U.S. Pat. No. 9,272,048, the disclosures of which are incorporated herein by reference in their entirety, which claims priority from PCT Patent Application No. PCT/EP2009/0565194 filed on Apr. 29, 2009, which claims priority from European Priority Application No. 08167289.1 filed on Oct. 22, 2008, European Priority Application No. 08162865.3 filed on Aug. 22, 2008, and European Priority Application No. 08155408.1 filed on Apr. 29, 2008.

FIELD OF THE INVENTION

This invention relates to a pharmaceutical composition comprising suitable pharmaceutical excipients and also comprising a clinically effective amount of a recombinant human growth hormone (rhGH) PEGylated prodrug which can be administered less frequently than available human growth hormone products and may not cause injection side lipoatrophy. The present invention also relates to such prodrugs.

BACKGROUND ART

Growth hormone (GH) is a hormone that stimulates growth and cell reproduction in humans and other animals. It is a 191-amino acid, single chain polypeptide hormone which is synthesized, stored, and secreted by the somatotroph cells within the lateral wings of the anterior pituitary gland. The hormone is also known as somatotropin when referring to growth hormone produced by recombinant DNA technology, and is abbreviated "rhGH".

Growth hormone has a variety of functions in the body, the most noticeable of which is the increase of height throughout childhood, and there are several diseases which can be treated through the therapeutic use of GH.

The effects of growth hormone deficiency vary depending on the age at which they occur. In children, growth failure and short stature are the major manifestations of GH deficiency. It can also cause sexual immaturity. In adults the effects of deficiency are more subtle, and may include deficiencies of strength, energy, and bone mass, as well as increased cardiovascular risk.

There are many causes of GH deficiency, including mutations of specific genes, congenital malformations involving the hypothalamus and/or pituitary gland, and damage to the pituitary from injury, surgery or disease.

Deficiency is treated through supplementation with external GH. All GH in current use is a biosynthetic version of human GH, manufactured by recombinant DNA technology. GH is used as replacement therapy in children and adults with GH deficiency of either childhood-onset (after completing growth phase) or adult-onset (usually as a result of an acquired pituitary tumor). In these patients, benefits have variably included reduced fat mass, increased lean mass, increased bone density, improved lipid profile, reduced cardiovascular risk factors, and improved psychosocial well-being.

Genentech Inc (US) was the first to clone rhGH and this was described in patent EP-B 22242. As of 2006, synthetic growth hormones available in the United States and Europe (and their manufacturers) included Nutropin (Genentech), Humatrope (Eli Lilly), Genotropin (Pfizer), Norditropin (Novo Nordisk), Saizen (Merck Serono), and Omnitrope (Sandoz).

Although molecular biological techniques have dramatically increased the availability of many proteins and/or polypeptides (hereinafter referred to as proteins), the therapeutic use of said proteins is often times hindered by other factors, such as short plasma half-life due to renal and receptor-mediated clearance, aggregation, proteolytic degradation, poor bioavailability and physical properties which preclude efficient formulations.

A mechanism for enhancing protein availability is by conjugation of the protein with derivatizing compounds, which include, but are not limited to, polyethylene glycol and polypropylene glycol. Some of these benefits recognized include: lowered immunogenicity and antigenicity, increased duration of action, and altered pharmacokinetic properties. [Veronese, F. M. "Enzymes for Human Therapy: Surface Structure Modifications," Chimica Oggi, 7:53-56 (1989)] (Herein reference 5).

By PEGylating rhGH, it may be possible to improve the characteristics of the molecule for medical use by increasing its in vivo half-life (hereby achieving reduced dosage or reduced frequency of dosing), improving its stability and decreasing its antigenicity or a combination thereof.

Generally, this type of modification to a molecule is well known in the art and there are numerous patents available in the patent literature, describing this concept. For example a PEGylated Erythropoietin (EPO) from Hofmann La Roche is described in EP-B 1196443 claiming a specific linker comprising PEG covalently bound to EPO, a PEGylated interferon alpha described in EP-B 975369 from the company Nektar/La Roche and another PEGylated interferon alpha in EP-B 1562634 from the company Hofmann La Roche.

In vivo clearance of rhGH is believed to occur by the following two mechanisms. The first is renal clearance where rhGH is cleared from the circulation by renal glomerular filtration. Renal clearance of rhGH is well documented and PEGylation of synthetic rhGH is therefore an obvious choice to solve this problem. Renal clearance accounts for around 25-53% of the total clearance of rhGH (Girard, J. Mehls, O J. Clin. invest. 1994 March; 93(3): 1163-1 171, reference 3 herein.) The second mechanism is hepatic clearance (liver). Hepatic GH uptake occurs by receptor-mediated endocytosis followed by lysosomal degradation.

A third mechanism is receptor mediated clearance in other tissue such as chondrocytes of the cartilage. By reducing the binding affinity of GH to the GH receptor by PEGylation, the receptor mediated clearance will be reduced.

However, there are dedicated problems with the administration of rhGH. One major disadvantage of subcutaneously administrated rhGH is the occurrence of lipoatrophy in patients receiving the treatment.

Lipoatrophy is the medical term used for localized loss of fat tissue. Subcutaneously administered rhGH formulations have displayed lipoatrophy problems, which is believed to be caused by high local concentration of the growth hormone complex and at the injection site.

Büyükgebiz A. et al published in J. Pediatr. Endocrinol. Metab. 1999 January-February; 12(1):95-7 describes such a medical record (herein reference 1). This is a report of a patient with isolated GH deficiency due to 6.7 kb gene deletion who received high dose rhGH treatment and developed local lipoatrophies at injection sites without any antibody detection after 6 years of therapy. The etiology of the lipoatrophy is suspected to be by the direct lipolytic effect of high doses of rhGH.

Lipoatrophy related to the administration of rhGH is believed to be caused by the rhGH activity itself, by higher concentrations and by prolonged exposure. These higher concentrations occur near injections sites.

The chance that high growth hormone activity accumulates near the injection site is even higher in case that rhGH is PEGylated because of an increased residence time. In the case of PEGylated rhGH formulations, the tissue will experience a sustained and increased exposure to growth hormone activity, due to the fact that the PEGylated conjugate possess activity necessary for pharmacological activity and the conjugate is diffusion limited due to the conjugate size. The outcome is increased lipolysis at the injection site.

WO-A 2005/079838 describes pegylated hGH, wherein the hGH moiety is attached to a polyethylene glycol polymer via amino functional group, which can be considered as permanent attachment due to the stability of the amino group. An example of such a PEGylated hGH compound, which exhibits lipoatrophy, is the compound PHA-794428. Compound PHA-794428 is a PEGylated rhGH and also described in WO-A 2005/079838 from the company Pharmacia (acquired by Pfizer) and further described in Horm. Res. 2006; 65 (suppl. 4): 1-213, CF1-98 GH/IGF Treatment with title "First in-human study of PEGylated recombinant human growth hormone", Philip Harris et al. (herein reference 4).

According to the clinical trial information as published on www.clinicaltrials.gov, the trial was terminated on 10 Dec. 2007. Pfizer's decision to terminate the program was due to cases of injection-site lipoatrophy that were reported in the clinical Phase 2 studies after a single injection of PHA 794428.

WO-A 2006/1 02659 (Nektar) also describes and suggests rhGH-PEG conjugates (linear and branched types) via amide bond. The problem to be solved in WO-A 2006/102659 is described in paragraph [0005] on page 2. According to the applicant, the problem to be solved is reduced dosing frequency. Since rhGH therapy typically requires daily injections, patients, and in particular, pediatric patients, dislike the inconvenience and discomfort associated with this regimen. The solution described in Nektar's WO-A is the provision of new PEG-rhGH conjugates.

In table 6, [0257] of the WO-A it can be seen that the PEG-rhGH conjugates have a relatively low activity in vitro as compared to the native growth hormone without PEG. Despite the low in vitro activities, the PEGylated rhGH conjugates were active in vivo. In relation to this reads section [0261]: "Although the preliminary in vitro results suggest that increasing the amount of PEG attached to hGH reduces its ability to stimulate the hGH receptor, based on the preliminary in vivo results, it appears that a reduction in bioactivity is more than balanced by increased half-life and/or plasma availability, thus leading to a conclusion that the conjugates provided herein possess a superior pharmacodynamic effect in vivo when compared to unmodified rhGH at an identical dosing regimen".

WO-A 2006/1 02659 (Nektar) does not describe auto-cleavable linkers—i.e. it is simply observed that PEG-rhGH conjugates are active in vivo although their in vitro activities are significantly reduced. The problem of lipoatrophy is not addressed.

A solution to the challenge of engineering the desired properties of reduced lipoatrophy and reduced injection frequency into a PEGylated conjugate of hGH is the use of a prodrug approach. A prodrug is any compound that undergoes biotransformation before exhibiting its pharmacological effects. Prodrugs can thus be viewed as drugs containing specialized non-toxic protective groups used in a transient manner to alter or to eliminate undesirable properties in the parent molecule. In this case, a polymeric carrier would transiently reduce the activity of growth hormone and consequently reduce the likelihood of tissue lipolysis. Transient conjugation to a polymeric carrier would at the same time extend the half-life of the conjugate and therefore provide for a long-acting delivery of hGH.

Numerous macromolecular prodrugs are described in the literature where the macromolecular carrier is linked via a labile ester group to the medicinal agent (e.g. Y. Luo, M R Ziebell, G D Prestwich, "A Hyaluronic Acid—Taxol Antitumor Bioconjugate Targeted to Cancer Cells", Biomacromolecules 2000, 1, 208-218, J Cheng et al, Synthesis of Linear, beta-Cyclodextrin Based Polymers and Their Camptothecin Conjugates, Bioconjugate Chem. 2003, 14, 1007-1017, R. Bhatt et al, Synthesis and in Vivo Antitumor Activity of Poly(L-glutamic acid) Conjugates of 20(S)-Campththecin, J. Med. Chem. 2003, 46, 190-193; R. B. Greenwald, A. Pendri, C D. Conover, H. Zhao, Y. H. Choe, A. Martinez, K. Shum, S. Guan, J. Med. Chem., 1999, 42, 3657-3667; B. Testa, J. M: Mayer in Hydrolysis in Drug and Prodrug Metabolism, Wiley-VCH, 2003, Chapter 8) In theses cases, the conjugated functional group of the bioactive entity is a hydroxyl group or a carboxylic acid.

Especially for biomacromolecules but also for small molecule polymer prodrugs, it may be desirable to link the macromolecular carrier to amino groups (i.e. N-terminus or lysine amino groups of proteins) of the bioactive entity. This will be the case if masking the drug's bioactivity requires conjugation of a certain amino group of the bioactive entity, for instance an amino group located in an active center or a region or epitope involved in receptor binding. Also, during preparation of the prodrug, amino groups may be more chemoselectively addressed and serve as a better handle for conjugating carrier and drug because of their greater nucleophilicity as compared to hydroxylic or phenolic groups. This is particularly true for proteins which may contain a great variety of different reactive functionalities. In this case non-selective conjugation reactions lead to undesired product mixtures which require extensive characterization or purification and may decrease reaction yield and therapeutic efficiency of the product.

Prodrug activation may occur by enzymatic or non-enzymatic cleavage of the labile bridge between the carrier and the drug molecule, or a sequential combination of both, i.e. an enzymatic step followed by a nonenzymatic rearrangement.

In WO-A 2005/099768 PEGylated linker molecules with auto-cleavable linkers for a large group of biomolecules including somatropins (claim 6) are described. In WO-A 2005/099768, the problem to be solved is the interpatient variability and unpredictable effect of prodrug activation when enzymatic mechanism is involved (page 12, line 17-30). This application describes as a solution an aromatic linker, which may be PEG based. This linker-PEG binds the drug in away that the drug activity is significantly reduced. It is activated only on release of the drug, which is initiated by hydrolysis. The hydrolysis rate can be controlled chemically. No special emphasis is given on GH and relevant problems, like lipoatrophy, in relation to this as such.

In summary, none of the above mentioned citations describes a solution to develop a long-acting rhGH, based on a prodrug conjugate that can be administered less frequently without increasing the frequency of lipoatrophy.

Thus an object of the present invention is the provision of such a prodrug or a pharmaceutical composition comprising said prodrug to reduce the administration frequency of rhGH using PEG conjugated to rhGH without significantly inducing lipoatrophy.

SUMMARY OF THE INVENTION

Accordingly, the present invention provides a pharmaceutical composition comprising suitable pharmaceutical excipients and also comprising a human in vivo clinical effective amount of a recombinant human growth hormone rhGH PEGylated prodrug conjugate, wherein PEG is linked to rhGH via a self hydrolysable (autocleavage) transient linker; said prodrug conjugate is characterized in that:
  (1): the conjugate has a GH activity which is less than 5% of the native growth hormone without PEG; and
  (2): the linker autohydrolysis rate is such that the in vivo half-life is from 10 hours to 600 hours.

Property (1) ensures that the prodrug has a low incidence of lipoatrophy despite having a significantly extended duration of action in vivo. Without being limited by theory the present inventors believe that if the prodrug had a higher GH activity, this product would still induce lipoatrophy at a higher frequency than currently marketed rhGH products.

Property (2) ensures that rhGH (without PEG) is released gradually over time so one can administer the rhGH pharmaceutical product less frequently than human growth hormone, e.g. only once weekly or once monthly instead of daily administrations, while still retaining full efficacy compared to rhGH.

Preferably, the in vivo half life is up to 5 times shorter, e.g. 2, 3, 4, or 5 times shorter, than the corresponding hGH PEGylated prodrug conjugate's in vitro half-life. More preferably, the in vivo half-life is up to 3 times shorter than the corresponding hGH PEGylated prodrug conjugate's in vitro half-life. Most preferably, the in vivo half-life is up to 2 times shorter than or almost identical to the corresponding hGH PEGylated prodrug conjugate's in vitro half-life.

This invention applies to rhGH PEGylated prodrugs, in particular to rhGH PEGylated carrier prodrugs including cascade carrier prodrugs.

Prodrugs may be defined as therapeutic agents that are inactive per se but are predictably transformed into active metabolites (see B. Testa, J. M: Mayer in Hydrolysis in Drug and Prodrug Metabolism, Wiley-VCH, 2003, page 4). In carrier prodrug systems, many medicinal agents are inactive or show decreased biological activity when a polymer is covalently conjugated to the drug molecule. In these cases, a transient linkage of drug and carrier is applied in such a fashion that the medicinal agent is released from the polymeric carrier in vivo to regain its biological activity. The reduced biological activity of the prodrug as compared to the released drug is of advantage if a slow or controlled release of the drug is desired. In this case, a relatively large amount of prodrug may be administered without concomitant side effects and the risk of overdosing. Release of the drug occurs over time, thereby reducing the necessity of repeated and frequent administration of the drug.

In polymeric carrier prodrugs, the biologically active moieties are often linked to a polymeric carrier moiety by a labile bridge formed between the carrier moiety and a functional group of the drug molecule. Cleavage of a carrier prodrug generates a molecular entity (drug) of increased bioactivity and at least one side product, the carrier. This side product may be biologically inert (for instance PEG). After cleavage, the bioactive entity will reveal at least one previously conjugated and thereby masked or protected functional group, and the presence of this group typically contributes to the bioactivity.

The GH activity can be measured using methods known in the art. In this respect emphasis is made to example 1. Based on the fact that some transient linkers applicable for the present invention may have an in vitro half-life of less than 3000 h the respective GH activity measurement is made indirectly by determining the G H activity of a respective PEG conjugate comprising a permanent linker instead of the transient linker. This can be carried out as WO20061 02659 describes on page 74 paragraph 0240, the biological activity of rhGH and the conjugates described herein shall be assessed in vitro using an NB2-II rat lymphoma cell proliferation assay. Briefly, NB2-II cells derived from a rat lymphoma are incubated with rhGH, which lead to binding of the rhGH molecule to its receptor on the cell surface. Receptor binding induces the signal transduction cascade, which results in proliferation of the cells. Assay results are based on determined protein content, and a 100% bioactivity of unmodified rhGH.

Preferably, for the measurement of the GH activity the protocol as described in Example 24 is used.

The in vitro half life can be measured using methods known in the art. In this respect emphasis is made to example 2.

Accordingly, a second aspect of the invention relates to a clinical effective amount of the pharmaceutical composition comprising the rhGH PEGylated prodrug of the first aspect for use in a method for treatment of a GH related disease in a human person.

This second aspect may alternatively be formulated as a method for treatment of a GH related disease in a human person comprising administrating to a human person a clinical effective amount of the pharmaceutical composition comprising the rhGH PEGylated prodrug of the first aspect.

In a situation, where the residual activity of the prodrug (as is the case for transiently PEG conjugated rhGH) is significantly reduced as compared to native human GH, lipolytic effects may not occur even at prolonged exposure.

The herein described compounds termed rhGH PEGylated prodrugs are conjugates that may have significantly reduced residual activity compared to human GH. To exhibit therapeutically useful activity, rhGH has to be released from the prodrug conjugate, for which the described prodrugs herein need to undergo an activation step (e.g. 1,6-release mechanisms), termed herein as autocleavage, cleaving the PEG group from the drug. The 1,6-release mechanism is well described in WO-A 2005/099768.

Without being limited by theory, the present inventors believe that the herein disclosed transiently PEGylated rhGH conjugates significantly reduce lipoatrophy because of the low activity of the PEGylated rhGH conjugates, before PEG is gradually cleaved off by the autocleavable linker. This may ensure that the prodrugs will not induce lipoatrophy more frequently than human GH or other permanently PEGylated rhGH compounds as described above.

The problem underlying the present invention is also solved by a pharmaceutical composition comprising suitable pharmaceutical excipients and also comprising a prodrug conjugate of the human growth hormone (hGH) of formula (AA)

$$hGH-NH-L^a-S^o \qquad (AA),$$

wherein
hGH-NH represents the hGH residue;
$L^a$ represents afunctional group, which is self hydrolysable (auto-cleavable) by an auto-cleavage inducing group $G^a$; and
$S^o$ is a polymer chain having a molecular weight of at least 5 kDa and comprising an at least first branching structure $BS^1$, the at least first branching structure $BS^1$ comprising an at least second polymer chain $S^1$ having a molecular weight of at least 4 kDa, wherein at least one of $S^0$, $BS^1$, $S^1$ further comprises the auto-cleavage inducing group $G^a$ and wherein the branching structure $BS^1$ further comprises an at least third polymer chain $S^2$ having a molecular weight of at least 4 kDa or at least one of $S^0$, $S^1$ comprises an at least second branching structure $BS^2$ comprising the at least third polymer chain $S^2$ having a molecular weight of at least 4 kDa and wherein the molecular weight of the prodrug conjugate without the hGH-NH is at least 25 kDa and at most 1000 kDa, preferably at least 25 kDa and at most 500 kDa, even more preferably at least 30 kDa and at most 250 kDa, even more preferably at least 30 kDa and at most 120 kDa, even more preferably at least 40 kDa and at most 100 kDa, even more preferably at least 40 kDa and at most 90 kDa.

Surprisingly it was found, that the residual activity of a prodrug of the present invention can be efficiently reduced by providing a polymeric carrier having at least 3 chains of a certain minimum length (as defined by their molecular weight) and thus, in combination with a transient linker as described herein solve the problem of providing an hGH prodrug that can be administered less frequently without increasing the risk of lipoatrophy. The prodrug should therefore be water-soluble.

For at least bis-conjugated prodrugs the problem can be solved by a pharmaceutical composition comprising suitable pharmaceutical excipients and also comprising a prodrug conjugate of the human growth hormone (hGH) of formula (AB)

$$hGH-(NH-L-S^o)_n \qquad (AB),$$

wherein
n is 2, 3, or 4; preferably 2;
hGH(—NH)$_n$ represents the hGH residue;
each L is independently a permanent functional group LP; or a functional group $L^a$, which is self hydrolysable (auto-cleavable) by an auto-cleavage inducing group $G^a$; and
each $S^0$ is independently a polymer chain having a molecular weight of at least 5 kDa, wherein $S^0$ is optionally branched by comprising an at least first branching structure $BS^1$, the at least first branching structure $BS^1$ comprising an at least second polymer chain $S^1$ having a molecular weight of at least 4 kDa, wherein at least one of $S^0$, $BS^1$, $S^1$ further comprises the auto-cleavage inducing group $G^a$ and wherein the molecular weight of the prodrug conjugate without the hGH-NH is at least 25 kDa and at most 1000 kDa, preferably at least 25 kDa and at most 500 kDa, even more preferably at least 30 kDa and at most 250 kDa, even more preferably at least 30 kDa and at most 120 kDa, even more preferably at least 40 kDa and at most 100 kDa, even more preferably at least 40 kDa and at most 90 kDa.

Yet another aspect of the present invention is a prodrug conjugate as defined above.

Preferred embodiments of the present invention are described below, by way of examples only.

Definitions

Prior to a discussion of the detailed embodiments of the invention is provided a definition of specific terms related to the main aspects of the invention.

In general, all specific technical terms used herein shall be understood as the skilled person would understand them in the present technical context.

rhGH or hGH or GH or hGH residue refers to human growth hormone. NH-hGH is a hGH residue, wherein the —NH— of —NH-hGH represents an amino group of hGH.

The term "activity" herein is understood as the ability of growth hormone or a conjugate thereof, to evoke a biological response when administered to a mammal, e.g. in an in vivo model, or to produce a measureable response in an in vitro model as described in the examples.

In a prodrug system, measured activity will have two contributions, one from the released free drug entity and one from the not yet cleaved prodrug conjugate. In order to differentiate the activity of the prodrug conjugate, the term "residual activity" herein is understood as the portion of the measured prodrug activity that may be attributed to the prodrug conjugate.

The term "autocleavage" herein is understood as rate-limiting hydrolytic cleavage of the bond between the transient linker and the drug molecule rhGH in an aqueous buffered solution under physiological conditions of pH 7.4 and 37° C. Autocleavage does not require the presence of enzyme. This auto-cleavage or self hydrolysis is controlled by an auto-cleavage inducing group, which is part of the prodrug molecule. This auto-cleavage inducing group may be present as such or in a masked form so that unmasking is required before the self hydrolysis mechanism can start.

Linker autohydrolysis rate refers to the rate of cleavage of a hGH-PEGylated prodrug in vivo. As enzymatic or other effects almost always cause prodrug linker hydrolysis to proceed faster in vivo than in vitro, it is defined that a hGH PEG prodrug cleaves in an autohydrolytic fashion if the prodrug's in vivo half-life is up to 5 times shorter than the corresponding hGH PEGylated prodrug conjugate's in vitro half-life.

The term "transient linkage" or "transient linker" herein is understood as describing the lability of the linkage between PEG and rhGH in a rhGH PEGylated prodrug. In such transient linkages, rhGH is released from the corresponding prodrug with an in vivo linker half-life of up to 1200 hours.

The term "conjugate" herein is understood as one or more PEG molecules covalently bound to the drug herein being human growth hormone.

The term "transient conjugate" refers to hGH PEGylated prodrugs containing at least one transient linkage.

The term "permanent conjugate" refers to hGH PEGylated conjugates or prodrugs where the PEG polymer is connected to hGH by means of linkages with an in vitro half-life of at least 3000 hours.

In vitro half-life or in vitro linker half-life is the release of 50% of hGH from hGH PEGylated prodrug in buffer at pH 7.4 and 37° C.

The terms "in vivo half life" or "in vivo linker half-life" are understood as the time interval in which 50% of the initial proportion of the growth hormone is released from the hGH PEGylated prodrug after administration to the human body, calculated by taking into account the compound's corresponding conjugate half-life as described in example 2.

The term "conjugate half life" is understood as the time interval in which 50% of a hGH PEGylated permanent conjugate as defined above is cleared from the blood circulation.

The term "lipoatrophy" herein is understood as a medical term for localized loss of fat tissue. In the present context "lipoatrophy" refers to injection site lipoatrophy meaning tissue lipolysis occurring in close proximity of the injection site.

The term "prodrug" herein is understood is any compound that undergoes transformation before exhibiting its full pharmacological effects. Classification of prodrug systems is given by under IUPAC definitions (http://www.chem.qmul.ac.uk/iupac/medchem, accessed on 8 Mar. 2004):
Prodrug A prodrug is any compound that undergoes biotransformation before exhibiting its pharmacological effects. Prodrugs can thus be viewed as drugs containing specialized non-toxic protective groups used in a transient manner to alter or to eliminate undesirable properties in the parent molecule.
Double Prodrug (or Pro-Prodrug)

A double prodrug is a biologically inactive molecule which is transformed in vivo in two steps (enzymatically and/or chemically) to the active species.
Carrier-Linked Prodrug (Carrier Prodrug)

A carrier-linked prodrug is a prodrug that contains a temporary linkage of a given active substance with a transient carrier group that produces improved physicochemical or pharmacokinetic properties and that can be easily removed in vivo, usually by a hydrolytic cleavage.
Cascade Prodrug A cascade prodrug is a prodrug for which the cleavage of the carrier group becomes effective only after unmasking an activating group.
Biotransformation Biotransformation is the chemical conversion of substances by living organisms or enzyme preparations.

Correspondingly, a cascade autohydrolysis-inducing group becomes effective only after unmasking of certain autohydrolysis-inducing structural elements. There may be one or more cascade unmasking steps required to reveal the autohydrolyis-inducing structural elements. At least one of the unmasking steps may be based on a biotransformation step.

The term "a pharmaceutical composition comprising a human in vivo clinical effective amount of a recombinant human growth hormone (rhGH) PEGylated prodrug" is to be understood as an amount that is sufficiently high to obtain a wanted clinical effect in a human after administration of the pharmaceutical composition to the human—e.g. a wanted clinical effect in relation to treatment of a GH related disease. In the present context the skilled person routinely is able to adjust the amount of recombinant human growth hormone (rhGH) PEGylated prodrug to be administered in order to get a wanted clinical effect.

The term "physiological condition" herein is understood as any in vitro or in vivo condition, identical or resembling, the pH and temperature conditions in the human body. More specifically physiological conditions is referring to conditions at around pH 7.4 (pH 6.8 to pH 7.8) and about 37° C. (35° C. to 40° C.).

The term "linker" is frequently used in publications in the field of bioconjugation and broadly describes chemical structures used to connect two molecular entities. Such connectivity may be of permanent or transient nature.

A transient linker is a linker in which the conjugation of drug to PEG molecule is reversible. This implies that cleavage of the linker releases the drug in its native and active form. To structurally differentiate a transient linker unit from the polymer carrier may be difficult in the case of carrier prodrugs, particularly if the polymer is permanently attached to the linker and the linker-related degradation product is therefore not released as a consequence of prodrug cleavage. Structural characterization of a linker is even more challenging if the linker is functioning both as an auto-cleavage inducing group and a branching unit. Therefore, within the meaning of the present invention, the term linker may be used synonymous with a combination of afunctional group La and an auto-cleavage inducing group $G^a$. In cases where carrier prodrugs are described where the carrier is a branched PEG, it is preferred to use structural descriptions based on combinations of $L^a$ and $G^a$. In such case, the cleavage-inducing group $G^a$ is considered to be part of the carrier polymer. Variation of the chemical nature of $G^a$ allows the engineering of the properties of the self-cleaving properties of a corresponding carrier-linked prodrug to a great extent.

The term "permanent linker" refers to a PEG conjugate to a hGH-donated primary amino group by formation of an aliphatic amide or aliphatic carbamate. If conventional PEGylation reagents are used, resulting conjugates are usually very stable against hydrolysis and the rate of cleavage of the amide or carbamate bond would be too slow for therapeutic utility in a prodrug system. Nevertheless such permanent linker conjugates are useful for the investigation of the therapeutic utility of a prodrug conjugate as they allow for assessment of residual activity.

If such stable linkages are to be employed in a prodrug approach, cleavage of the functional group is not possible in a therapeutically useful timeframe without enzymatic catalysis.

The term "water-soluble prodrug" means a prodrug that is soluble in water under physiological conditions. Typically, a water-soluble prodrug will transmit at least 75%, more preferably at least 95%, of light transmitted by the same solution after filtering. On a weight basis, a water soluble polymer will preferably be at least about 35% (by weight) soluble in water, still more preferably at least about 50% (by weight), still more preferably at least about 70% (by weight), still more preferably at least about 85% (by weight), still more preferably at least about 95% (by weight) or completely soluble in water.

The term "PEG" or "pegylation residue" is used herein exemplary for suitable water-soluble polymers characterized by repeating units. Suitable polymers may be selected from the group consisting of polyalkyloxy polymers, hyaluronic acid and derivatives thereof, polyvinyl alcohols, polyoxazolines, polyanhydrides, poly(ortho esters), polycarbonates, polyurethanes, polyacrylic acids, polyacrylamides, polyacrylates, polymethacrylates, polyorganophosphazenes, polysiloxanes, polyvinylpyrrolidone, polycyanoacrylates, and polyesters.

PEG chains may consist of an interconnecting moiety, a polymer moiety, and an end group.

In case of branched monoconjugates of hGH PEGylated prodrugs, the critical distance defines the shortest distance between the attachment site of PEG chain $S^0$ to $L^a$ and the first branching structure $BS^1$ measured as connected atoms.

The term "PEG load" herein is understood as a descriptor of the molecular mass of a polymer chain consisting of a number of repeating units attached to hGH. Total PEG load is understood as the total molecular mass of all polymeric carrier chains attached to hGH on a molecular basis.

DETAILED DESCRIPTION OF THE INVENTION

Pharmaceutical Composition Comprising Suitable Pharmaceutical Excipients

As known to the skilled person a pharmaceutical composition comprises pharmaceutically acceptable excipients and/or carriers.

"Pharmaceutically acceptable" is meant to encompass any excipient and/or additive, which does not interfere with the effectiveness of the biological activity of the active ingredient and that, is not toxic to the host to which it is administered.

In a preferred embodiment the pharmaceutical composition is a composition for subcutaneous administration, intramuscular administration or intravenous injection.

This is examples of preferred administration routes for treatment of a relevant disorder/disease as described herein.

The pharmaceutical composition may comprise other active ingredients than an rhGH PEGylated prodrug as described herein.

Recombinant Human Growth Hormone (rhGH)

Since the recombinant human G H is identical in sequence to natural human GH, the term recombinant human growth hormone (rhGH) relates herein also to so-called biogenerics equivalents. Thus, the terms rhGH and hGH can be used synonymously within the meaning of the present invention.

The term "biogenerics" herein is understood generic forms of biopharmaceuticals; molecules developed using biological processes, usually through modern biotechnology activity. Generic chemical pharmaceuticals can be defined as those molecules which, when compared with the originator product: have essentially similar activity, are essentially chemically identical to their branded counterparts, are bioequivalent, achieve market authorization through an abbreviated procedure following patent expiry.

As known to the skilled person, it is today routine work to make e.g. minor amino changes of a biologies of interest (herein GH) without significantly affecting the activity of the biologies.

Besides recombinant human and biogenerics, the term recombinant human growth hormone (rhGH) relates herein also to all possible rhGH polypeptides.

A precise description of possible rhGH polypeptides is given in WO-A 2005/079838 from the Pharmacia Corporation provided on page 15, paragraph 0043 till and including paragraph 0053.

The term "hGH polypeptide or hGH protein", when used herein, encompasses all hGH polypeptides, preferably from mammalian species, more preferably from human and murine species, as well as their variants, analogs, orthologs, homologs, and derivatives, and fragments thereof that are characterized by promoting growth in the growing phase and in maintaining normal body composition, anabolism, and lipid metabolism.

The term "hGH polypeptide or protein" preferably refers to the 22 kDa hGH polypeptide having a sequence as disclosed in A. L. Grigorian et al., Protein Science (2005), 14, 902-913 as well as its variants, homologs and derivatives exhibiting essentially the same biological activity (promoting growth in the growing phase and in maintaining normal body composition, anabolism, and lipid metabolism). More preferably, the term "hGH polypeptide or protein" refers to the polypeptide having exactly the abovementioned sequence.

Derivatives of hGH encompass especially hGH prodrug conjugates comprising permanently linked polymers, like PEG, i.e. the prodrug of the present invention may comprise in addition to one or more transient linker polymer conjugates further permanent linker polymer conjugates.

The term "hGH polypeptide variants", as used herein, refers to polypeptides from the same species but differing from a reference hGH polypeptide. Generally, differences are limited so that the amino acid sequences of the reference and the variant are closely similar overall and, in many regions, identical. Preferably, hGH polypeptides are at least 70%, 80%, 90%, 95%, 96%, 97%, 98% or 99% identical to a reference hGH polypeptide, preferably the hGH polypeptide having a sequence as indicated in A. L. Grigorian et al., Protein Science (2005), 14, 902-913. By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein.

Such hGH polypeptide variants may be naturally occurring variants, such as naturally occurring allelic variants encoded by one of several alternate forms of a hGH occupying a given locus on a chromosome of an organism, or isoforms encoded by naturally occurring splice variants originating from a single primary transcript. Alternatively, a hGH polypeptide variant may be a variant that is not known to occur naturally and that can be made using art-known mutagenesis techniques.

It is known in the art that one or more amino acids may be deleted from the N-terminus or C-terminus of a bioactive peptide or protein without substantial loss of biological function (see for instance, Ron et al., (1993), Biol Chem., 268 2984-2988 i which disclosure is hereby incorporated by reference in its entirety).

It also will be recognized by one of ordinary skill in the art that some amino acid sequences of hGH polypeptides can be varied without significant effect of the structure or function of the protein. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, hereby incorporated by reference in its entirety, wherein the authors indicate that there are two main approaches for studying the tolerance of an amino acid sequence to change.

The first method relies on the process of evolution, in which mutations are either accepted or rejected by natural selection. The second approach uses genetic engineering to introduce amino acid changes at specific positions of a cloned hGH and selections or screens to identify sequences that maintain functionality. These studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie et al., (1990) supra, and the references cited therein.

Typically seen as conservative substitutions are the replacements, one for another, among the aliphatic amino acids Ala, Val, Leu and Phe interchange of the hydroxyl residues Ser and Thr, exchange of the acidic residues Asp and Glu, substitution between the amide residues Asn and Gin, exchange of the basic residues Lys and Arg and replacements among the aromatic residues Phe, Tyr. In addition, the following groups of amino acids generally represent equivalent changes: (1) Ala, Pro, Gly, Glu, Asp, Gin, Asn, Ser, Thr; (2) Cys, Ser, Tyr, Thr; (3) Val, lie, Leu, Met, Ala, Phe; (4) Lys, Arg, His; (5) Phe, Tyr, Trp, His.

The term hGH polypeptide also encompasses all hGH polypeptides encoded by hGH analogs, orthologs, and/or species homologues. As used herein, the term "hGH analogs" refers to hGHs of different and unrelated organisms which perform the same functions in each organism but which did not originate from an ancestral structure that the organisms' ancestors had in common. Instead, analogous hGHs arose separately and then later evolved to perform the same function (or similar functions). In other words, analogous hGH polypeptides are polypeptides with quite different amino acid sequences but that perform the same biological activity, namely promoting growth in the growing phase and in maintaining normal body composition, anabolism, and lipid metabolism. As used herein, the term "hGH orthologs" refers to hGHs within two different species which sequences are related to each other via a common homologous hGH in an ancestral species but which have evolved to become different from each other. As used herein, the term "hGH homologs" refers to hGHs of different organisms which perform the same functions in each organism and which originate from an ancestral structure that the organisms' ancestors had in common. In other words, homologous hGH polypeptides are polypeptides with quite similar amino acid sequences that perform the same biological activity, namely promoting growth in the growing phase and in maintaining normal body composition, anabolism, and lipid metabolism. Preferably, hGH polypeptide homologs may be defined as polypeptides exhibiting at least 40%, 50%, 60%, 70%, 80%, 90%, 95%, 96%, 97%, 98% or 99% identity to a reference hGH polypeptide, preferably the hGH polypeptide having a sequence as mentioned above.

Thus, a hGH polypeptide may be, for example: (i) one in which one or more of the amino acid residues are substituted with a conserved or non-conserved amino acid residue (preferably a conserved amino acid residue) and such substituted amino acid residue mayor may not be one encoded by the genetic code: or (ii) one in which one or more of the amino acid residues includes a substituent group: or (iii) one in which the hGH polypeptide is fused with another compound, such as a compound to increase the half-life of the polypeptide (for example, polyethylene glycol): or (iv) one in which the additional amino acids are fused to the above form of the polypeptide, such as an IgG Fc fusion region peptide or leader or secretory sequence or a sequence which is employed for purification of the above form of the polypeptide or a pro-protein sequence.

hGH polypeptides may be monomers or multimers. Multimers may be dimers, trimers, tetramers or multimers comprising at least five monomeric polypeptide units. Multimers may also be homodimers or heterodimers. Multimers may be the result of hydrophobic, hydrophilic, ionic and/or covalent associations and/or may be indirectly linked, by for example, liposome formation. In one example, covalent associations are between the heterologous sequences contained in a fusion protein containing a hGH polypeptide or fragment thereof (see, e.g., U.S. Pat. No. 5,478,925, which disclosure is hereby incorporated by reference in its entirety). In another example, a hGH polypeptide or fragment thereof is joined to one or more polypeptides that may be either hGH polypeptides or heterologous polypeptides through peptide linkers such as those described in U.S. Pat. No. 5,073,627 (hereby incorporated by reference).

Another method for preparing multimer hGH polypeptides involves use of hGH polypeptides fused to a leucine zipper or isoleucine zipper polypeptide sequence known to promote multimerization of the proteins in which they are found using techniques known to those skilled in the art including the teachings of WO 94/10308. In another example, hGH polypeptides may be associated by interactions between Flag® polypeptide sequence contained in fusion hGH polypeptides containing Flag® polypeptide sequence. hGH multimers may also be generated using chemical techniques known in the art such as cross-linking using linker molecules and linker molecule length optimization techniques known in the art (see, e.g., U.S. Pat. No. 5,478,925), techniques known in the art to form one or more inter-molecule cross-links between the cysteine residues located within the sequence of the polypeptides desired to be contained in the multimer (see, e.g., U.S. Pat. No. 5,478,925, addition of cysteine or biotin to the C terminus or N-terminus of hGH polypeptide and techniques to generate multimers containing one or more of these modified polypeptides (see, e.g., U.S. Pat. No. 5,478,925), or any of the 30 techniques to generate liposomes containing hGH multimers (see, e.g., U.S. Pat. No. 5,478,925), which disclosures are incorporated by reference in their entireties.

As used herein, the term "hGH polypeptide fragment" refers to any peptide or polypeptide comprising a contiguous span of a part of the amino acid sequence of an hGH polypeptide, preferably the polypeptide having the above-mentioned sequence.

rhGH PEGylated Prodrug—Preferred PEG, Polymer Chains

As discussed above, the rhGH PEGylated prodrug as described herein shall have a relatively low activity.

Accordingly, in a preferred embodiment the total PEG load per growth hormone molecule amounts to at least 25 kDa. Generally the total PEG load will be less than 1000 kDa. Preferably, the PEG load is at least 25 kDa and at most 500 kDa, even more preferably at least 30 kDa and at most 250 kDa, even more preferably at least 30 kDa and at most 120 kDa, even more preferably at least 40 kDa and at most 100 kDa, even more preferably at least 40 kDa and at most 90 kDa.

PEG may be attached to hGH through one or more anchoring points. In case of one anchoring point, the corresponding PEG in the hGH PEG prodrug monoconjugate will be branched and contain at least 3 chains. In case of more than one anchoring point, such as in a bisconjugate, the corresponding PEG in the hGH PEG prodrug may be branched or linear. Bisconjugates may contain one or two transient linkages, and PEG may be linear or branched or contain a mixture of one linear and one branched chain. In case the bisconjugate contains one transient linkage and one linear and one branched chain the transient linkage may be on either chain. In case a branched PEG chain is used, there may be one or more branching units.

A branched PEG is a PEG molecule consisting of a branching point connecting two or more PEG chains, to form a molecule with one anchoring point for attachment to growth hormone. This could be two 20 kDa PEG chains joined to form one branched 40 kDa PEG molecule. In the case where the molecule contains two or three branching points, the molecule is referred to 3 and 4 armed PEG, respectively.

In summary and within the restrictions mentioned above, the PEG polymer is not limited to a particular structure and can be linear, branched, or multi-armed (e.g. forked PEG or PEG attached to a polyol core), dendritic, or with degradable linkers.

Without being limited to theory the PEG load is intended to provide a suitable molecular mass to get the required relatively low activity and not having a too high molecular mass of the PEG that could create other problems.

The PEGylation to native human GH may occur on several lysine groups or on the N-terminal amine (F1) as well described by Clark et al. (reference 2 herein) on page 21973 table III. Highly reactive are positions F1 and LYS-140. Moderately reactive positions are LYS-1 15, LYS-38, and LYS-70. Poorly reactive are positions LYS-172, LYS-41, LYS-158 and LYS-168.

In more general terms the PEG used herein in combination with a transient linker may reduce the risk of lipoatrophy by suitable choice of said polymer. However the principles of the present invention also apply to polymers other than PEG. Thus the term PEG is only used herein exemplary for suitable polymers.

Thus, in a preferred embodiment, hGH PEG prodrug is a monoconjugate conjugated with one of its primary amino groups to an auto-cleavable functional group $L^a$ to a polymer chain $S^0$. This polymer chain $S^0$ has a molecular weight of at least 5 kDa and comprises at least one branching structure $BS^1$. The branching structure $BS^1$ comprises a second polymer chain $S^1$, which has a molecular weight of at least 4 kDa.

As outlined above, at least a third polymer chain $S^2$ is required having a molecular weight of at least 4 kDa. The polymer chain $S^2$ may be a part of $BS^1$ or may be a further branch of $S^0$ or $S^1$ resulting in a further branching structure $BS^2$, which comprises $S^2$.

Optionally more than 3 polymer chains are present in the prodrug conjugate of the present invention, e.g. 4, 5, 6, 7, or 8. However each further polymer chain has a molecular weight of at least 4 kDa. The total number of polymer chains is limited by the total weight of the prodrug conjugate being at most 1000 Da (without hGH-NH).

Thus a preferred embodiment of the present invention relates to a composition, wherein at least one of the branching structures $BS^1$, $BS^2$ comprises a further fourth polymer chain $S^3$ having a molecular weight of at least 4 kDa or one of $S^0$, $S^1$, $S^2$ comprises a third branching structure $BS^3$ comprising the at least fourth polymer chain $S^3$ having a molecular weight of at least 4 kDa.

The auto-cleavage inducing group $G^a$, which is necessary for the auto-cleavage of $L^a$ is comprised by one of the branching structures or polymer chains.

Optionally, one of the branching structures serves as group $G^a$ so that the branching structure consists of $G^a$ (instead of comprising said group), which is also encompassed by the term "comprising".

The preparation of a prodrug conjugate (AA) normally results in a mixture of conjugates, where several primary amino groups of hGH are conjugated resulting in different mono-conjugated, different bi-conjugated, different tri-conjugated, etc., prodrugs. Corresponding monoconjugated, bisconjugated or trisconjugated hGH PEG prodrugs can be separated by standard methods known in the art, like column chromatography and the like.

In monoconjugates of hGH PEG prodrugs, the at least three polymer chains $S^0$, $S^1$, $S^2$ contain a "polymer moiety", which is characterized by one or more repeating units, which may be randomly, block wise or alternating distributed. In addition, the at least three polymer chains $S^0$, $S^1$, $S^2$ show an end group, which is typically a hydrogen atom or an alkyl group having from 1 to 6 carbon atoms, which may be branched or unbranched, e.g. a methyl group, especially for PEG based polymer chains resulting in so called mPEGs.

It is pointed out that the polymer moieties within the at least three polymer chains $S^0$, $S^1$, $S^2$ may have further chain-like substituents, originating from the repeating units and resulting in chains having less than 4 kDa of molecular weight and which are not considered as polymer chains $S^0$, $S^1$, $S^2$, etc. Preferably, the at least three polymer chains $S^0$, $S^1$, $S^2$ carry substituents of less than 1000 Da molecular weight.

A relevant structural feature of $S^0$ is its critical distance. The critical distance defines the shortest distance between the attachment site of $S^0$ to $L^a$ and the first branching structure $BS^1$ measured as connected atoms. The length of the critical distance has an effect on the residual activity as discussed for compound 33. The critical distance is preferably less than 50, more preferred less than 20, most preferred less than 10.

The at least three polymer chains $S^0$, $S^0$ and $S^2$ typically each contain an interconnecting moiety. Ga is present in at least one of the interconnecting moieties. For polymer chains other than $S^0$, the interconnecting moiety is the structural element connecting the polymer moiety of for instance $S^1$ with $BS^1$ and the polymer moiety of $S^2$ with $BS^2$. For $S^0$, the interconnecting moiety is the structural element connecting $L^a$ and $BS^1$.

Interconnecting moieties may consist of a $C_{1-50}$ alkyl chain, which is branched or unbranched and which is optionally interrupted or terminated by hetero atoms or functional groups selected from the group consisting of —O—; —S—; N(R); C(O); C(O)N(R); N(R)C(O); one or more carbocycles or heterocycles, wherein R is hydrogen or a $C_{1-20}$ alkyl chain, which is optionally interrupted or terminated by one or more of the abovementioned atoms or groups, which further have a hydrogen as terminal atom; and wherein a carbocycle is phenyl; naphthyl; indenyl; indanyl; tetralinyl; $C_{3-10}$ cycloalkyl; and wherein the heterocycle is a 4 to 7 membered heterocyclyl; or 9 to 11 membered heterobicyclyl.

"$C_{3-10}$ cycloalkyl" or "$C_{3-10}$ cycloalkyl ring" means a cyclic alkyl chain having 3 to 10 carbon atoms, which may have carbon-carbon double bonds being at least partially saturated, e.g. cyclopropyl, cyclobutyl, cyclopentyl, cyclohexyl, cyclohexenyl, cycloheptyl, cyclooctyl, cyclononyl, cyclodecyl. Each hydrogen of a cycloalkyl carbon may be replaced by a substituent. The term "$C_{3-10}$ cycloalkyl" or "$C_{3-10}$ cycloalkyl ring" also includes bridged bicycles like norbonane or norbornene.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. "9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane.

The carbocycle, heterocycle and heterobicycle may be substituted by $C_{1-20}$ alkyl, optionally interrupted or terminated by hetero atoms or functional groups selected from the group consisting of —O—; —S—; N(R); C(O); C(O)N(R); N(R)C(O), wherein R is hydrogen or a $C_{M\ O}$ alkyl chain, which is optionally interrupted or terminated by one or more of the abovementioned atoms or groups, which further have a hydrogen as terminal atom.

The polymer moiety of the at least three chains $S^0$, $S^1$, $S^2$ form the majority part of the chains, preferably at least 90% of the molecular weight of each chain, more preferred at least 95%, even more preferred at least 97.5%, even more preferred at least 99%. Thus, the basis of the chains is represented by the polymer moiety.

Preferably, the at least three chains $S^0$, $S^1$, $S^2$ are independently based on a polymer selected from the group consisting of polyalkyloxy polymers, hyaluronic acid and derivatives thereof, polyvinyl alcohols, polyoxazolines, polyanhydrides, poly(ortho esters), polycarbonates, polyurethanes, polyacrylic acids, polyacrylamides, polyacrylates, polymethacrylates, polyorganophosphazenes, polysiloxanes, polyvinylpyrrolidone, polycyanoacrylates, and polyesters.

Preferably, the at least three chains $S^0$, $S^1$, $S^2$ are based on the same polymer. Preferably, the at least three chains $S^0$, $S^1$, $S^2$ are based on polyalkyoxy polymers. Even more preferred the at least three chains $S^0$, $S^1$, $S^2$ are polyethylene glycol based.

The same applies for further chains $S^3$, $S^4$, $S^5$, etc., accordingly.

The chain $S^0$ comprises a branching structure $BS^1$, so that $S^1$ is linked to $S^0$. For the linkage of $S^2$ the branching structure $BS^1$ may be used or a further branching structure $BS^2$ is present, which may be a part $S^0$ or $S^1$. Accordingly, further branching structures may be present, when further chains are present. For example in case a chain $S^3$ is present it may be linked to $BS^1$, $BS^2$ or a branching structure $BS^3$. The branching structure $BS^3$, if present, may be part of $S^0$, $S^1$, or $S^2$.

In general any chemical entity, which allows the branching of a chain, may be used. Preferably, the branching structures are independently selected from the group consisting of at least 3-fold substituted carbocycle, at least 3-fold substituted heterocycle, a tertiary carbon atom, a quaternary carbon atom, and a tertiary nitrogen atom, wherein the terms carbocycle and heterocycle are defined as indicated above.

rhGH PEGylated Prodrug—Transient Linker Structures, $L^a$, $G^a$

In publications in the field of auto-cleavage inducing groups are sometimes called linkers to discriminate their structure from the carrier. Nevertheless it is often difficult to clearly separate these structural features. Therefore, within the meaning of the present invention the cleavage-inducing group $G^a$ is considered to be part of the carrier S, comprising at least $S^0$, $S^1$, $S^2$, $BS^1$, and optionally $BS^2$. Variation of the chemical nature of $G^a$ allows the engineering of the properties of the self-cleaving properties of a corresponding carrier-linked prodrug to a great extent.

As discussed above, a PEGylated-prodrug, wherein the drug is for example rhGH as described in patent application WO-A 2005/099768, and has a characteristic of release, which is therein described as the 1,6 cleavage system without the production of toxic aromatic compounds. In this document is broadly described numerous herein relevant suitable transient linker structures to get a relevant release profile of interest.

Other transient linker structures are generically/broadly described in e.g. other Complex Biosystems GmbH applications such as WO-A 2005/034909, WO-A 2005/099768, WO-A 2006/003014 and WO-A 2006/136586.

More transient linker structures are broadly described in e.g. WO-A 99/30727 (Enzon Inc).

In order to solve the present problems for GH as discussed herein, the present inventors have selected suitable preferred transient linker structures to get the herein described relevant functional properties of the rhGH PEGylated prodrug. Based on the herein detailed description of preferred linker structures it is within the skilled person knowledge to make other suitable preferred transient linker structures that could give an rhGH PEGylated prodrug with the herein described relevant functional properties.

Especially, suitable transient linker structures, which are self hydrolysable (auto-cleavable) can be chosen for incorporation into $S^0$. The herein selected linker structures are described in detail below.

Ideally, a conjugate of the invention will possess one or more of the following features and/or advantages over current rhGH conjugates or formulations; can easily be synthesized in good yields, have half life's falling within preferred range, can be purified to provide homogeneous conjugate compositions, exhibit activity after auto-cleavage such as in vitro and in vivo activity and have pharmacodynamic effects superior to unmodified rhGH and previously described rhGH conjugates and do not cause lipoatrophy. The herein described structures exhibit release properties as required herein.

In general, carrier-linked prodrugs require the presence of a cleavable functional group connecting drug and carrier. In the absence of autohydrolysis-inducing groups, functional groups that involve a drug-donated amino group such as aliphatic amide or carbamate bonds $L^a$ are usually very stable against hydrolysis and the rate of cleavage of the amide bond would be too slow for therapeutic utility in a prodrug system.

If such stable linkages are to be used in carrier-linked prodrugs, cleavage of the functional group is not possible in a therapeutically useful timeframe without biotransformation. In these cases, the linker displays a structural motif that is recognized as a substrate by a corresponding endogenous enzyme. In such a case, the cleavage of the functional bond $L^a$ involves a complex comprising the enzyme. Examples are peptide linkers that are recognized by endogenous proteases and cleaved enzymatically.

Enzyme levels may differ significantly between individuals resulting in biological variation of prodrug activation by the enzymatic cleavage. The enzyme levels may also vary depending on the site of administration. For instance it is known that in the case of subcutaneous injection, certain areas of the body yield more predictable therapeutic effects than others. Such high level of interpatient variability is not desirable. Furthermore, it is difficult to establish an in vivo-in vitro correlation of the pharmacokinetic properties for such enzyme-dependent carrier-linked prodrugs. In the absence of a reliable in vivo-in vitro correlation optimization of a release profile becomes a cumbersome task.

In order to avoid patient-to-patient and injection site variability, it is desirable to employ carrier-linked prodrugs that exhibit cleavage kinetics in a therapeutically useful timeframe without the requirement for additional enzymatic contribution to cleavage. Especially for high molecular weight carriers, specifically for branched polymeric carriers, access to the connecting functional group $L^a$ may be restricted for enzymes due to sterical crowding. Therefore there exists a need to devise carrier-linked prodrugs that exhibit self-cleaving properties.

Autocleavage kinetics can for instance be measured in vitro by recording hydrolysis rates in buffered solution without enzyme.

In order to introduce hydrolytic lability into functional groups L such as amides or carbamates, it is necessary to engineer structural chemical components into the carrier in order to function for instance as neighbouring groups in proximity to the functional group. Such autocleavage-inducing chemical structures that exert control over the cleavability of the prodrug amide bond are termed auto-cleavage inducing groups $G^a$. Autocleavage-inducing groups can have a strong effect on the rate of hydrolysis of a given functional group $L^a$.

Preferred $L^a$ are selected from the group consisting of C(O)—O—, and C(O)—, which form together with the primary amino group of hGH a carbamate or amide group.

Thus, a composition of the present invention is preferred, wherein $L^a$ is selected from the group consisting of C(O)—O—, and C(O)—, which form together with the primary amino group of hGH a carbamate or amide group resulting in formula (AA1) or (AA2)

hGH-NH—C(O)O—S°      (AA1),

hGH-NH—C(O)—S°      (AA2).

The following sections will list various structural components that may function as cleavage-inducing groups $G^a$.

The group $G^a$ represents an autocleavage inducing group. $G^a$ may be present as such or as a cascade autocleavage-inducing group, which is unmasked to become effective by means of an additional hydrolytical or enzymatic cleavage step. If $G^a$ is present as such, it governs the rate-limiting autohydrolysis of $L^a$.

Examples for $G^a$:

A. J. Garman et al. (A. J. Garman, S. B. Kalindjan, FEBS Lett. 1987, 223 (2), 361-365 1987) used PEG5000-maleic anhydride for the reversible modification of amino groups in tissue-type plasminogen activator and urokinase. Regeneration of functional enzyme from PEG-uPA conjugate upon incubation at pH 7.4 buffer by cleavage of the maleamic acid lineage followed first order kinetics with a half-life of 6.1 h.

Simple aromatic moieties may infer lability to a connected carbamate bond (WO-A 01/47562). For instance, substituted or unsubstituted fluorenylmethyl group were used to labilize carbamate linkages to various bioactive agents in a prodrug approach (Tsubery et al. J Biol Chem 279 (2004) 381 18-24). Two PEG chains were attached to a fluorenyl moiety in WO-A 2007/075534.

Thus, $G^a$ is an aromatic ring or fluorenylmethyl directly attached to a carbamate functional group $L^a$.

Accordingly, a composition of the present invention is preferred, wherein $G^a$ is an aromatic ring or fluorenylmethyl directly attached to a carbamate functional group formed by $L^a$ and the primary amino group of hGH.

Alternatively, transformation of $G^a$ may induce a molecular rearrangement within S such as a 1,4 or 1,6-elimination. The rearrangement renders $L^a$ so much more labile that its cleavage is induced. The transformation of $G^a$ is the rate-limiting step in the cascade mechanism. Ideally, the cleavage rate of the temporary linkage is identical to the desired release rate for the drug molecule in a given therapeutic scenario. In such a cascade system base on 1,6 elimination, it is desirable that the cleavage of $L^a$ is substantially instantaneous after its lability has been induced by transformation of $G^a$. In addition it is desirable that the rate-limiting cleavage kinetics proceed in a therapeutically useful timeframe without the requirement for additional enzymatic contribution in order to avoid the drawbacks associated with predominantly enzymatic cleavage discussed above.

R. B. Greenwald, A. Pendri, C D. Conover, H. Zhao, Y. H. Choe, A. Martinez, K. Shum, S. Guan, J. Med. Chem., 1999, 42, 3657-3667 & PCT Patent Application WO-A 99/30727 described a methodology for synthesizing poly(ethylene glycol) prodrugs of amino-containing small molecule compounds based on 1,4- or 1,6-benzyl elimination. In this approach the amino group of the drug molecule is linked via a carbamate group to a PEGylated benzyl moiety. The poly(ethylene glycol) was attached to the benzyl group by ester, carbonate, carbamate, or amide bonds. The release of PEG from the drug molecule occurs through a combination of autohydrolysis and enzymatic cleavage. The cleavage of the release-triggering masking group is followed in this approach by the classical and rapid 1,4- or 1,6-benzyl elimination. This linker system was also used for releasable poly(ethylene glycol) conjugates of proteins (S. Lee, R. B. Greenwald et al. Bioconj. Chem. 2001, 12 (2), 163-169). Lysozyme was used as model protein because it loses its activity when PEGylation takes place on the epsilon-amino group of lysine residues. Various amounts of PEG linker were conjugated to the protein. Regeneration of native protein from the PEG conjugates occurred in rat plasma or in non-physiological high pH buffer. See also F. M. H. DeGroot et al. (WO-A 2002/083180 and WO-A 2004/043493), and D. Shabat et al. (WO-A 2004/019993).

Thus, $L^a$ is a carbamate functional group, the cleavage of said group is induced by a hydroxyl or amino group of $G^a$ via 1,4- or 1,6 benzyl elimination of $S^0$, wherein $G^a$ contains ester, carbonate, carbamate, or amide bonds that undergo rate-limiting transformation. In effect, $G^a$ may be cleaved off by hydrolysis.

Accordingly, a composition of the present invention is preferred, wherein $L^a$ forms together with the amino group of hGH a carbamate functional group, the cleavage of said group is induced by a hydroxyl or amino group of $G^a$ via 1,4- or 1,6 benzyl elimination of $S^0$, wherein $G^a$ contains ester, carbonate, carbamate, or amide bonds that undergo rate-limiting transformation.

$G^a$ may contain a cascade cleavage system that is enabled by components of $G^a$ that are composed of a structural combination representing the aforementioned precursor. A precursor of $G^a$ may contain additional temporary linkages such as an amide, ester or a carbamate. The stability, or susceptibility to hydrolysis of the precursor's temporary linkage (e.g. carbamate) may be governed by autohydrolytic properties or may require the activity of an enzyme.

Antczak et al. (Bioorg Med Chem 9 (2001) 2843-48) describe a reagent which forms the basis for a macromolecular cascade prodrug system for amine-containing drug molecules. In this approach an antibody serves as the carrier, a stable bond connects the antibody to an activating group, carrying a cleavable masking group. Upon removal of the ester-linked masking group, La cleaves and releases the drug compound.

D. Shabat et al. (Chem. Eur. 3. 2004, 10, 2626-2634) describe a polymeric prodrug system based on a mandelic acid activating group. In this system the masking group is linked to the activating group by a carbamate bond. The activating group is conjugated permanently to a polyacrylamide polymer via an amide bond. After activation of the masking group by a catalytic antibody, the masking group is cleaved by cyclization and the drug is released. The activating group is still connected to the polyacrylamide polymer after drug release.

M.-R. Lee et al. describe (Angew. Chem. 2004, 116, 1707-17 10) a similar prodrug system based on mandelic acid activating group and ester-linked masking group.

Nevertheless in these linkers a 1,6 elimination step still generates a highly reactive aromatic intermediate. Even if the aromatic moiety remains permanently attached to the polymeric carrier, side reactions with potentially toxic or immunogenic effects may be caused.

Greenwald et al. published in 2000 a poly(ethylene glycol) drug delivery system of amino-containing prodrugs based on trimethyl lock lactonization (R. B. Greenwald et al. J. Med. Chem. 2000, 43(3), 457-487; WO-A 02/089789). In this prodrug system substituted o-hydroxyphenyl-dimethylpropionic acid is coupled to amino groups of drug molecules by an amide bond. The hydroxy group is linked to PEG by an ester, carbonate, or carbamate group. The rate determining step in drug release is the enzymatic cleavage of these functional groups followed by fast amide cleavage by lactonization, liberating an aromatic lactone side product.

More recently, R. B. Greenwald et al. (Greenwald et al. J. Med. Chem. 2004, 47, 726-734) described a PEG prodrug system based on bis-(N-2-hydroxyethyl)glycin amide (bicin amide) linker. In this system two PEG molecules are linked to a bicin molecule coupled to an amino group of the drug molecule. The first two steps in prodrug activation is the enzymatic cleavage of both PEG molecules. Different linkages between PEG and bicin are described resulting in different prodrug activation kinetics. The main disadvantage of this system is the slow hydrolysis rate of bicin amide conjugated to the drug molecule ($t_{1/2}$=3 h in phosphate buffer) resulting in the release of a bicin-modified prodrug intermediate that may show different pharmacokinetic and pharmacodynamic properties than the parent drug molecule.

More specifically, preferred groups $L^a$ and $G^a$ with specific spacer moieties for $S^0$ are described below.

A preferred structure according to WO-A 2005/099768 is selected from the general formula (I) and (II):

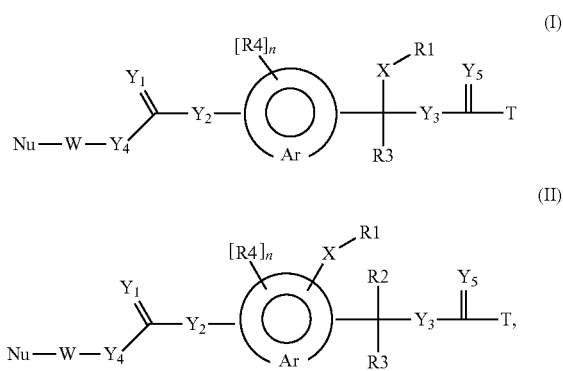

wherein T represents hGH-NH; X represents a spacer moiety; $Y_1$ and $Y_2$ each independently represent O, S or $NR_6$; Y3 represents O or S; $Y_4$ represents O, $NR_6$ or —$C(R_7)(Rs)$; R3 represents a moiety selected from the group consisting of hydrogen, substituted or unsubstituted linear, branched or cyclical alkyl or heteroalkyl groups, aryls, substituted aryls, substituted or unsubstituted heteroaryls, cyano groups, nitro groups, halogens, carboxy groups, carboxyalkyl groups, alkylcarbonyl groups or carboxamidoalkyl groups; $R_4$ represents a moiety selected from the group consisting of hydrogen, substituted or unsubstituted linear, branched or cyclical alkyls or heteroalkyls, aryls, substituted aryls, substituted or unsubstituted heteroaryl, substituted or unsubstituted linear, branched or cyclical alkoxys, substituted or unsubstituted linear, branched or cyclical heteroalkyloxys, aryloxys or heteroaryloxys, cyano groups and halogens; $R_7$ and $R_8$ are each independently selected from the group consisting of hydrogen, substituted or unsubstituted linear, branched or cyclical alkyls or heteroalkyls, aryls, substituted aryls, substituted or unsubstituted heteroaryls, carboxyalkyl groups, alkylcarbonyl groups, carboxamidoalkyl groups, cyano groups, and halogens; $R_6$ represents a group selected from hydrogen, substituted or unsubstituted linear, branched or cyclical alkyls or heteroalkyls, aryls, substituted aryls and substituted or unsubstituted heteroaryls; Ri represents the rest of $S^0$; W represents a group selected from substituted or unsubstituted linear, branched or cyclical alkyls, aryls, substituted aryls, substituted or unsubstituted linear, branched or cyclical heteroalkyls, substituted or unsubstituted heteroaryls; Nu represents a nucleophile; n represents zero or a positive imager; and Ar represents a multi-substituted aromatic hydrocarbon or multi-substituted aromatic heterocycle.

Within the meaning of the present invention, the group $L^a$ is represented by $Y_3$—$C(Y_5)NH$— (together with the amino group of hGH), $G^a$ is represented by Nu-W—$Y_4$—$C(Yi)Y_2$ and $Ar(R_4)_n$—$C(R_3)XRi$ represents $S^0$, which further includes at least $S^1$, $S^2$, $BS^1$ and optionally $BS^2$.

In an alternative embodiment $S^1$ is attached via Ar or represents $R_3$. Then the carbon atom adjacent to $Y_3$ substituted with $XR^1$ represents the branching structure $BS^1$, $S^1$ is terminated with Ar comprising $G^a$. It is evident that in this embodiment terms $S^0$ and $S^1$ are interchangeable.

Preferably, in formula (AA) or (AA1) $S^0$ is of formula (AAA1)

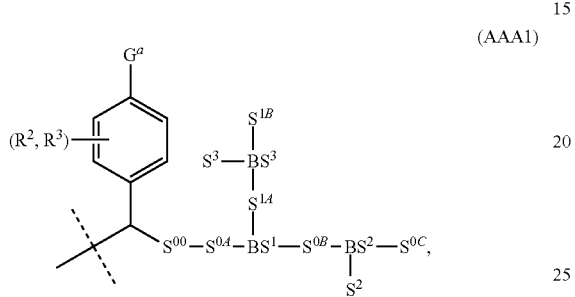
(AAA1)

wherein $G^a$ has the meaning as indicated above;

$S^{00}$ is $CH_2$; or $C(O)$;

$S^{0A}$ is an alkylene chain having from 1 to 20 carbon atoms, which is optionally interrupted or terminated by one or more groups, cycles or heteroatoms selected from the group consisting of optionally substituted heterocycle; O; S; C(O); and NH;

$BS^1$, $BS^2$, $BS^3$ are independently selected from the group consisting of N; and CH.

$S^{0B}$, $S^{1A}$ are independently an alkylene chain having from 1 to 200 carbon atoms, which is optionally interrupted or terminated by one or more groups, cycles or heteroatoms selected from the group consisting of optionally substituted heterocycle; 0; S; C(O); and NH;

$S^{OC}$, $S^{1B}$, are $(C(O))n2(CH2)n1(OCH_2C_{1-12})_n OC_{1-13}$, wherein each n is independently an integer from 100 to 500, each n1 is independently 0, 1, 2, 3, 4, 5, 6, 7, or 8, and n2 is 0 or 1.

$S^2$, $S^3$ are independently hydrogen; or $(C(O))_{n2}(CH_2)_{n1}(OCH_2C_{1-12})_n OC_{1-13}$, wherein each n is independently an integer from 100 to 500, each n1 is independently 0, 1, 2, 3, 4, 5, 6, 7, or 8, and n2 is 0 or 1, provided that at least one of $S^2$, $S^3$ is other than hydrogen;

$R^2$, $R^3$ are defined as for formula (A) below.

The term heterocycle means an heterocycle as defined above. Optional substituents are, e.g. oxo (=O), where the ring is at least partially saturated, a branched or unbranched alkyl chain having from one to 6 carbon atoms, or halogen. A preferred substituted heterocycle is succinimide.

Preferably, $G^a$ in formula (AAA1) is OC(O)—R and R is the partial structure of formula (I) as shown below, wherein R1, R4, R5 and n are defined as given below.

Another preferred embodiment is described in WO06136586A2. Accordingly, the following structures are preferred:

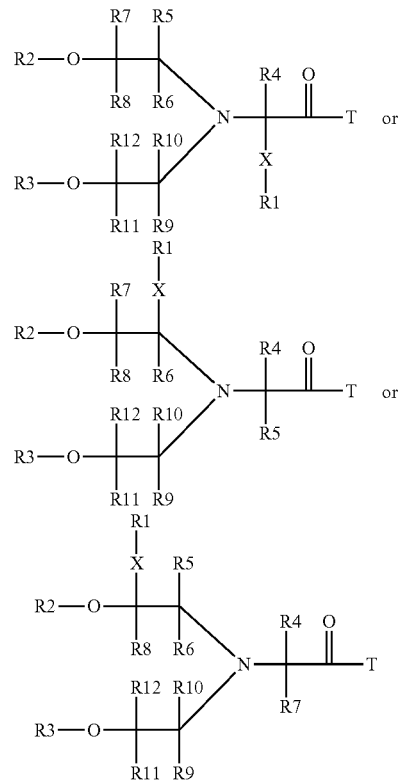

wherein T is NH-hGH;

X is a spacer moiety such as R13-Y1;

Y1 is O, S, NR6, succinimide, maleimide, unsaturated carbon-carbon bonds or any heteroatom containing a free electron pair or is absent;

R13 is selected from substituted or non-substituted linear, branched or cyclical alkyl or heteroalkyl, aryls, substituted aryls, substituted or non-substituted heteroaryls;

R2 and R3 are selected independently from hydrogen, acyl groups, or protecting groups for hydroxyl groups;

R4 to R12 are selected independently from hydrogen, X—R1, substituted or non-substituted linear, branched or cyclical alkyl or heteroalkyl, aryls, substituted aryls, substituted or non-substituted heteroaryls, cyano, nitro, halogen, carboxy, carboxamide;

R1 is the rest of $S^0$, comprising at least $S^1$, $S^2$, $BS^1$, and optionally $BS^2$.

In this embodiment $L^a$ is an amide group, and $G^a$ encompasses the N-branched structure carrying $OR_2/OR_3$.

In yet another preferred embodiment, a preferred structure is given by a prodrug conjugate D-L, wherein D is NH-hGH; and L is a non-biologically active linker moiety -$L^1$ represented by formula (I),

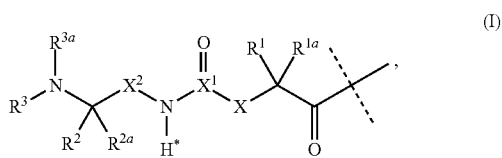
(I)

wherein the dashed line indicates the attachment to the amino group of hGH by forming an amide bond;

X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;

$X^1$ is C; or S(O);

$X^2$ is $C(R^7, R^{7a})$; or $C(R^7, R^{7a})$—$C(R^8, R^{8a})$;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl; or Optionally, one or more of the pairs $R^{1a}/R^{4a}$, $R^{1a}/R^{5a}$, $R^{4a}/R^{5a}$, $R^{4a}/R^{5a}$, $R^{7a}/R^{8a}$ form a chemical bond;

Optionally, one or more of the pairs $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-7}$ cycloalkyl; or 4 to 7 membered heterocyclyl;

Optionally, one or more of the pairs $R^1/R^4$, $RVR^5$, $RVR^6$, $R^4/R^5$, $R^7/R^8$, $R^2/R^3$ are joined together with the atoms to which they are attached to form a ring A;

Optionally, $R^3/R^{3a}$ are joined together with the nitrogen atom to which they are attached to form a 4 to 7 membered heterocycle;

A is selected from the group consisting of phenyl; naphthyl; indenyl; indanyl; tetralinyl; C3-10 cycloalkyl; 4 to 7 membered heterocyclyl; and 9 to 11 membered heterobicyclyl; and wherein $L^1$ is substituted with one group $L^2$-Z and optionally further substituted, provided that the hydrogen marked with the asterisk in formula (I) is not replaced by a substituent; wherein $L^2$ is a single chemical bond or a spacer; and Z is the rest of $S^0$, comprising at least $S^1$, $S^2$, $BS^1$, and optionally $BS^2$.

In this embodiment $L^a$ is represented by an amide group and $G^a$ is represented by $N(H')X^1(O)$ and the chain connecting to N including substituents of N.

Prodrug conjugates of this type are described in European Patent application No 08150973.9

Accordingly, a composition of the present invention is preferred, wherein $L^a$-$S^o$ is represented by formula (AAA2),

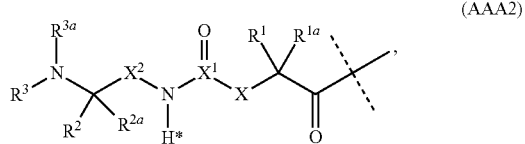

(AAA2)

wherein the dashed line indicates the attachment to the primary amino group of hGH so that $L^a$ and the amino group form an amide bond;

X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;

$X^1$ is C; o r S(O);

$X^2$ is $C(R^7, R^{7a})$; or $C(R^7, R^{7a})$—$C(R^8, R^{8a})$;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl; or Optionally, one or more of the pairs $R^{1a}/R^{4a}$, $R^{1a}/R^{5a}$, $R^{4a}/R^{5a}$, $R^{4a}/R^{5a}$, $R^{7a}/R^{8a}$ form a chemical bond;

Optionally, one or more of the pairs $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-7}$ cycloalkyl; or 4 to 7 membered heterocyclyl;

Optionally, one or more of the pairs $R^1/R^4$, $RVR^5$, $RVR^6$, $R^4/R^5$, $R^7/R^8$, $R^2/R^3$ are joined together with the atoms to which they are attached to form a ring A;

Optionally, $R^3/R^{3a}$ are joined together with the nitrogen atom to which they are attached to form a 4 to 7 membered heterocycle;

A is selected from the group consisting of phenyl; naphthyl; indenyl; indanyl; tetralinyl; $C_{3-10}$ cycloalkyl; 4 to 7 membered heterocyclyl; and 9 to 11 membered heterobicyclyl; and wherein $S^0$ is substituted with one group $L^2$-Z and optionally further substituted, provided that the hydrogen marked with the asterisk in formula (I) is not replaced by a substituent; wherein $L^2$ is a single chemical bond or a spacer; and Z is of formula (AAA2a)

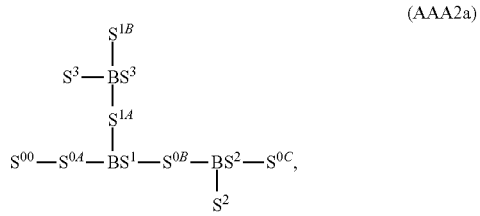

(AAA2a)

wherein $S^{00}$, $S^{0A}$, $S^{0B}$, $S^{0C}$, $S^{1A}$, $S^{1B}$, $S^2$, $S^3$, $BS^1$, $BS^2$, and $BS^3$ have the meaning as indicated for formula (AAA1) above.

"Alkyl" means a straight-chain or branched carbon chain. Each hydrogen of an alkyl carbon may be replaced by a substituent.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent.

Accordingly, "$C_{M\,S}$ alkyl" means an alkyl chain having 1 to 18 carbon atoms and "Cβ is alkyl" means an alkyl chain having 8 to 18 carbon atoms. Accordingly, "$C_{1-50}$ alkyl" means an alkyl chain having 1 to 50 carbon atoms.

"$C_{2-50}$ alkenyl" means a branched or unbranched alkenyl chain having 2 to 50 carbon atoms, e.g. if present at the end of a molecule: —CH=$CH_2$, —CH=CH—$CH_3$, —$CH_2$—CH=$CH_2$, —CH=CH—$CH_2$—$CH_3$, —CH=CH—CH=$CH_2$, or e.g. —CH=CH—, when two moieties of a molecule are linked by the alkenyl group. Each hydrogen of a $C_{2-5}$ Oalkenyl carbon may be replaced by a substituent as further specified. Accordingly, the term "alkenyl" relates to a carbon chain with at least one carbon carbon double bond. Optionally, one or more triple bonds may occur.

"$C_{2-50}$ alkynyl" means a branched or unbranched alkynyl chain having 2 to 50 carbon atoms, e.g. if present at the end of a molecule: —C≡CH, —$CH_2$—C≡CH, $CH_2$—$CH_2$—

O=CH, CH$_2$—O=C—CH$_3$, or e.g. —C=C— when two moieties of a molecule are linked by the alkynyl group. Each hydrogen of a C$_{2-50}$ alkynyl carbon may be replaced by a substituent as further specified. Accordingly, the term "alkynyl" relates to a carbon chain with at least one carbon carbon triple bond. Optionally, one or more double bonds may occur.

"C$_{3-7}$ cycloalkyl" or "C$_{3-7}$ cycloalkyl ring" means a cyclic alkyl chain having 3 to 7 carbon atoms, which may have carbon-carbon double bonds being at least partially saturated, e.g. cyclopropyl, cyclobutyl, cyclopentyl, cyclohexyl, cyclohexenyl, cycloheptyl. Each hydrogen of a cycloalkyl carbon may be replaced by a substituent. The term "C$_{3-7}$ cycloalkyl" or "C$_{3-7}$ cycloalkyl ring" also includes bridged bicycles like norbonane or norbornene. Accordingly, "C$_{3-5}$ cycloalkyl" means a cycloalkyl having 3 to 5 carbon atoms.

Accordingly, "C$_{3-10}$ cycloalkyl" means a cyclic alkyl having 3 to 10 carbon atoms, e.g. C$_{3-7}$ cycloalkyl; cyclopropyl, cyclobutyl, cyclopentyl, cyclohexyl, cyclohexenyl, cycloheptyl, cyclooctyl, cyclononyl, cyclodecyl. The term "C$_{3-10}$cycloalkyl" also includes at least partially saturated carbomono- and -bicycles.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane.

Preferably, L$^a$-S$^o$ is selected from the group consisting of

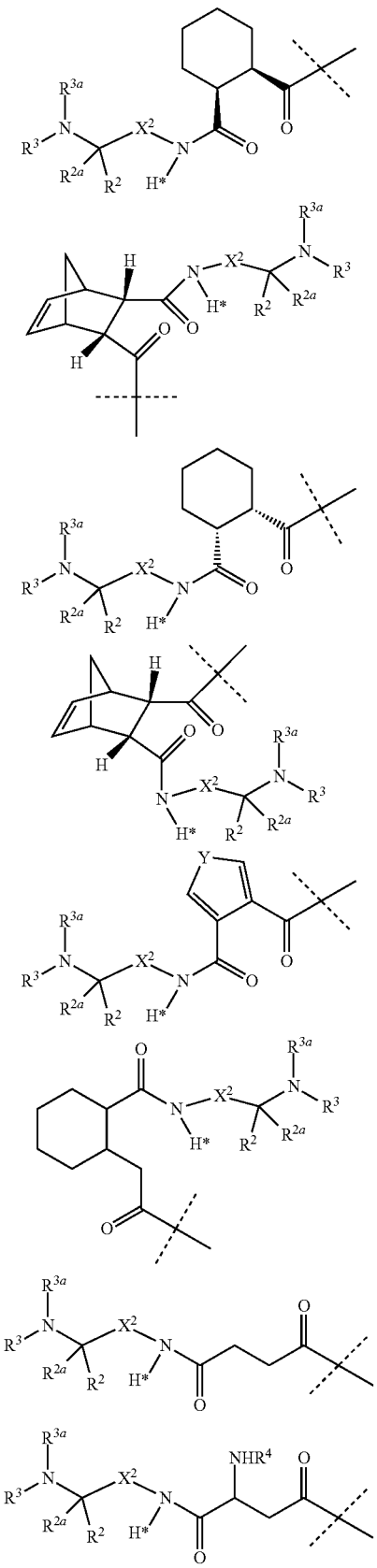

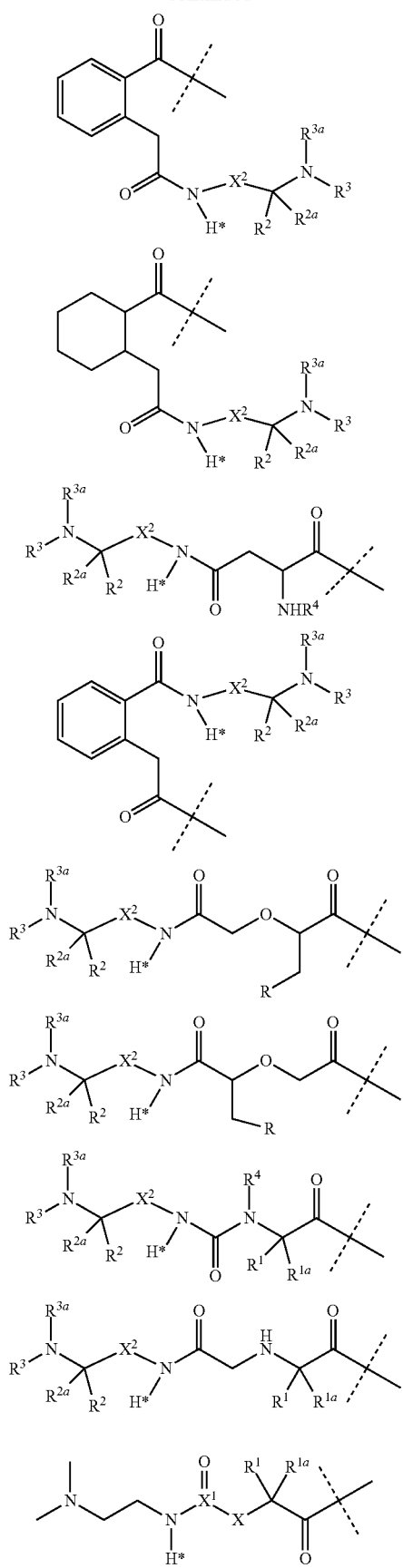
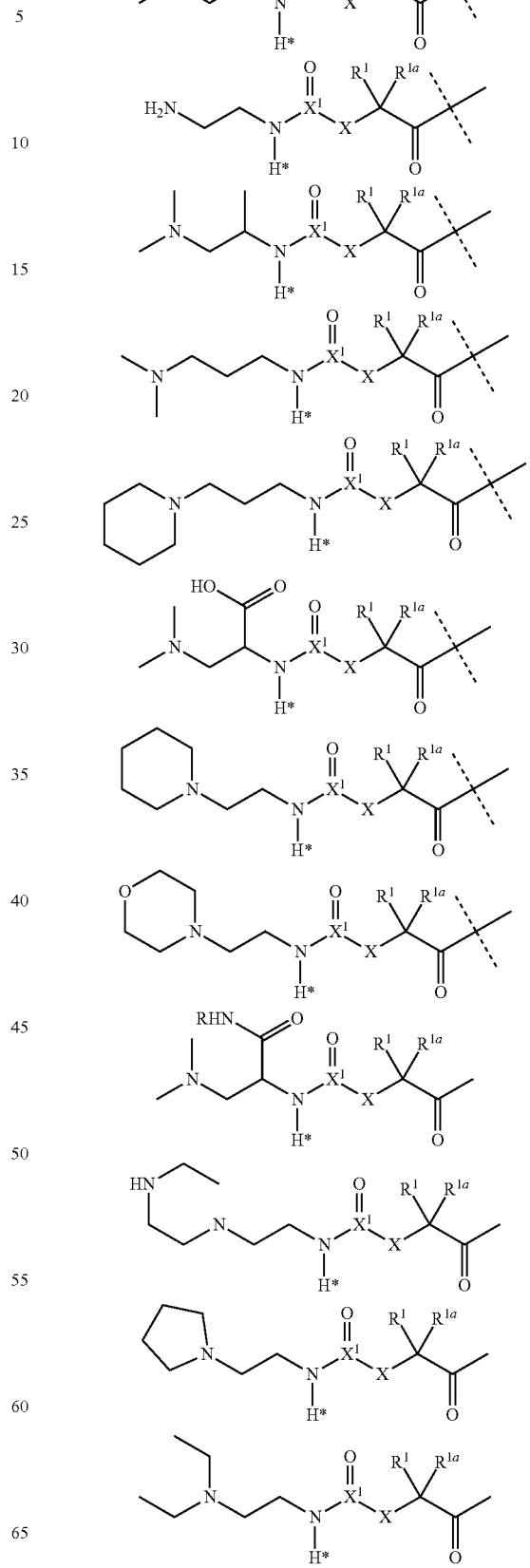

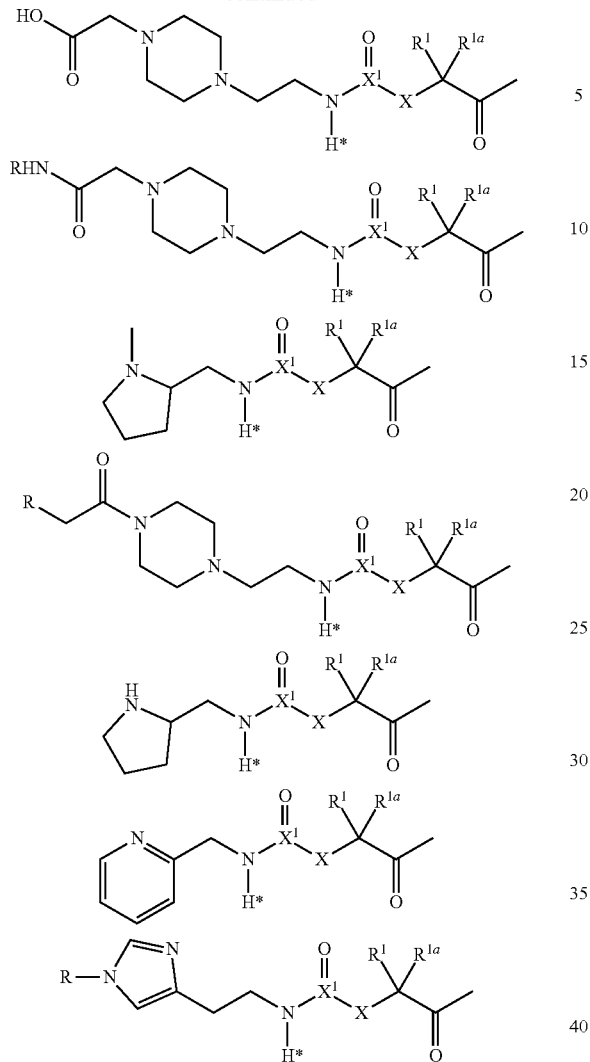
wherein R is H; or $C_{1-4}$ alkyl; Y is NH; O; or S; and $R^1$, $R^{1a}$, $R^2$, $R^{2a}$, $R^3$, $R^{3a}$, $R^4$, X, $X^1$, $X^2$ have the meaning as indicated above.
Even more preferred, $L^a$-$S^0$ is selected from the group consisting of
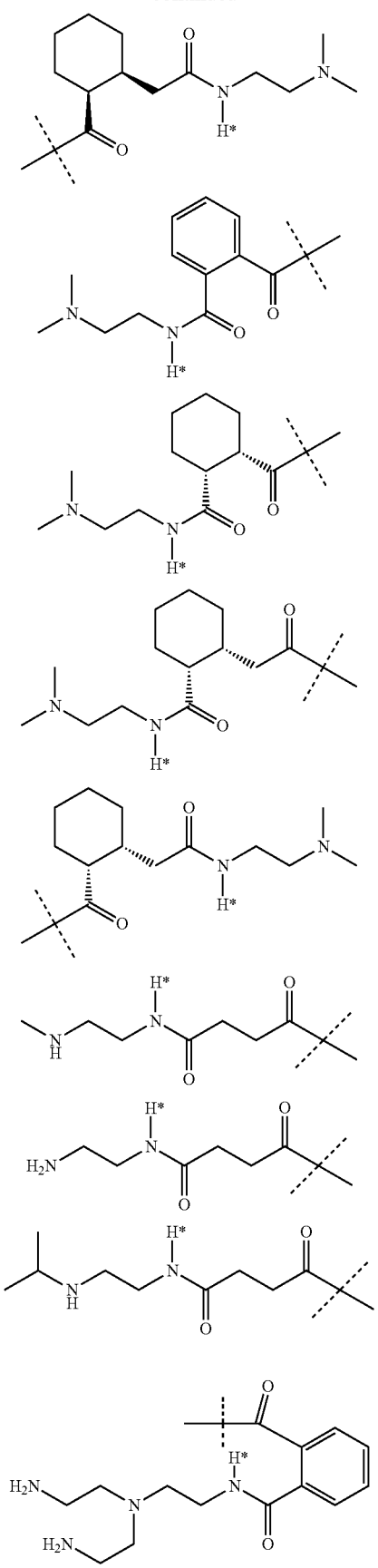

33
-continued
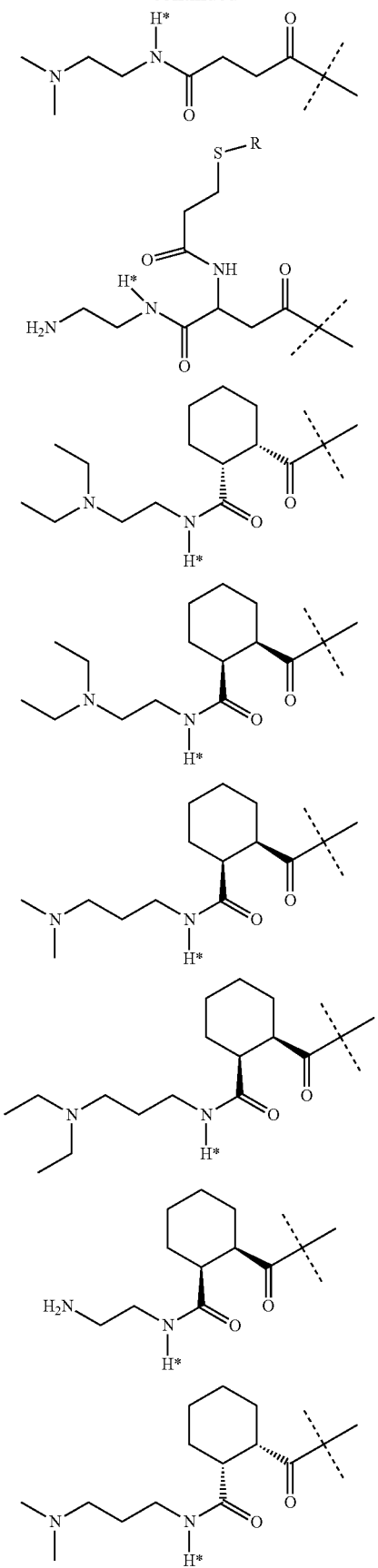
34
-continued
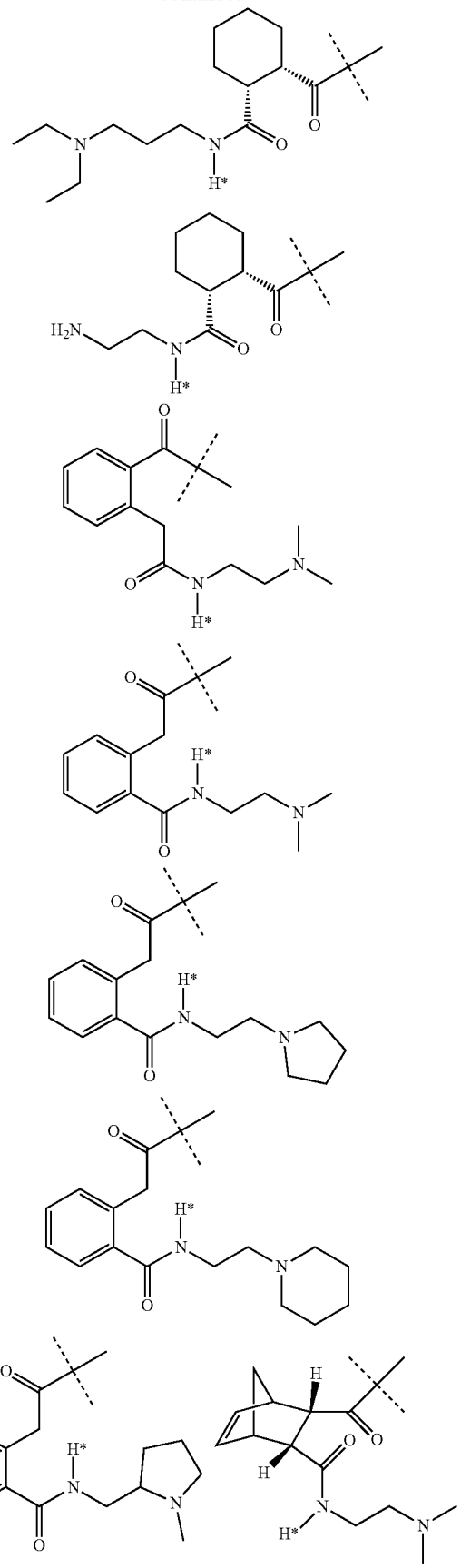

35
-continued
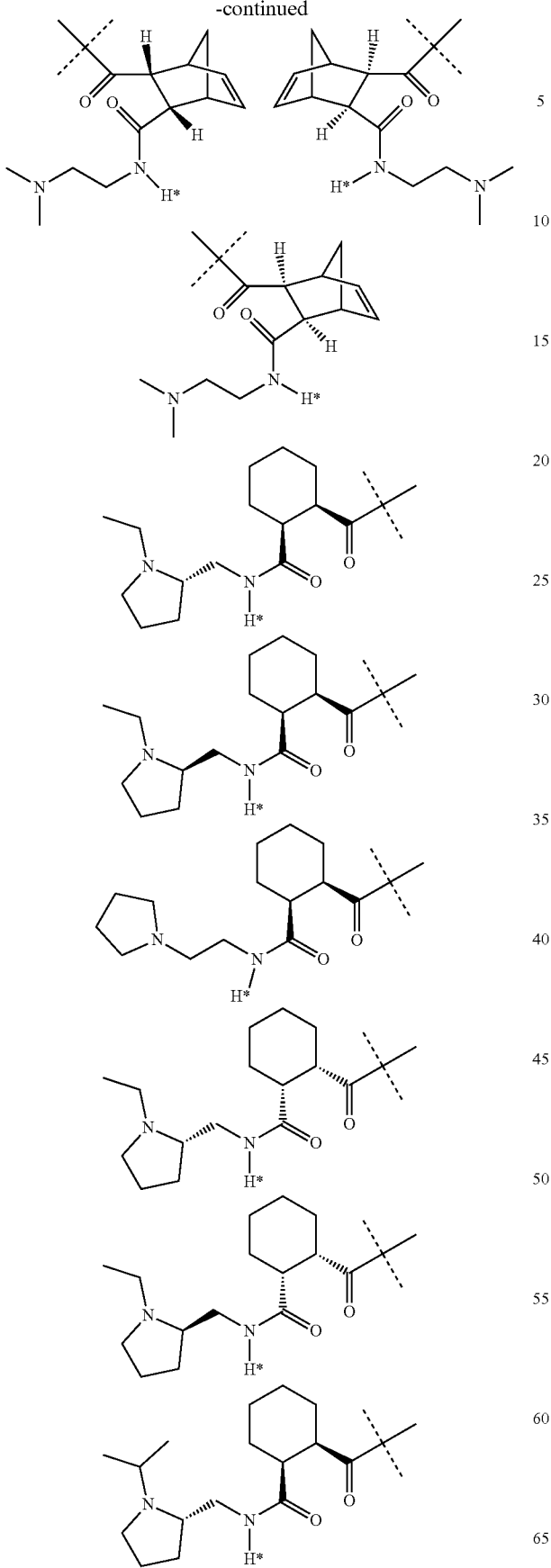
36
-continued
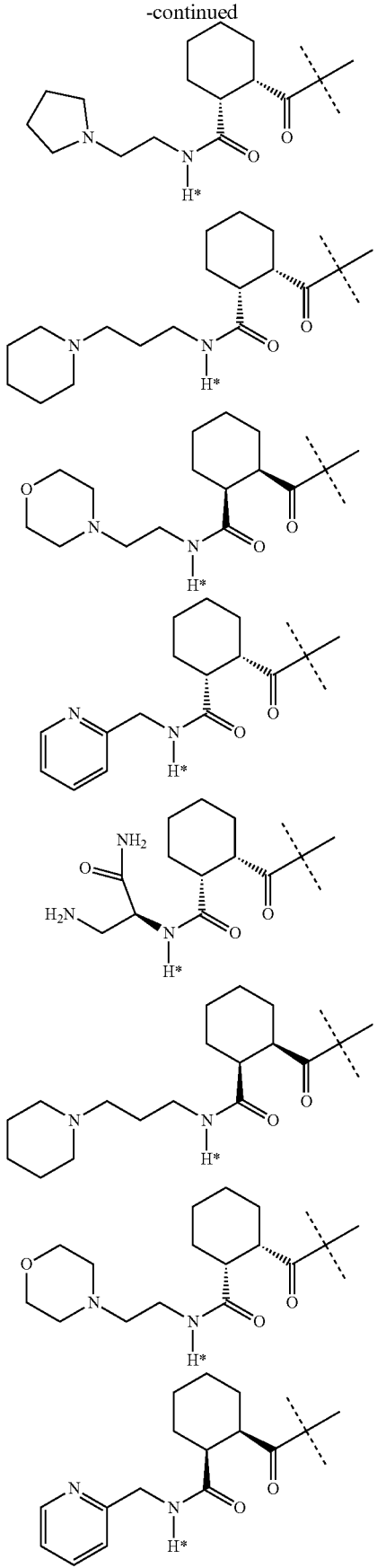

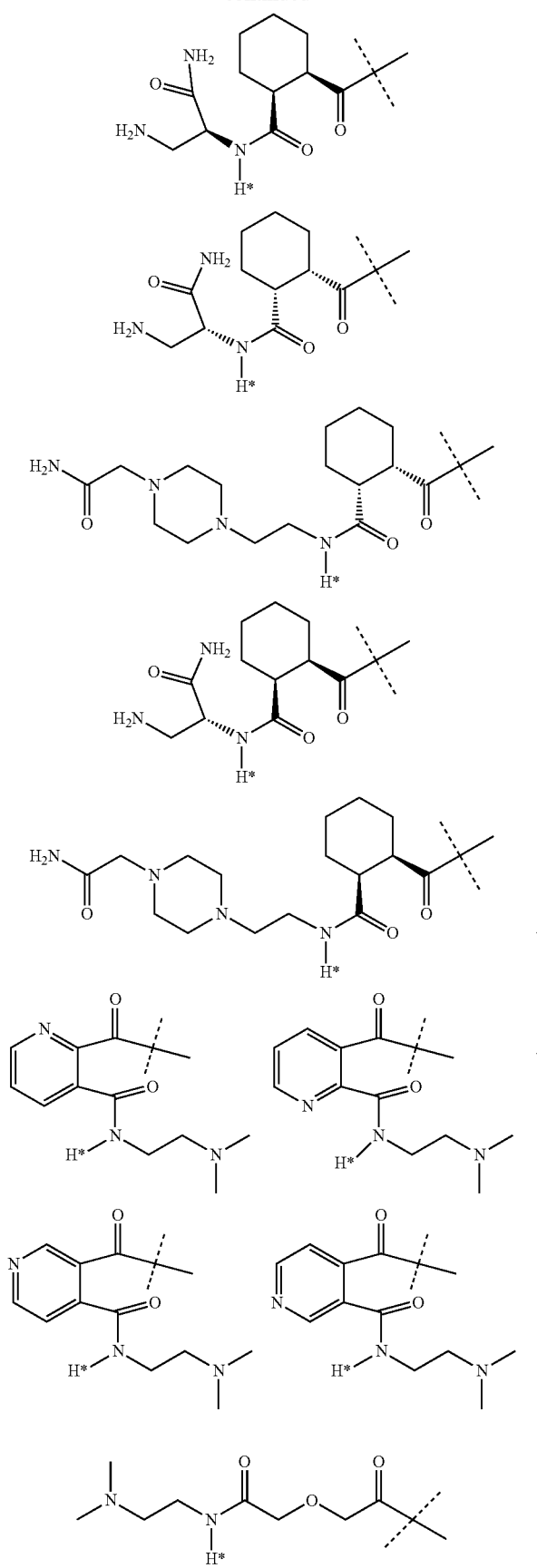
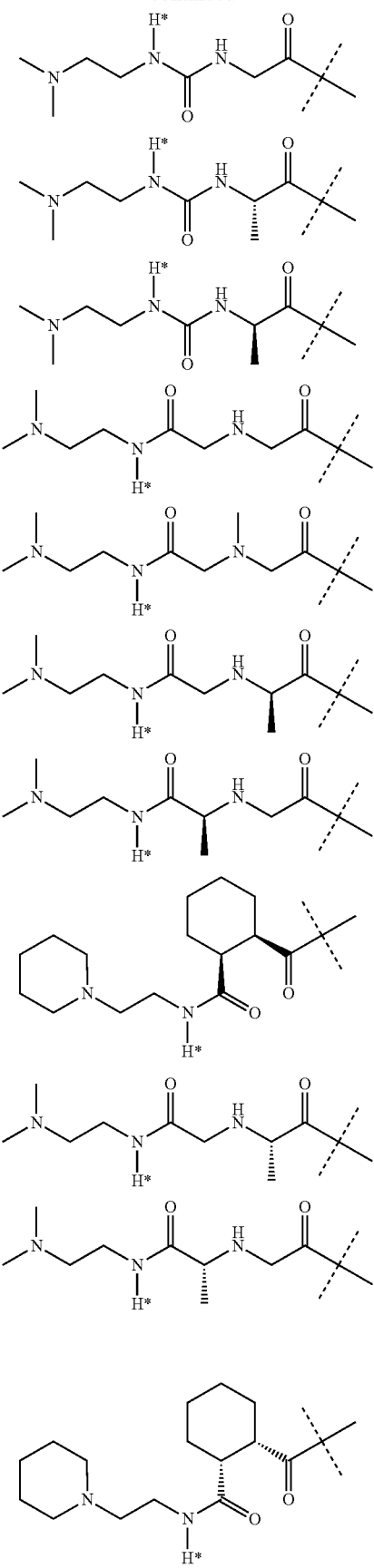

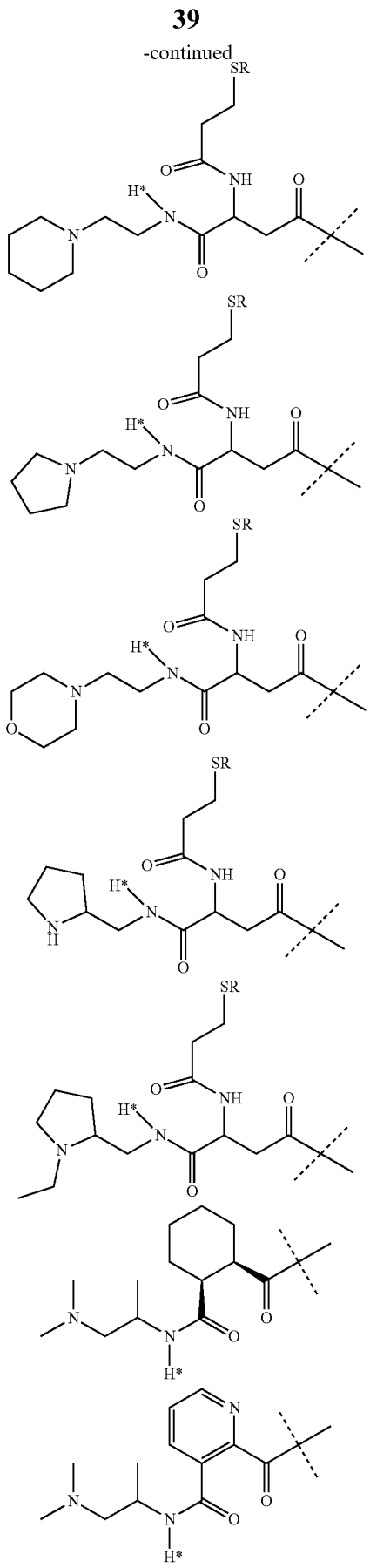
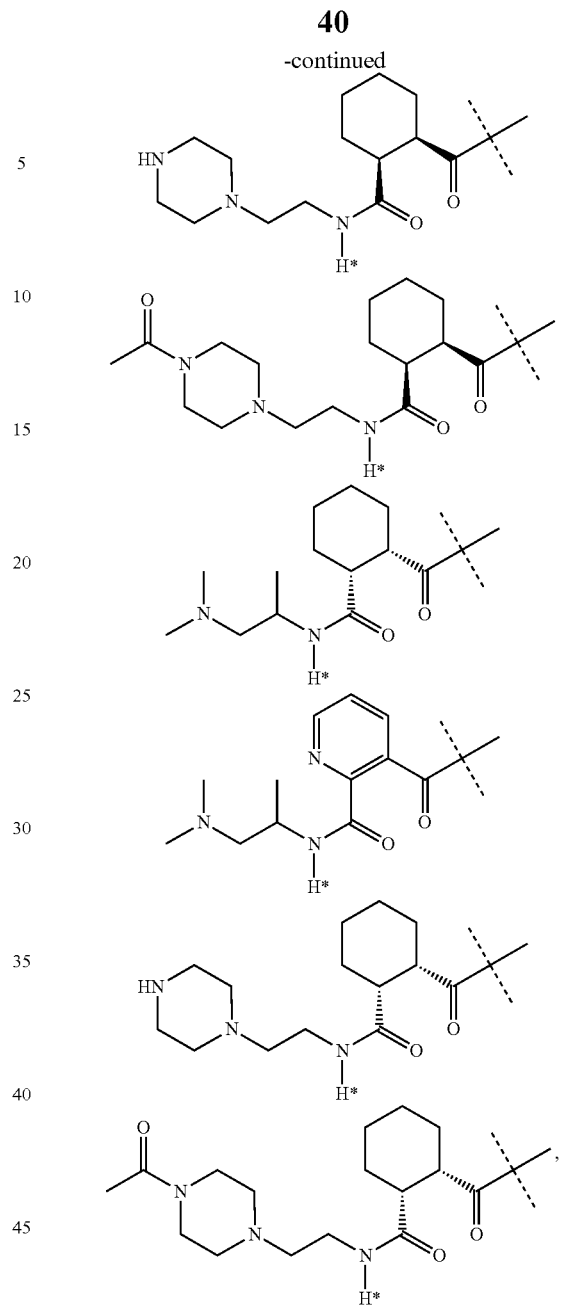

wherein R has the meaning as indicated above.

At least one (up to four) hydrogen is replaced by a group $L^2$-Z. In case more than one group $L^2$-Z is present each $L^2$ and each Z can be selected independently. Preferably, only one group $L^2$-Z is present.

In general, $S^0$ can be substituted with $L^2$-Z at any position apart from the replacement of the hydrogen marked with an asterisk in the formulae above. Preferably, one to four of the hydrogen given by R, $R^1$ to $R^8$ directly or as hydrogen of the $C_{1-4}$ alkyl or further groups and rings given by the definition of R and $R^1$ to $R^{8a}$ are replaced by $L^2$. Z.

Furthermore, $S^0$ may be optionally further substituted. In general, any substituent may be used as far as the cleavage principle is not affected.

Preferably, one or more further optional substituents are independently selected from the group consisting of halogen; ON; $COOR^9$; $OR^9$; $C(O)R^9$; $C(O)N(R^9R^{9a})$; $S(O)_2N(R^9R^9)$; $S(O)N(R^9R^{93})$; $S(O)_2R^9$; $S(O)R^9$; $N(R^9)S(O)N$ ($R^{9a}R^{9b}$); $SR^9$; $N(R^9R^{93})$; $NO_2$; $OC(O)R^9$; $N(R^9)C(O)R^{9a}$; $N(R^9)S(O)_2R^{9a}$; $N(R^9)S(O)R^{9a}$; $N(R^9)C(O)OR^{9a}$; $N(R^9)C(O)N(R^{9a}R^{9b})$; $OC(O)N(R^9R^{9a})$; T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$); —S(O)N($R^{11}$)—; —S(O)$_2$—; —S(O)—; —N($R^{11}$)S(O)$_2$N($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{113}$);

$R^9$, $R^{9a}$, $R^{9b}$ are independently selected from the group consisting of H; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; $N(R^{11}$)S(O)$_2$N($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{113}$);

T is selected from the group consisting of phenyl; naphthyl; indenyl; indanyl; tetralinyl; $C_{3-10}$ cycloalkyl; 4 to 7 membered heterocyclyl; or 9 to 11 membered heterobicyclyl, wherein T is optionally substituted with one or more $R^{10}$, which are the same or different;

$R^{10}$ is halogen; CN; oxo (=O); $COOR^{12}$; $OR^{12}$; $C(O)R^{12}$; $C(O)N(R^{12}R^{123})$; $S(O)_2N(R^{12}R^{123})$; $S(O)N(R^{12}R^{123})$; $S(O)_2R^{12}$; $S(O)R^{12}$; $N(R^{12})S(O)_2N(R^{12a}R^{12b})$; $SR^{12}$; $N(R^{12}R^{123})$; $NO_2$; $OC(O)R^{12}$; $N(R^{12})C(O)R^{12a}$; $N(R^{12})S(O)_2R^{12a}$; $N(R^{12})S(O)R^{12a}$; $N(R^{12})C(O)OR^{12a}$; $N(R^{12})C(O)N(R^{12a}R^{12b})$; $OC(O)N(R^{12}R^{123})$; or $C_{1-6}$ alkyl, wherein $C_{1-6}$ alkyl is optionally substituted with one or more halogen, which are the same or different;

$R^{11}$, $R^{11a}$, $R^{12}$, $R^{12a}$, $R^{12b}$ are independently selected from the group consisting of H; or $C_{1-6}$ alkyl, wherein $C_{1-6}$ alkyl is optionally substituted with one or more halogen, which are the same or different.

The term "interrupted" means that between two carbons a group is inserted or at the end of the carbon chain between the carbon and hydrogen.

$L^2$ is a single chemical bond or a spacer. In case $L^2$ is a spacer, it is preferably defined as the one or more optional substituents defined above, provided that $L^2$ is substituted with Z.

Accordingly, when $L^2$ is other than a single chemical bond, $L^2$-Z is $COOR^9$; $OR^9$; $C(O)R^9$; $C(O)N(R^9R^{9a})$; $S(O)_2N(R^9R^{9a})$; $S(O)N(R^9R^{93})$; $S(O)_2R^9$; $S(O)R^9$; $N(R^9)S(O)_2N(R^{9a}R^{9b})$; $SR^9$; $N(R^9R^{93})$; $OC(O)R^9$; $N(R^9)C(O)R^{9a}$; $N(R^9)S(O)_2R^{9a}$; $N(R^9)S(O)R^{9a}$; $N(R^9)C(O)OR^{9a}$; $N(R^9)C(O)N(R^{9a}R^{9b})$; $OC(O)N(R^9R^{9a})$; T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of -T-, —C(O)O—; —O—; —C(O)—; —C(O)N($R^{11}$)—; —S(O)$_2$N($R^{11}$)—; —S(O)N($R^{11}$)S(O)$_2$—; —S(O)—; —N($R^{11}$)S(O)$_2$N($R^{113}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{113}$)—; and —OC(O)N($R^{11}R^{113}$);

$R^9$, $R^{9a}$, $R^{9b}$ are independently selected from the group consisting of H; Z; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$)—; —S(O)N($R^{11}$)S(O)$_2$—; —S(O)—; —N($R^{11}$)S(O)$_2$N($R^{113}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{113}$)—; and —OC(O)N($R^{11}R^{113}$);

T is selected from the group consisting of phenyl; naphthyl; indenyl; indanyl; tetralinyl; $C_{3-10}$ cycloalkyl; 4 to 7 membered heterocyclyl; or 9 to 11 membered heterobicyclyl, wherein t is optionally substituted with one or more $R^{10}$, which are the same or different;

$R^{10}$ is Z; halogen; CN; oxo (=O); $COOR^{12}$; $OR^{12}$; $C(O)R^{12}$; $C(O)N(R^{12}R^{123})$; $S(O)_2N(R^{12}R^{123})$; $S(O)N(R^{12}R^{123})$; $S(O)_2R^{12}$; $S(O)R^{12}$; $N(R^{12})S(O)_2N(R^{12a}R^{12b})$; $SR^{12}$; $N(R^{12}R^{123})$; $NO_2$; $OC(O)R^{12}$; $N(R^{12})C(O)R^{12a}$; $N(R^{12})S(O)_2R^{12a}$; $N(R^{12})S(O)R^{12a}$; $N(R^{12})C(O)OR^{12a}$; $N(R^{12})C(O)N(R^{12a}R^{12b})$; $OC(O)N(R^{12}R^{123})$; or $C_{1-6}$ alkyl, wherein $C_{1-6}$ alkyl is optionally substituted with one or more halogen, which are the same or different;

$R^{11}$, $R^{11a}$, $R^{12}$, $R^{12a}$, $R^{12b}$ are independently selected from the group consisting of H; Z; or C1-6 alkyl, wherein $C_{1-6}$ alkyl is optionally substituted with one or more halogen, which are the same or different;

provided that one of $R^ä$, $R^{äa}$, $R^{äD}$, $R^{nü}$, $R^{ii}$, $R^{nña}$, $R^{i2}$, $R^{n2a}$, $R^{n2D}$ is Z.

Even more preferred general aromatic structures are listed below.

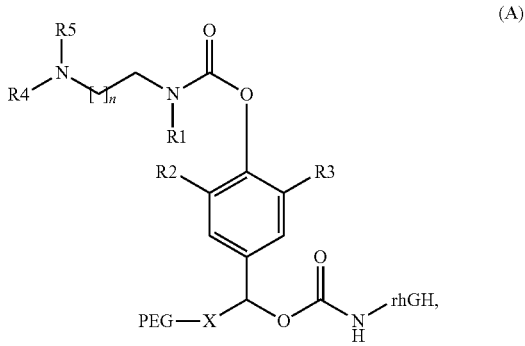

(A)

wherein

NH-rhGH represents the rhGH residue attached to the transient linker;

R1, R2, R3, R4, and R5 are selected independently from hydrogen, methyl, ethyl, propyl, isopropyl, butyl, isobutyl, tertiary butyl, PEG represents the PEGylation residue attached to the transient linker, and n=1 or 2, and X is selected from C1 to C8 alkyl or C1 to C12 heteroalkyl.

The term "C1 to C12 heteroalkyl" means an alkyl chain having 1 to 12 carbon atoms which are optionally interrupted by heteroatoms, functional groups, carbocycles or heterocycles as defined above.

In a preferred embodiment, in formula (A) $L^a$ is represented by the carbamate group attached to rhGH, $G^a$ is represented by the aromatic oxygen group, the carbonyl attached to it, and the substituent attached to the carbonyl as shown in formula i.

More preferred structures are given by general formula i, which are part of the structure (A) within the general aromatic linker structure above:

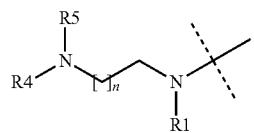

Formula I and where preferred examples of formula I comprise:

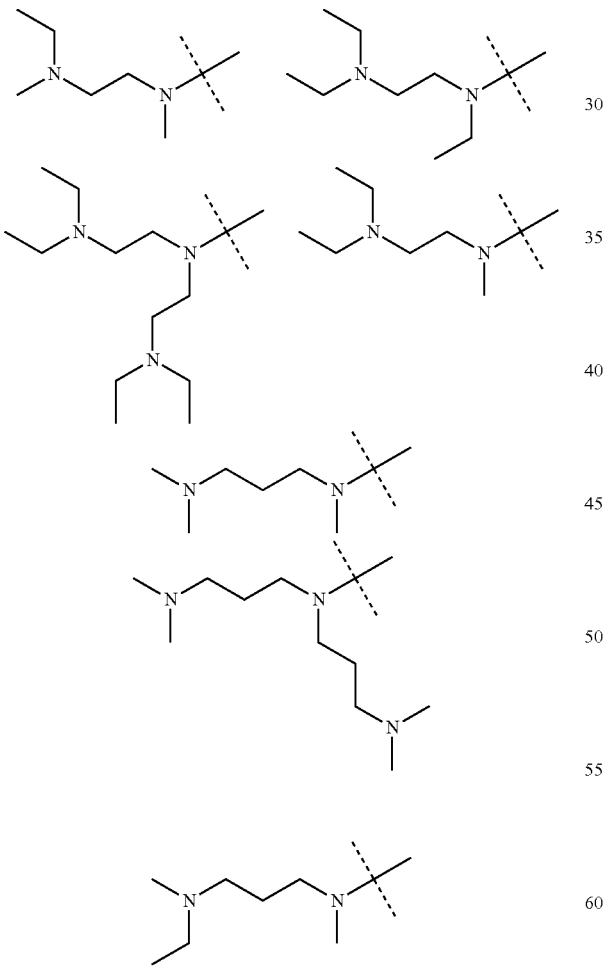

More preferred aromatic structures of formula II, which are part of the structure (A) within the general aromatic linker structure above:

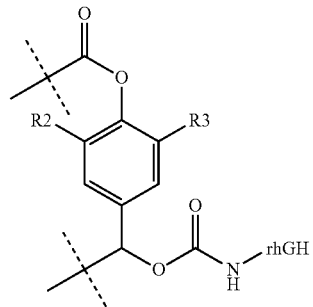

Formula II and where preferred examples of formula n comprise:

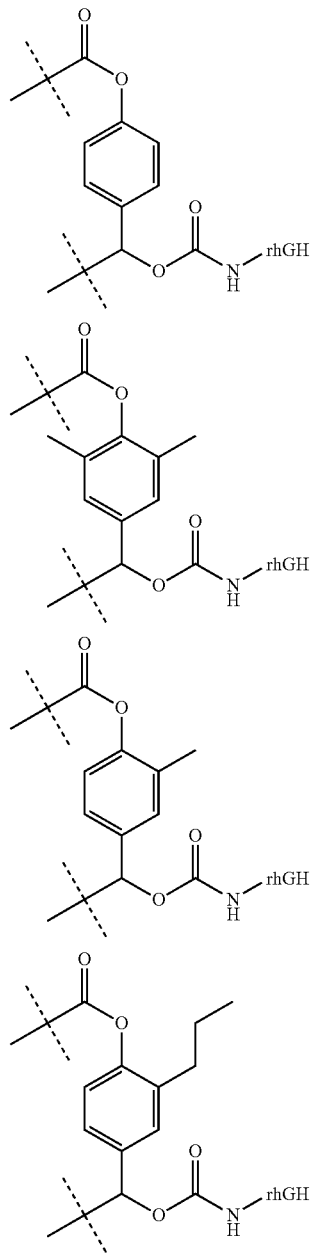

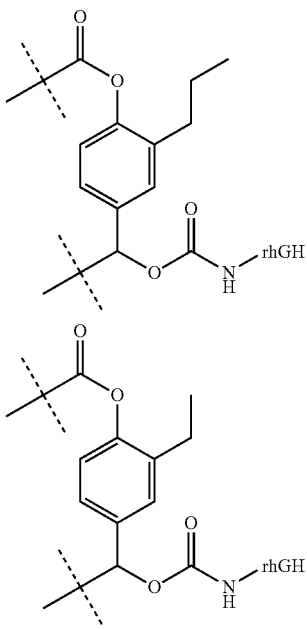

More preferred structures of formula III, which are part of the structure (A) within the general aromatic linker structure above, wherein PEG-X is $$PEG—W^X$$

and PEG-W includes the following substituent groups:

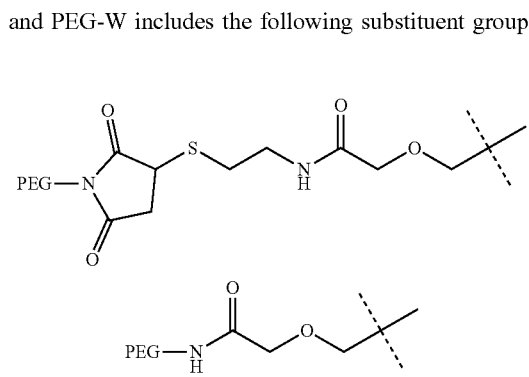

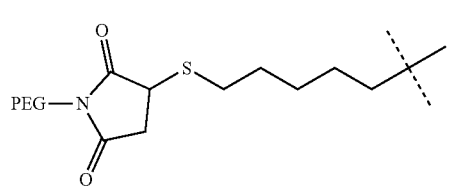

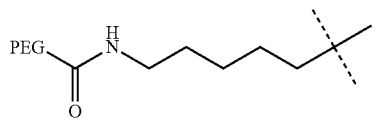

One example of preferred prodrug conjugates are shown below:

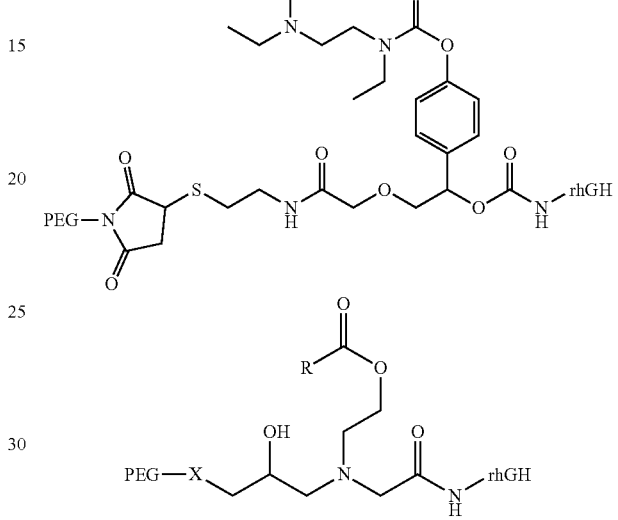

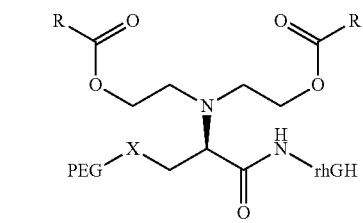

R is selected from hydrogen, methyl, ethyl, propyl and butyl,

X is selected from C1 to C8 alkyl or C1 to C12 heteroalkyl.

Also in the preferred and more preferred embodiments PEG means preferably the rest of $S^o$, (comprising at least $S^1$, $S^2$, $BS^1$ and optionally $BS^2$.

In a preferred embodiment prodrugs of the present invention are selected from the group consisting of
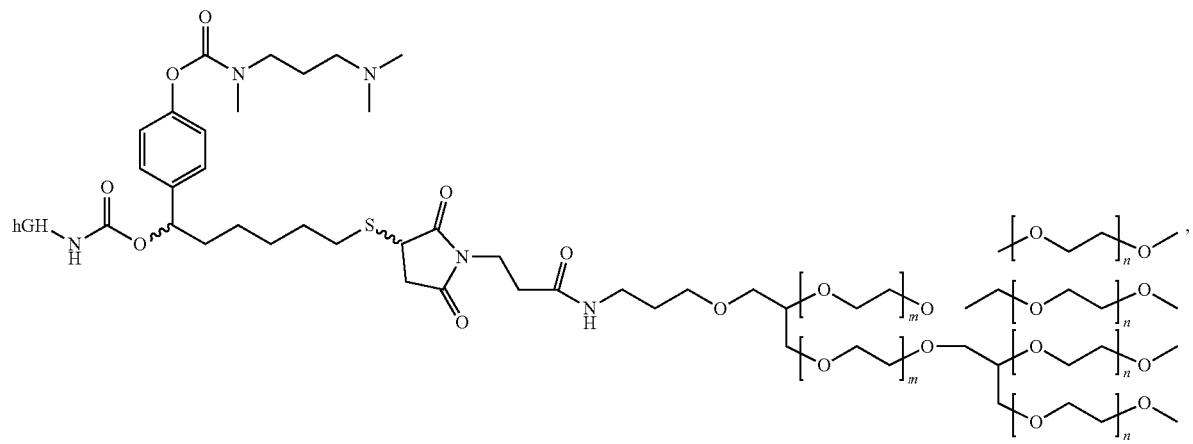
35
wherein m is an integer from 200 to 250 and n is an integer from 100 to 125;
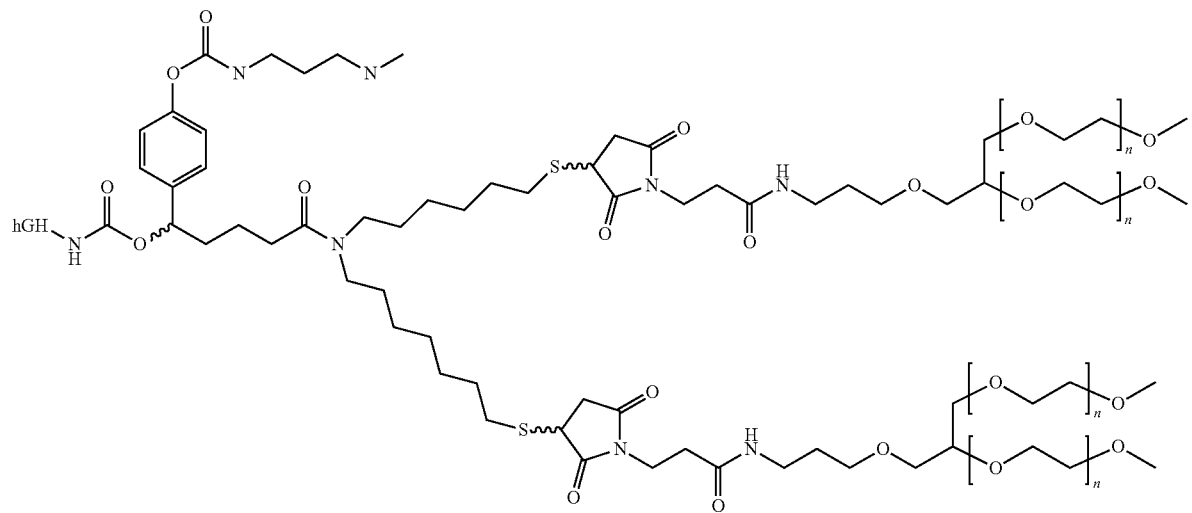
36 wherein n is an integer from 400 to 500;

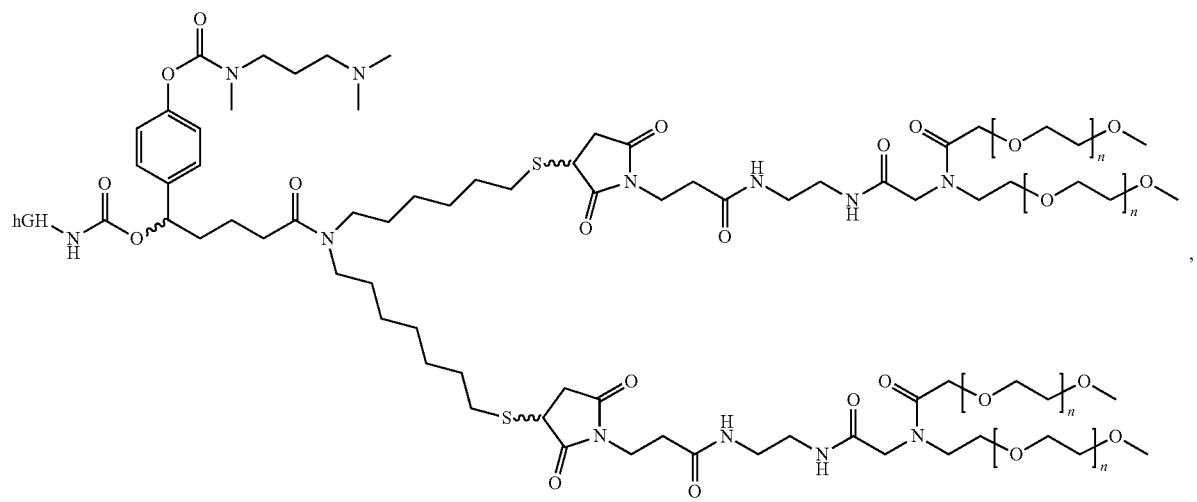

wherein n is an integer from 400 to 500; and

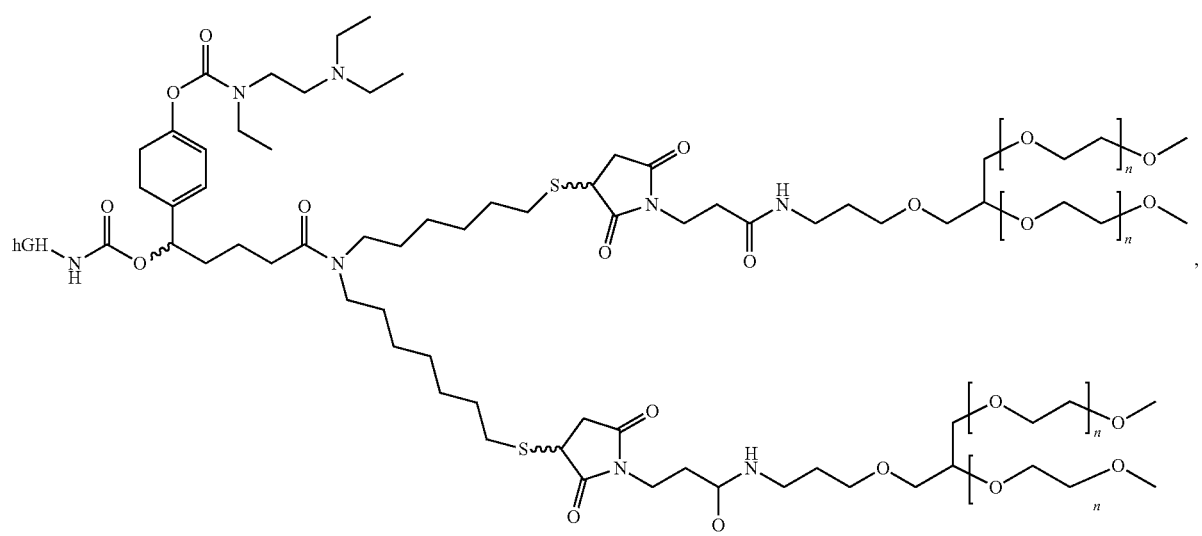

wherein n is an integer from 400 to 500.

Prodrugs of the present invention can be prepared by methods known in the art. However especially for compounds of formula (AA1) it is preferred to build up the prodrug molecule in a convergent synthesis by providing a first precursor molecule comprising one or more thiol groups and an activated carbonate group and a second precursor molecule comprising a maleimide group to react in an addition reaction resulting in the formation of a thio succinimide group and to react that combined precursor molecule with hGH to yield a compound of formula (AA1).

Accordingly, another aspect of the present invention is a method for the preparation of a compound of formula hGH-NH—C(O)O—S⁰ (AA1), wherein S⁰ has the meaning as indicated above and comprises at least one group

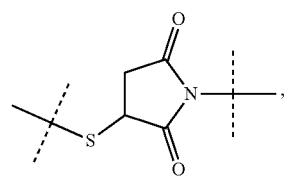

the method comprises the following steps:
(a) reacting a compound of formula ROC(O)O—S$^{0'}$—SH (AA1') with a compound of formula

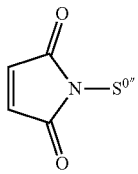

(AA2'), wherein R is a suitable rest for an activated carbonate group and wherein S$^{0'}$ and S$^{0'''}$ are selected to yield S$^0$ comprising the at least one group

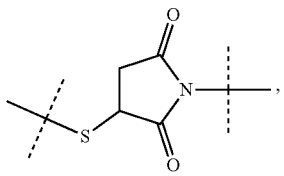

resulting in a compound of formula ROC(O)O—S$^0$, and (b) reacting the compound of formula ROC(O)O—S$^0$ with hGH-NH$_2$, wherein hGH-NH$_2$ represents hGH with one of its primary amino groups to yield a compound of formula (AA1).

Suitable R groups for the carbonate functional groups include substituted alkyl or carbocyclic or heterocyclic, like aryl or cycloalkyl, groups like the pentafluorophenyl or NHS group.

Assays to Determine the Functional Properties of rhGH PEGylated Prodrug

Activity and Half Life of the Conjugate

To determine the activity and the half life of the prodrug conjugate described herein, it is necessary to synthesize a "permanent" conjugate, which does not undergo autohydrolysis—that is a permanent conjugate.

This is achieved by synthesizing a molecule identical to the rhGH PEGylated prodrug, apart from modifying the part of the linker structure, which initiates the autocleavage. Such corresponding compound will have residual activity and circulating half-life of the conjugate identical to that of the rhGH PEGylated prodrug. More generally, for any self hydrolysable (autocleavage) transient linker conjugated prodrugs it can be envisioned to synthesize a molecule identical to the prodrug, apart for the ability to undergo autocleavage, by making minor modification to the linker structure.

The reason for using the corresponding conjugate is that if the self hydrolysable (autocleavage) transient linker as described herein is applied in the assay mentioned in Example 1, the conjugate will obviously immediately begin to release unmodified drug, which will influence assay results. In other words, it is not possible to measure residual activity without preparing a permanent conjugate as the unchanged native drug e.g. rhGH, will be released and contribute to the measured activity. This is obvious to the skilled person.

For this reason as explained above the residual activity of the self hydrolysable (autocleavage) transient linker conjugated prodrugs are expressed as the activity of the corresponding permanent conjugates. The permanent conjugates are prepared in a similar fashion to the self hydrolysable (autocleavage) transient linker conjugated prodrugs (examples 20 through 23), but with a minor modification in the linker structure, so that the linker no longer can undergo autocleavage. The preparation of permanent conjugates is described in Example 10 through Example 19.

According to one embodiment of the present invention rhGH PEGylated prodrug as described herein is characterized by that:
(1): when PEG is linked to rhGH in the prodrug conjugate the prodrug has an GH activity with is less than 5% of the native growth hormone without PEG to avoid injection side lipoatrophy; and
(2): PEG is linked to rhGH via a self hydrolysable (autocleavage) transient linker, wherein the linker autohydrolysis rate is such that the in vivo half-life is from 10 hours to 600 hours.

The assay to determine property (1) is described in detail in working example 1 herein. Based on these detailed instructions it is routine work for the skilled person to measure this residual activity of the prodrug.

In a preferred embodiment the residual activity of property (1) is less than 5%, more preferably less than 3%, even more preferably less than 1% and most preferably virtually inactive.

The assay to determine property (2) is described in detail in working example 2 herein. Based on these detailed instructions it is routine work for the skilled person to measure this autocleavage rate of the transient linker of the prodrug.

In a preferred embodiment the autocleavage rate in vivo half-life is such that the in vivo half-life is from 20 hours to 300 hours, more preferably from 20 hours to 150 hours, even more preferably from 30 hours to 150 hours, even more preferably from 30 hours to 100 hours, even more preferably from 40 hours to 100 hours even more preferably from 50 to 75 hours and also even more preferably from 30 to 75 hours.

In Vivo and In Vitro Correlation

It is known from previous patent applications from the company Ascendis Pharma (Complex Biosystems Company) that there is good correlation between in vitro and in vivo linker cleavage rates. In vivo release kinetics can be readily predicted from the in vitro experimental data.

Lipoatrophy

As described above lipoatrophy is lipolysis occurring in close proximity of the injection site. Therefore, measuring in vitro lipolysis of growth hormone and growth hormone conjugates can be used to estimate the lipoatrophy effect of the conjugates.

To determine the lipolytic effect of the prodrug conjugate described herein, it is necessary to synthesize a "permanent" conjugate, which does not undergo autohydrolysis—that is a permanent conjugate.

The assay to determine lipoatrophy is described in details in working example 3 herein. Based on these detailed instructions it is routine work for the skilled person to measure lipoatrophy.

In a preferred embodiment, the rhGH PEGylated prodrug conjugate, as described herein, has a lipoatrophy effect that is comparable to human growth hormone, measured according to the assay to determine lipoatrophy of example 3 and other identical dosage regimen conditions.

GH Related Diseases

The term "a GH related" disease of second aspect simply herein relates to diseases and conditions where a human could benefit from GH.

This includes, but is not limited to, growth hormone deficiency, adult onset growth hormone deficiency, Turner syndrome, Prader-Willi syndrome, short bowel syndrome, chronic renal insufficiency, small for gestational age (SGA), AIDS wasting, antiageing, rheumatoid arthritis, idiopathic small stature, short stature homeobox gene and somatopause. Included is also other short stature condition, which includes Noonan syndrome, skeletal dysplasia, Down syndrome, short stature associated with prolonged steroid use, Aarskog's syndrome, among others.

Also included are chronic renal disease, juvenile rheumatoid arthritis; cystic fibrosis, HIV-infection in children receiving HAART treatment (HIV/HALS children); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; distraction oteogenesis; disorders resulting from hip or discus replacement, meniscus repair, spinal fusions or prosthesis fixation, such as in the knee, hip, shoulder, elbow, wrist or jaw; disorders resulting from fixing of osteosynthesis material, such as nails, screws and plates; non-union or malunion of fractures; disorders resulting from osteatomia, e.g. from tibia or 1st toe; disorders resulting from graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; and short stature due to glucucorticoid treatment in children.

FIGURES

In the figures the following is shown.

FIG. 1 shows SDS-PAGE analysis of purified permanent PEG-hGH conjugates, wherein Lane 1:HiMark™ Prestained High Molecular Weight Protein Standard; lane 2: compound 23; lane 3: compound 23; lane 4: compound 25; lane 5: compound 26, lane 6: compound 33; lane 7: compound 32; lane 8: compound 28; lane 9: compound 28; lane 10: compound 28; lane 11: compound 30; lane 12: compound 34; lane 13: compound 34; lane 14: compound 27; lane 15: compound 29.

Figure 7:
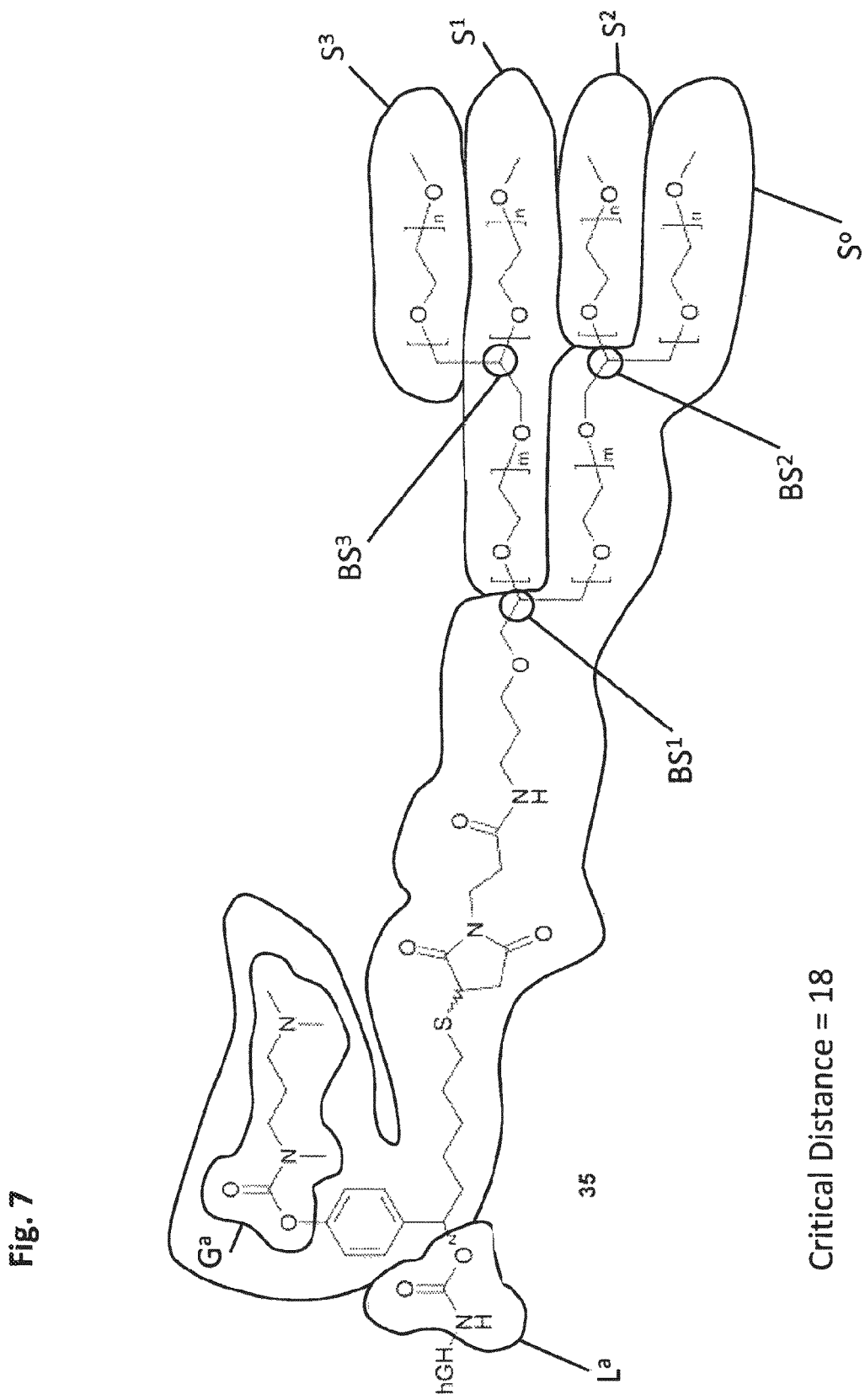
FIG. 7 to 10 show preferred prodrug conjugates of the present invention indicating $S^0$, $S^1$, $S^2$, $L^a$, $G^a$, $BS^1$, $BS^2$, $BS^3$ and the critical distance.
Figure 8:
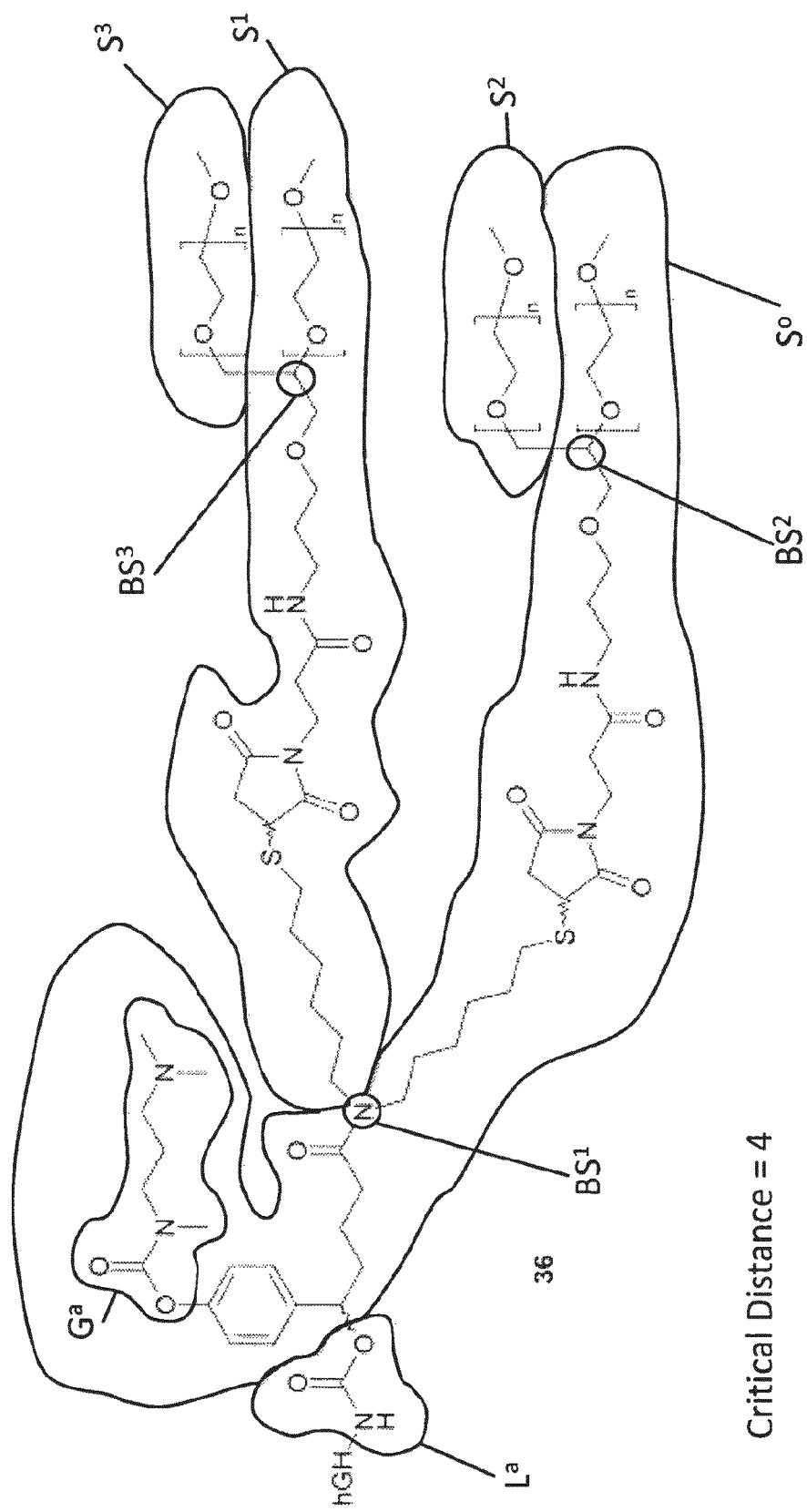

In detail, FIGS. 7 and 8 shows exemplary structures 35 and 38 of type (AA1, AAA1), where the at least 5 kDa polymer chain of $S^0$ comprising $G^a$ and $BS^1$ and $BS^2$ is marked as $S^0$; the carbamate group resulting from $L^a$ and the primary amino group of hGH is marked as $L^a$; $BS^1$ comprises the at least 4 kDa polymer chain marked as $S^1$, wherein $S^1$ comprises $BS^3$, which comprises the at least 4 kDa polymer chain marked as $S^3$. $BS^2$ comprises the at least 4 kDa polymer chain marked as $S^2$. The critical distance is given by 18 atoms for FIG. 7 and 4 atoms for FIG. 8.

Figure 9:
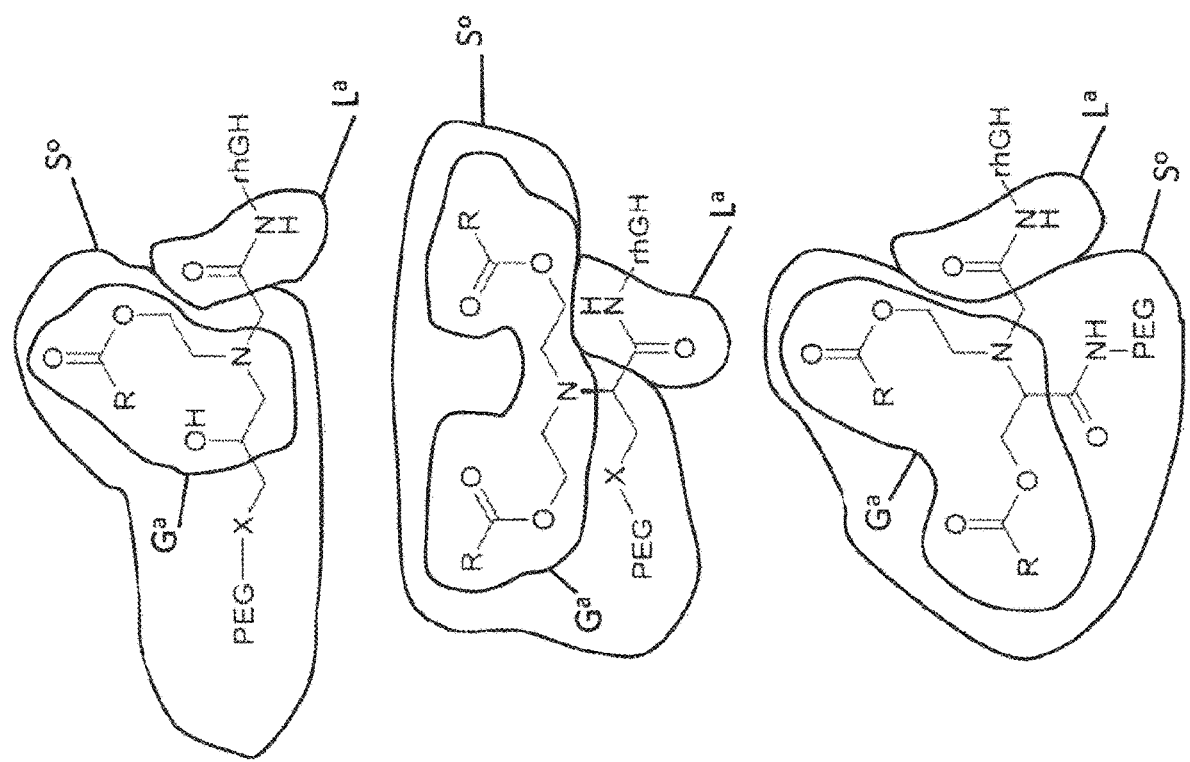
Figure 10:
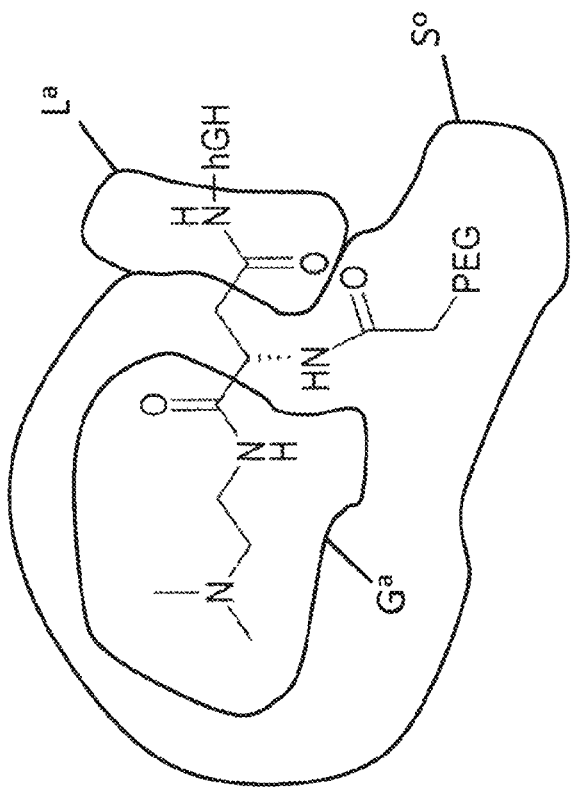

In FIGS. 9 and 10, exemplary structures of the type (AA2, AAA2) are shown, wherein the amide group resulting from $L^a$ and the primary amino group of hGH is marked as $L^a$ and the residue attached to $L^a$ is marked $S^0$ comprising $G^a$ and "PEG" representing the rest of $S^0$ comprising at least $BS^1$, $S^1$ and $S^2$ (all not shown).

EXAMPLES

Methods
Analytical and Preparative RP-HPLC

Analytical RP-HPLC/ESI-MS was performed on Waters equipment consisting of a 2695 sample manager, a 2487 Dual Absorbance Detector, and a ZQ 4000 ESI instrument equipped with a 5 µm Reprosil Pur 300 A ODS-3 columns (75×1.5 mm) (Dr. Maisch, Ammerbuch, Germany; flow rate: 350 µL/min, typical gradient: 10-90% acetonitrile in water, 0.05% TFA over 5 min).

For preparative RP-HPLC a Waters 600 controller and a 2487 Dual Absorbance Detector was used equipped with the following columns (Reprosil Pur 300 A ODS-3)

A): 100×20 mm, 10 mL/min flow rate, typical gradient: 10-90% acetonitrile in water, 0.1% TFA over 11 min or
B): 100×40 mm (10 µm particles), 40 mL/min flow rate, typical gradient: 10-90% acetonitrile in water, 0.1% TFA over 11 min.

Cation Exchange Chromatography

The purification of conjugates by cation exchange chromatography was performed using an AKTA Explorer system (GE Healthcare) equipped with a Macrocap SP column. The respective conjugate in 20 mM sodium acetate buffer pH 4 was applied to the column that was pre-equilibrated in 20 mM sodium acetate buffer pH4 (buffer A). The column was washed with three column volumes of Buffer A to remove any unreacted PEG reagent. Conjugates were eluted using a gradient of 10-60% buffer B (20 mM sodium acetate, 1 M sodium chloride, pH 4.5) over 20 column volumes or 0-40% buffer B over 20 column volumes and then 40-80% B over three column volumes. The flow rate was 7 ml/min and the eluent was monitored by detection at 280 nm.

Anion Exchange Chromatography

The purification of conjugates by anion exchange chromatography was performed using an AKTA Explorer system (GE Healthcare) equipped with a Source Q column. The respective conjugate in 20 mM Tris/HCl buffer pH 7.5 (buffer C) was applied to the column that was pre-equilibrated in buffer C. The column was washed with three column volumes of buffer C to remove any unreacted PEG reagent. Conjugates were eluted using a gradient of 0-20% buffer D (20 mM Tris/HCl, 1 M sodium chloride, pH 7.5) over 25 column volumes. The flow rate was 5 ml/min and the eluent was monitored by UV detection at 280 nm. Alternatively, the buffer system 20 mM bis-tris/HCl, pH 6.5 (buffer E) and 20 mM bis-tris/HCl, 1 M sodium chloride, pH 6.5 (buffer F) was used.

Analytical Size Exclusion Chromatography

Analytical size exclusion chromatography analysis was performed on a AKTA Explorer (GE Healthcare) system. Samples were analyzed using a Superdex 200 or a Sepharose 6 column (10×300 mm) and 20 mM sodium phosphate, 135 mM sodium chloride, pH 7.4 was used as mobile phase. The flow rate for the column was 0.75 ml/min and the eluted hGH and polymer-hGH conjugates were detected at 215 nm and 280 nm.

Activity Determination of pfp-Activated mPEG-Linker Reagents

A defined amount of pfp-activated mPEG-linker reagent (3-5 mg) was dissolved in 100 μL WATER. 10 μL 0.5 M NaOH were added and the reaction mixture was reacted for 60 min at 40° C. 1.5 μL TFA were added and 10% of this mixture were analyzed by analytical RP-HPLC. The chromatograms were recorded at 260 and 280 nm. The peak corresponding to pentafluorophenol was integrated. Determined values were compared with an appropriate calibration curve generated by analyzing defined amounts of pfp by analytical RP-HPLC and integration of chromatograms recorded at 260 and 280 nm.

SDS-PAGE Analysis

The permanent mPEG-hGH conjugates were analysed using NuPAGE® Novex Tris-Acetate gels (1.5 mm thick, 15 lanes), NuPAGE Tris-Acetate SDS-Running Buffer, HiMark™ Pre-stained High Molecular Weight Protein Standard and Simply Blue™ SafeStain (Invitrogen). In each lane 0.2-0.6 μg conjugate were applied and the electrophoresis and subsequent staining performed according to the supplier's protocol.

Example 1: Assay to Measure hGH PEGylated Prodrug and hGH Activity

The biological activity of hGH is measured by using standard assays known to the skilled person in the art. As described in EP1715887B1 and as also discussed above, the biological activity associated with the native or modified hGH (for example a PEGylated hGH), can be measured using standard FDC-P1 cell proliferation assays, (Clark et al, Journal of Biological Chemistry 271:21969-21977) or receptor binding assay (U.S. Pat. No. 5,057,417).

On line 8 (page 14) of patent EP1715887B1, it is described that the preferred in vitro activity has to be as high as possible, most preferred the modified hGH has equivalent or improved in vitro biological activity, in current invention, the biological activity has to be as low as possible compared to native hGH. Thus current inventors did the complete opposite compared to the prior art described in EP1 715887B1.

In vitro Assay

The in vitro activities of the permanent PEG-hGH conjugates described in the examples below are determined using one or more standard assays for assessing biological activity in vitro. Standard assays that may be employed include cell proliferation assays using, e.g., FDC-PI cells (see, e.g., Clark et al., Journal of Biological Chemistry, 271:21969-21977, 1996), or Ba/F3-hGHR cells, which express receptors for hGH, hGH delta 135-146, or Nb2 rat lymphoma cells, which proliferate in response to hGH via the lactogenic receptors (see, e.g., Alam, K. S., et al., J. Biotech 2000, February 28, 78(1), 49-59). Receptor binding assays (see, e.g., U.S. Pat. No. 5,057,417) may also be used.

Nb2-1 1 is a clone of the Nb-2 rat lymphoma line which was derived from a transplant of a lymphoma that developed in the thymus/lymph node of a male noble (Nb) strain rat following prolonged oestrogen treatment. The cells are of the pre-T cell origin and their proliferation is dependent on mammalian lactogens, such as prolactin. Nb2-1 1 can also be mitogenically stimulated by IL-2. Injection of Nb2 cells into Nb rats gives rise to malignant tumors that are highly sensitive to treatment with *vinca* alkaloids. Karyotypic analysis has shown that the cell line has only five well developed chromosome abnormalities. The cells do not express surface immunoglobulin, and their lactogens dependency is confirmed. Protocols for the use of Nb2-1 1 cells in bioassays are available from ECACC on request.

As WO20061 02659 describes on page 74 paragraph 0240 example 7, the biological activity of hGH and the conjugates described herein shall be assessed in vitro using an NB2-1 1 rat lymphoma cell proliferation assay. Briefly, NB2-1 1 cells derived from a rat lymphoma are incubated with hGH, which lead to binding of the hGH molecule to its receptor on the cell surface. Receptor binding induces the signal transduction cascade, which results in proliferation of the cells. Assay results are based on determined protein content, and a 100% bioactivity of unmodified hGH.

Conclusion:

Based on detailed instructions of this example 1 it is routine work for the skilled person to measure this residual activity of the prodrug.

Example 2: Assay to Measure Autocleavage Rate of the Transient Linker of the Prodrug Determination of In Vitro Half-Life For determination of in vitro linker cleavage rate of PEG-linker-hGH conjugates, the compounds are dissolved in buffer at pH 7.4 (e.g. 10 mM sodium phosphate, 140 mM NaCl, 3 mM EDTA) and solution is filtered through a 0.22 μm filter and incubated at 37° C. Samples are taken at time intervals and analyzed by RP-HPLC or size exclusion chromatography at 215 nm. Peaks corresponding to liberated hGH are integrated and plotted against incubation time. Curve fitting software is applied to determine first-order cleavage rates.

In Vivo Half-Life Determination and In Vitro/In Vivo Half-Life Correlation

Linker cleavage rates in vivo are determined by comparing the pharmacokinetics of permanent PEG-hGH conjugates with the respective transient PEG-linker-hGH conjugate carrying the same PEG moiety after intravenous injection into rat.

Firstly, permanent PEG-hGH conjugate is injected intravenously into rats and blood samples are taken at time intervals, plasma prepared, and analyzed for hGH using an ELISA.

Secondly, transient PEG-hGH conjugate is injected intravenously in rats, blood samples are taken at time intervals, plasma prepared, and analyzed for hGH using an ELISA.

In vivo half-life is calculated from the ratio of hGH concentration of transient conjugate divided by determined hGH concentration of permanent conjugate at the respective time points and curve fitting. Data are compared to in vitro half-life measurements.

Conclusion

Based on detailed instructions of this example 2 it is routine work for the skilled person to measure the in vivo half-life of the hGH-PEGylated prodrug.

Example 3: Assay to Measure Lipoatrophy

As said above compound PHA-794428 is a PEGylated-hGH and described in patent EP1715887 from the company Pharmacia. According to www.clinicaltrials.gov, the study was terminated on 10 Dec. 2007. Pfizer's (Pharmacia) decision to terminate the program was due to cases of injection-site lipoatrophy that were reported in the clinical Phase 2 studies after a single injection of PH A 794428. Lipoatrophy is the term describing the localized loss of fat tissue and is visible on humans as holes in the skin (visible by the eye).

Assay

There are several in vitro methods described in the art in measure lipoatrophy. One proposal is described in publication J. Anim. Sci (1972), 35: 794-800 (L J. Machlin) on page 795. Another description is found in Int. J. Cancer; 80, 444-447 (1999).

Generally, lipoatrophy can be measured as proposed below.

Lipolytic effect can be determined using an in vitro assay consisting of isolated mammal adipocytes, preferable murine adipocytes. Samples to be assayed were incubated at physiologically relevant conditions with a predetermined number of adipocytes in Krebs-Ringer bicarbonate buffer containing appropriate nutrients for up to 6 hours. The concentration of released glycerol is determined by standard methods, for example enzymatically or by a radiometric detection. Control samples containing adipocytes alone are analyzed to determine the spontaneous glycerol release.

The lipolytic effect of native unmodified recombinant human growth hormone and permanently PEGylated recombinant human growth hormone is compared to that of transiently PEGylated recombinant human growth hormone.

Conclusion

Based on detailed instructions of this example 3 it is routine work for the skilled person to measure the lipoatrophy effect.

Example 4 Synthesis of Permanent Linker Reagent 12a and Transient Linker Reagents 12b and 12c

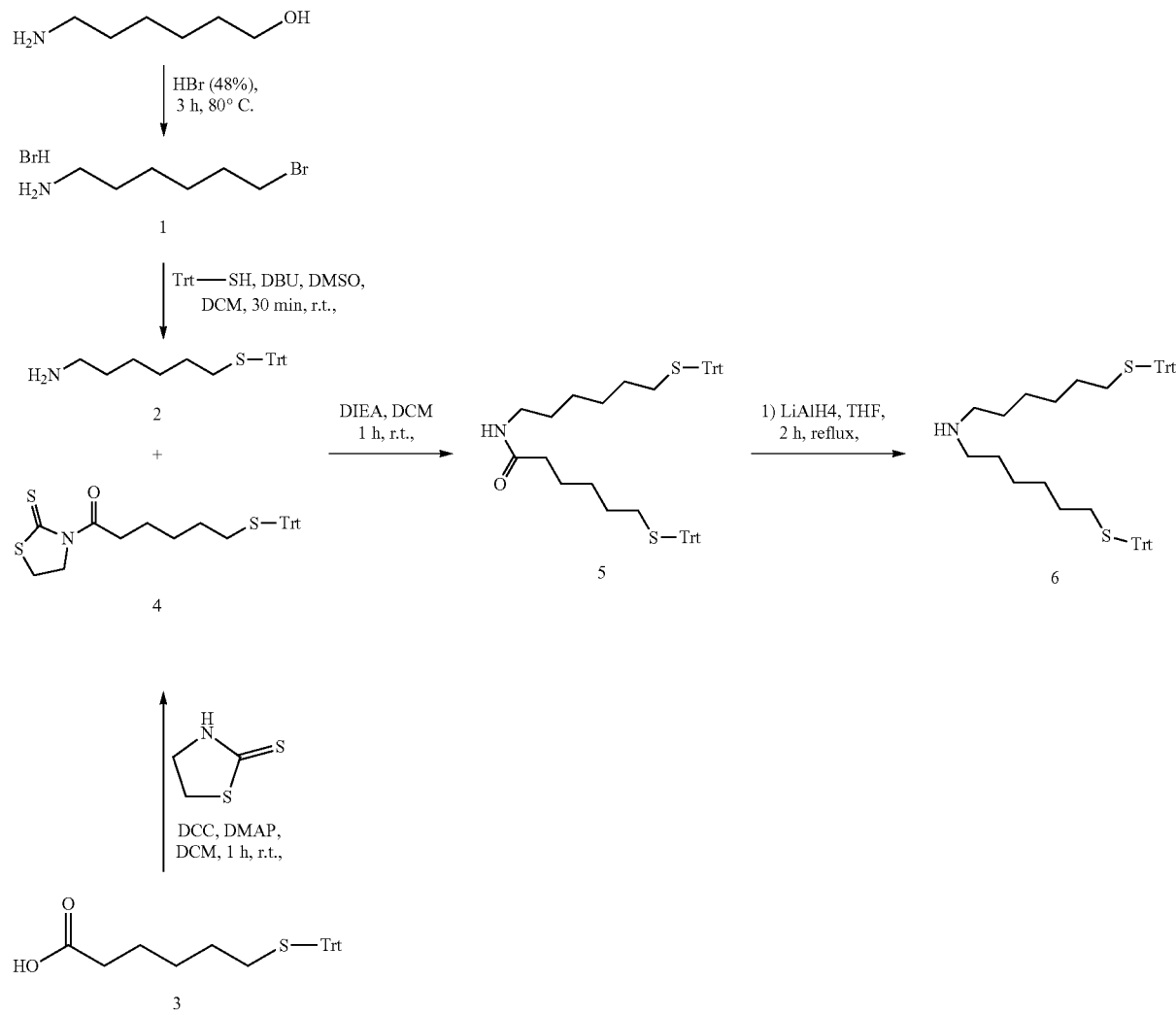

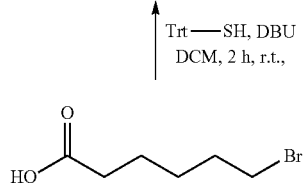

6-Amino-hexan-1-ol (2.85 g, 24.3 mmol) was dissolved in aq. HBr (48%, 10 mL, 89 mmol) and stirred at 80° C. for 3 h. Excess HBr was evaporated at 50-65° C. and 15 Torr and the residue was dried in vacuo.

1: Yield 6.07 g (96%)

MS [M+H]$^+$=180.3 g/mol (MW+H calculated=180.0 g/mol)

DBU (3.5 mL, 23.2 mmol) was added to a suspension of 6-Bromohexylamine hydro-bromide 1 (3.03 g, 11.6 mmol) and triphenyl-methanethiol (2.14 g, 7.74 mmol) in DCM (25 mL) and DMSO (13 mL) were added. The reaction mixture was stirred for 30 min at room temperature and diluted with water (150 mL).

The aqueous layer was extracted with ether and the combined organic phase was evaporated. 2 was purified by RP-HPLC.

2: Yield 1.17 g (40%)

MS [M+H]$^+$=376.7 g/mol (MW+H calculated=376.2 g/mol).

DBU (4.56 mL, 30.0 mmol) was added to 6-bromo-hexanoic acid (3.90 g, 20.0 mmol) and triphenyl-methanethiol (11.1 g, 40.0 mmol) in DCM (40 mL). After stirring at room temperature for 1 h ice cold 1 M H$_2$SO$_4$ (50 ml.) was added and the mixture was extracted with DCM. The combined organic phase was dried over Na$_2$SO$_4$ and concentrated in vacuo. Compound 3 was purified by silica gel column chromatography (200 ml.) using heptane/ethyl acetate (4/1, R$_f$=0.2) as mobile phase.

3: Yield 5.83 g (75%)

DMAP (37 mg, 0.31 mmol) was added to 6-tritylsulfanyl-hexanoic acid 3 (5.83 g, 14.9 mmol), thiazolidine-2-one (3.56 g, 29.9 mmol), and dicyclohexylcarbodiimide (3.08, 14.9 mmol) in DCM (100 mL). After stirring at room temperature for 1 h 1 M HCl (0.6 ml.) was added and the mixture was filtered. The filtrate was concentrated in vacuo and 4 was purified by silica gel column chromatography (180 ml.) using heptane/ethyl acetate (1/1) as mobile phase.

4: Yield 7.15 g (97%) as yellow oil

A solution of 1-(2-thioxo-thiazolidin-3-yl)-6-tritylsulfa-nyl-hexan-1-one 4 (1.53 g, 3.11 mmol) in THF (13 ml.) was added over a period of 2 min to 6-tritylsulfanyl-hexylamine 2 (1.17 g, 3.11 mmol) in DMSO (1 ml.) and THF (5 mL). After addition of triethylamine (435 µL, 3.11 mmol) the reaction mixture was stirred for 90 min at room temperature. Ether (200 ml.) and water (100 ml.) were added and the phases separated. After extraction of the aqueous phase with ether the combined organic phases were dried over Na$_2$SO$_4$ and concentrated in vacuo. Compound 5 was purified by silica gel column chromatography (150 ml.) using heptane/ethyl acetate (2/1, R$_f$=0.1) as mobile phase.

5: Yield 1.23 g (53%)

MS [M+Na]$^+$=770.6 g/mol (MW+Na calculated=770.4 g/mol)

Under nitrogen, a 1M solution of LiAlH$_4$ in THF (1.2 ml, 4.8 mmol) was placed in a dry flask, and a solution of 5 (509 mg, 0.680 mmol) in 10 ml of THF was added over 4 min.

The mixture was stirred under reflux for 2 h, until complete conversion of the starting material was shown by thin layer chromatography (heptanes/ethyl acetate 1:1). The reaction mixture was carefully quenched with a 10:1 suspension of water in diethyl ether until the gas evolution had stopped. The mixture was poured into 50 ml of a saturated solution of sodium potassium tartrate and stirred for 90 min. 90 ml of ethyl acetate were added and the phases were separated. The aqueous phase was extracted with ethyl acetate (4×20 ml), and the combined organic phase was washed with brine (30 ml), dried over MgSO$_4$, filtered, and concentrated to give a transparent oil. 6 was adsorbed on silica and purified by flash chromatography (30 g silica, CH$_2$Cl$_2$/MeOH 20:1 (v/v)+0.1% NEt$_3$). The product was obtained as an off-white viscous oil.

6: Yield 270 mg (54%)

MS [M+H]$^+$=734.4 g/mol (MW+H calculated=734.4 g/mol)

R$_f$=0.28 (CH$_2$Cl$_2$/MeOH 19:1)

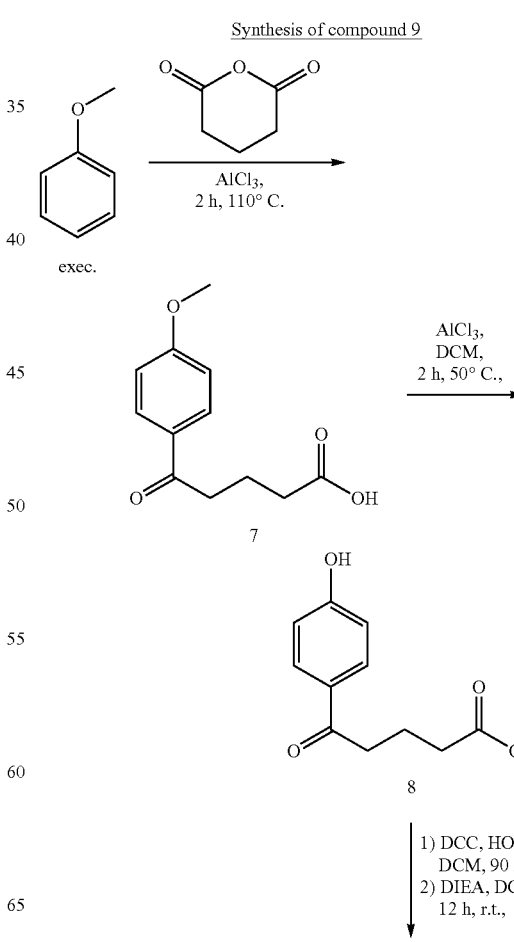

Synthesis of compound 9

-continued

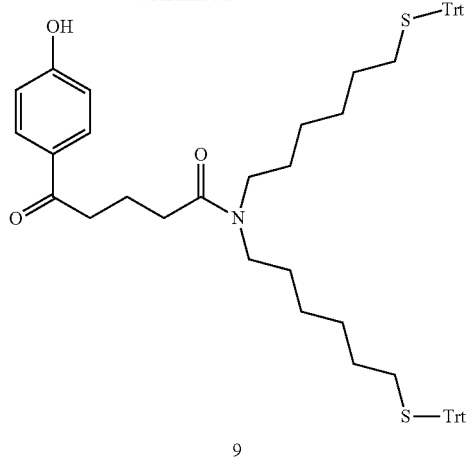

9

AlCl₃ (23.0 g, 172.3 mmol) was added to glutaric anhydride (10.0 g, 86.2 mmol) in anisole (85 mL, 781 mmol). The reaction mixture was heated to 110° C. for 2 h, cooled to room temperature, poured on 3 N HCl/ice and extracted with dichloromethane. The aqueous phase was extracted with dichloromethane (4×20 ml), and the combined organic fractions were washed with brine (30 ml), dried over MgSO₄, filtered and concentrated to give a red oil that was recrystallized from toluene. Product 7 was obtained as an off-white solid.

7: Yield 5.2 g (48%)

MS [M+Na]⁺=245.8 (MW+Na calculated=245.1 g/mol)

AlCl3 (9.0 mg, 68 mmol) was added to 7 (5.0 g, 23 mmol) in 1,2-dichloroethane. The reaction mixture was stirred for 14 h at 85° C. and subsequently cooled to room temperature. Ice cold 1 N HCl (50 ml.) was added and the mixture was extracted with ethyl acetate (4×30 mL). The combined organic fractions were dried over Na₂SC>₄, filtered and concentrated in vacuo to give a light red solid that was used in the next step without further purification.

8: Yield 3 g (62%)

MS [M+H]⁺=209.1 (MW+H calculated=209.1 g/mol)

dicyclohexylcarbodiimide (532 mg, 2.6 mmol), acid 8 (403 mg, 1.9 mmol), HOSu (297 mg, 2.6 mmol), and collidine (1.0 mL, 7.8 mmol) in DCM (10 ml.) were stirred for 90 min at room temperature. After removal of dicyclohexylurea by filtration, amine 6 (947 mg, 1.3 mmol) in DCM (5 ml.) and DIEA (450 µL, 2.6 mmol) were added to the filtrate and the mixture was reacted for 14 h at room temperature. 1 N H₂SO₄ (2×50 ml.) was added and the phases were separated. The aqueous phase was extracted with ethyl acetate (4×20 ml), and the combined organic phase was washed with brine (30 ml), dried over MgSO₄, filtered and concentrated in vacuo. The residues were purified by silica gel column chromatography (150 ml.) using heptane/ethyl acetate (½, R_f=0.66) as mobile phase.

9: Yield 819 mg (69%)

MS [M+Na]⁺=946.4 (MW+Na calculated=946.4 g/mol)

Synthesis of permanent linker reagent 12a and transient linker reagent 12b and 12c

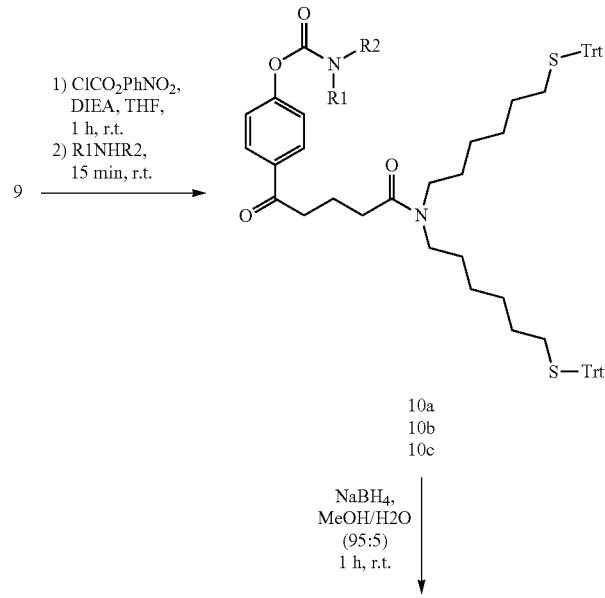

10a
10b
10c

NaBH₄,
MeOH/H2O
(95:5)
1 h, r.t.

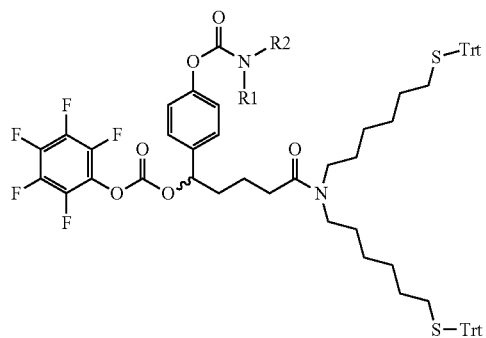
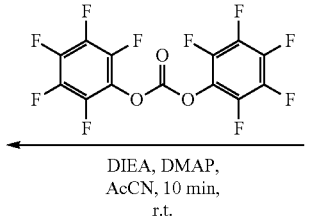
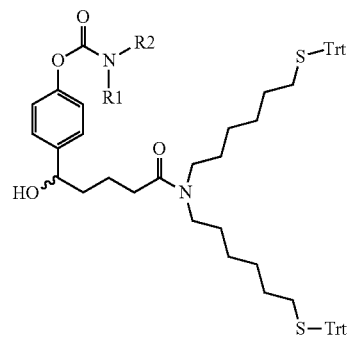

12a
12b
12c a: R1 = R2 = Et b: R1 = Et, R2 = 2-(diethylamino)ethyl c: R1 = Me, R2 = 3-(dimethylamino)propyl 11a
11b
11c

20

9 (1 eq., 175 mg, 0.19 mmol) was dissolved in dry THF (1.5 mL, p-nitrophenylchloroformate (1.1 eq., 42 mg, 0.21 mmol) and DIPEA (2 eq., 66 µl, 0.38 mmol) were added and the mixture was stirred for 60 min at room temperature. Di-ethylamine (R1=R2=Et, 2 eq., 39 gi, 0.38 mmol) was added and stirring was continued for 15 min. The solvent was removed in vacuo, 100 µl of AcOH were added and 10a was purified by RP-HPLC.

MS [M+Na]$^+$=1045.9 (MW+Na calculated=1045.5 g/mol)

NaBH$_4$ (5 eq., 37 mg, 0.95 mmol) was added to 10a containing HPLC fraction (acetonitrile/H20 ~3/1 (v/v)+ 0.1% TFA) and the mixture was reacted for 10 min at room temperature. An additional portion of NaBH$_4$ (5 eq., 37 mg, 0.95 mmol) was added and the reaction mixture was stirred until complete conversion of the starting material was indicated by LC/MS analysis (10 min at room temperature). 11a was purified by RP-HPLC and lyophilized.

11a: Yield 95 mg (49% based on 9)

MS [M+Na+H]$^+$=1047.7 (MW+Na calculated=1047.5 g/mol)

9 (1 eq., 175 mg, 0.19 mmol) was dissolved in dry THF (1.5 mL), p-nitrophenylchloroformate (1.1 eq., 42 mg, 0.21 mmol) and DIPEA (2 eq., 66 µl, 0.38 mmol) were added and the mixture was stirred for 60 min at room temperature. N,N,N'-Triethyl-ethane-1,2-diamine (R1=Et, R2=2-(diethylamino)ethyl, 2 eq., 68 µl, 0.38 mmol) was added and stirring was continued for 15 min. 100 µl of AcOH were added, the solvent was removed in vacuo and 10b was purified by RP-HPLC and lyophilized.

10b: Yield 147 mg as TFA salt (65%)

MS [M+Na]$^+$=1116.4 (MW+Na calculated=1116.6 g/mol)

10c was synthesized as described above using N,N,N'-trimethyl-propane-1,3-diamine (R1=Me, R2=3-(dimethylamino)propyl, 56 µL, 0.38 mmol) as diamine.

10c: Yield 134 mg as TFA salt (59%)

MS [M+Na]$^+$=1088.4 (MW+Na calculated=1088.6 g/mol)

NaBH$_4$ (46 mg, 1.2 mmol) was added to 10b (147 mg, 0.12 mmol) in MeOH/water=95:5 (v/v) (3 mL) in two doses and the mixture was stirred for 1 h at room temperature. After addition of AcOH (300 µL) and concentration, product 11b was purified by RP-HPLC and lyophilized.

11b: Yield 107 mg as TFA salt (73%)

MS [M+Na]$^+$=1118.4 (MW+Na calculated=1118.6 g/mol)

11c was synthesized according to the same protocol.

11c: Yield 65 mg as HCl salt (54%) from 134 mg starting material

MS [M+Na]$^+$=1090.4 (MW+Na calculated=1090.6 g/mol)

Under a nitrogen atmosphere bis-pentafluorophenyl-carbonate (2.5 eq., 25 mg, 63 µmol), DMAP (1 mg), and DIEA (5 eq., 22 µL, 127 µmol) were added to 11a (1 eq., 26 mg, 26 µmol) in dry acetonitrile (0.5 mL. The reaction mixture was stirred for 30 min at room temperature, cooled to 0° C., and acidified with AcOH (200 µL. Product 12a was purified by RP-HPLC and lyophilized.

12a: Yield 13 mg (42%)

MS [M+Na]$^+$=1258.2 (MW+Na calculated=1257.5 g/mol)

12b and 12c were prepared accordingly from 11b (56 mg, 48 µmol) and 11c (88 mg, 73 µmol), respectively.

12b: Yield 63 mg as TFA salt (93%)

MS [M+H]$^+$=1306.3 (MW+H calculated=1306.6 g/mol)

12c: Yield 4 1 mg as TFA salt (41%)

MS [M+H]$^+$=1278.4 (MW+Na calculated=1278.5 g/mol)

Example 5 Synthesis of Permanent Linker Reagent 14a and Transient Linker Reagents 14c

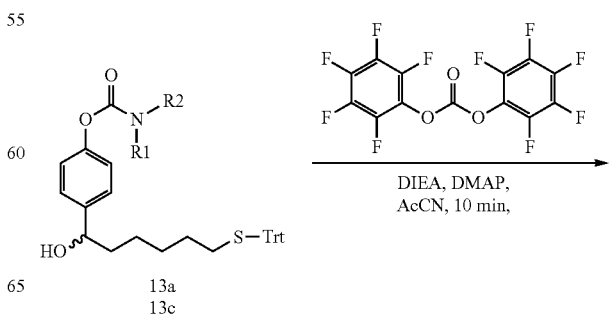

13a
13c

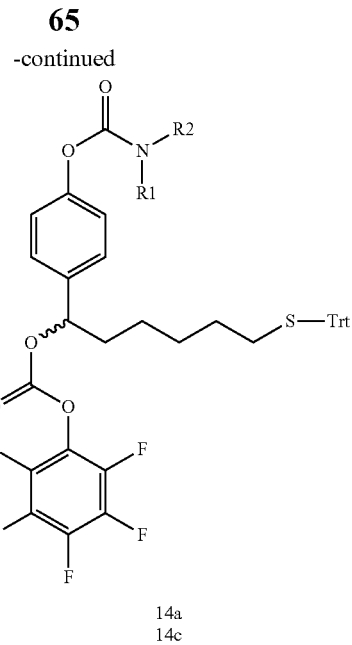

14a
14c a: R1 = R2 = ethyl c: R1 = Me, R2 = 3-(dimethylamino)propyl 13a and 13c were synthesized as described in WO2005/099768A2.

Under an atmosphere of nitrogen bispentafluorophenyl-carbonate (631 mg, 1.6 mmol), DMAP (20 mg, 0.16 mmol), and DIEA (556 μL, 3.2 mmol) were added to 13a (364 mg, 0.64 mmol) in dry acetonitrile (5 mL). The reaction mixture was stirred for 15 min at room temperature, cooled to 0° C., and acidified with acetic acid (1 mL). Product 14a was purified by RP-HPLC and lyophilized.

14a: Yield 379 mg (77%)

MS [M+Na]$^+$=800.4 (MW+Na calculated=800.3 g/mol)

14c was prepared accordingly from 13c (97 mg, 130 μmol).

14c: Yield 114 mg as TFA salt (94%)

MS [M+H]$^+$=821 0.5 (MW+H calculated=821.3 g/mol)

Example 6 Synthesis of Permanent Linker Reagent 15

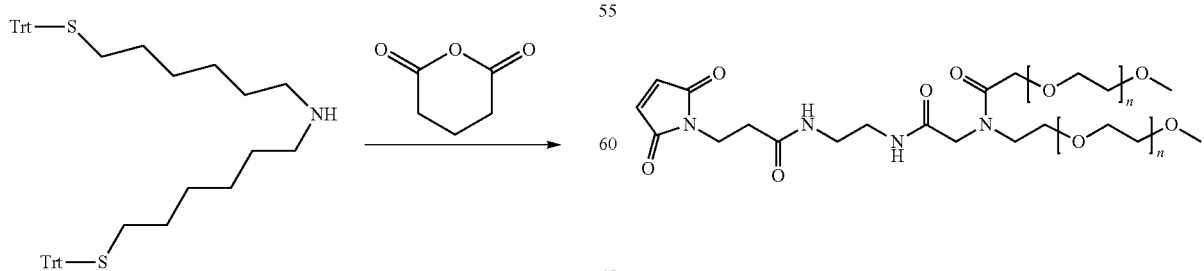

6

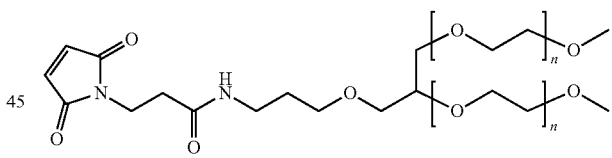

15

Glutaric anhydride (0.41 mmol), amine 6 (200 mg, 0.27 mmol), DIPEA (72 μL, 0.41 mmol), and DMAP (11 mg, 0.09 mmol) were stirred in acetonitrile (3 ml.) for 2 h at 80° C. The mixture was cooled to room temperature and acetic acid (200 μL) was added. Product 15 was purified by RP-HPLC and lyophilized.

15: Yield 130 mg (57%)

MS [M+Na]$^+$=870.2 (MW+Na calculated=870.4 g/mol)

Example 7 Synthesis of Activated mPEG-Linker Reagents mPEG-Maleimide Starting Materials:

mPEG-maleimide 1A: MW=ca. 20 kDa (n=ca. 200-250)
mPEG-maleimide 1B: MW=ca. 40 kDa (n=ca. 400-500)

mPEG-maleimide 2A: MW=ca. 20 kDa (n=ca. 200-250)
mPEG-maleimide 2B: MW=ca. 40 kDa (n=ca. 400-500)

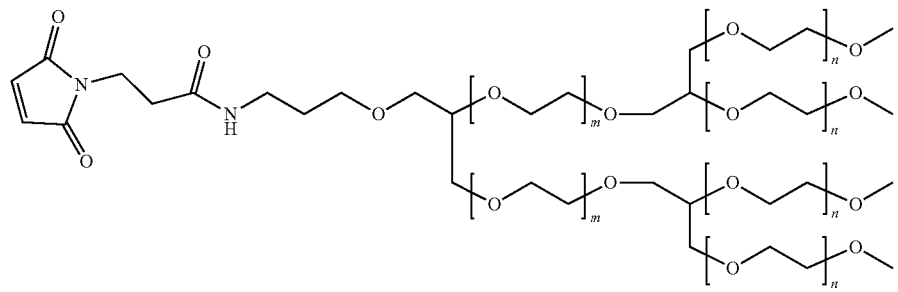

mPEG-maleimide 3A: MW=ca. 40 kDa (n=ca. 100-125; m=ca. 200-250)

mPEG-maleimide 3B: MW=ca. 80 kDa (n=ca. 200-250; m=ca. 400-500)

mPEG residues after reacting with thiol group (R3 in structures below):

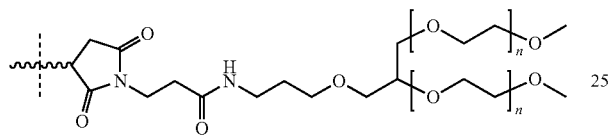

mPEG-succinimide residue 1AA: MW=ca. 20 kDa (n=ca. 200-250)

mPEG-succinimide residue 1BA: MW=ca. 40 kDa (n=ca. 400-500)

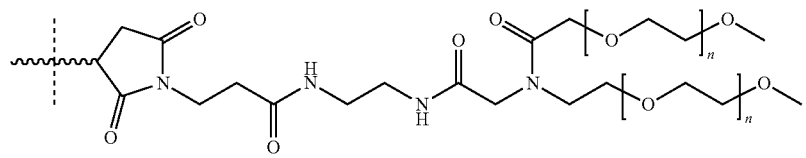

mPEG-succinimide residue 2AA: MW=ca. 20 kDa (n=ca. 200-250)

mPEG-succinimide residue 2BA: MW=ca. 40 kDa (n=ca. 400-500)

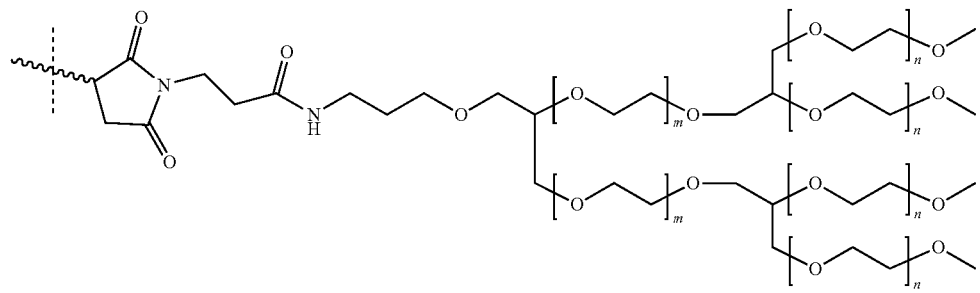

mPEG-succinimide residue 3AA: MW=ca. 40 kDa (n=ca. 100-125; m=ca. 200-250)

mPEG-succinimide residue 3BA: MW=ca. 80 kDa (n=ca. 200-250; m=ca. 400-500)

The vertical dashed line denotes the attachment site to the thiol group in the respective structure Synthesis of permanent pfp-activated mPEG-linker reagents 17aa, 17ab, 17ac, 17ad, and transient pfp-activated mPEG-linker reagents 17b, 17ca, and 17cb

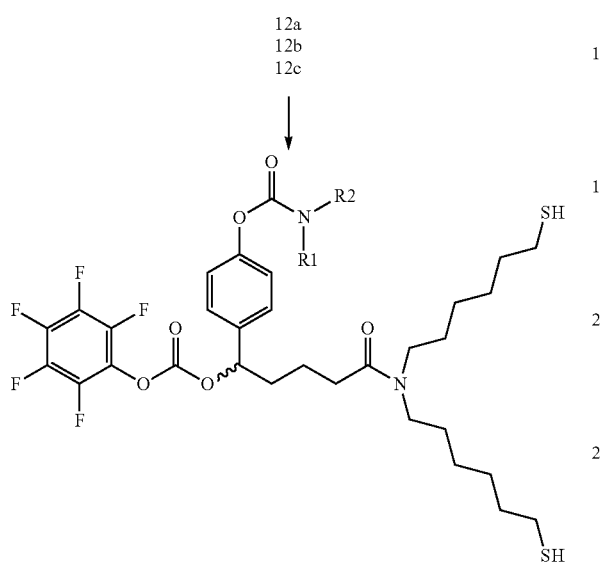

16a: R1 = R2 = Ethyl
16b: R1 = Ethyl, R2 = 2-(diethylamino)ethyl
16c: R1 = Me, R2 = 3-(dimethylamino)propyl

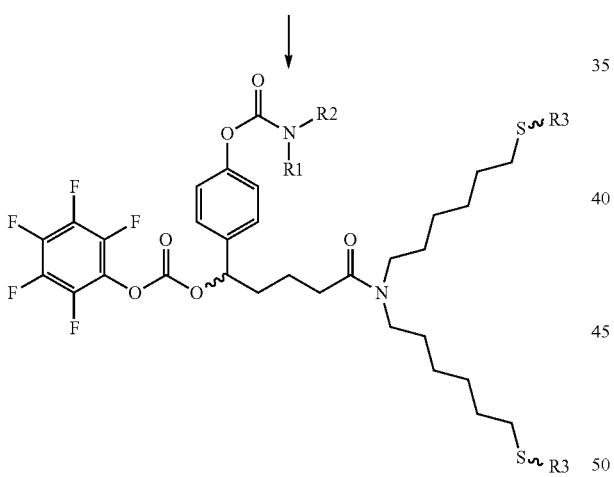

17aa: R1 = R2 = Ethyl, R3 = 1AA
17ab: R1 = R2 = Ethyl, R3 = 1BA
17ac: R1 = R2 = Ethyl, R3 = 2AA
17ad: R1 = R2 = Ethyl, R3 = 2BA
17b: R1 = Ethyl, R2 = 2-(diethylamino)ethyl, R3 = 1BA
17ca: R1 = Me, R2 = 3-(dimethylamino)propyl, R3 = 1BA
17cb: R1 = Me, R2 = 3-(dimethylamino)propyl, R3 = 2BA Carbonate 12a (13 mg, 10 µmol) was stirred in 10 µL AcOH, 700 µL, HFIP, 1 µL TFA and 2 µL TES for 10 min at room temperature. The volatile components were removed in a nitrogen stream and 16a was purified by RP-HPLC.

16a: Yield 3.8 mg (5 g/mol)
MS [M+H]$^+$=751 0.3 (MW+H calculated=751.3 g/mol)
16b and 16c were prepared accordingly from 12b (7.7 mg, 5.4 µmol) and 12c (2 mg, 1.5 µmol), respectively.

16b: Yield 2.5 mg (2.7 µmol)
MS [M+Na]$^+$=845.1 (MW+Na calculated=844.3 g/mol)
16c: Yield 0.5 mg (0.6 µmol)
MS [M+Na]$^+$=816.6 (MW+Na calculated=816.3 g/mol)

mPEG-maleimide 1B (NOF, Japan) (521 mg, 12.7 µmol) was added to 3.5 mg (3.9 µmol) 16c in 4 ml. 3/1 (v/v) acetonitrile/water+0.1% TFA. 200 µL of 0.5 M phosphate buffer pH 7.4 were added and the mixture was reacted for 10 min at room temperature. 1 µL (13 µmol) mercaptoethanol were added and the reaction mixture was acidified to pH 4-5 by addition of TFA. 17 ca was purified by RP-HPLC and lyophilized.

17ca: Yield 220 mg (pfp-carbonate activity 82%)
17cb was synthesized as described for 17ca using 16c (3.5 mg, 3.9 µmol) and mPEG-maleimide 2B (656 mg, 16 µmol).
17cb: Yield 130 mg (pfp-carbonate activity 85%)

184 mg (8.8 µmol) mPEG-maleimide 1A (NOF, Japan) were added to 16a (2.0 mg, 2.7 µmol) in 4 ml. 1/1 (v/v) acetonitrile/water+0.1% TFA. 200 µL of 0.5 M phosphate buffer pH7.4 were added and the mixture was reacted for 10 min at room temperature. 0.2 µL (1.6 µmol) mercaptoethanol were added and the reaction mixture was acidified to pH 2-3 by addition of TFA. 17aa was separated from unreacted PEGs by RP-HPLC and lyophilized.

17aa: Yield 90 mg (pfp-carbonate activity 88%)
17ab was synthesized as described above using 16a (3.8 mg, 5.0 µmol) and 680 mg (16 µmol) mPEG-maleimide 1B (NOF, Japan).
17ab: Yield 250 mg (pfp-carbonate activity 83%)
17ac was synthesized as described above using 16a (2.5 mg, 3.3 µmol) and 200 mg (9.5 µmol) mPEG-maleimide 2A (Jenkem, PR China).
17ac: Yield 80 mg (pfp-carbonate activity 80%)
17ad can be synthesized as described above using 16a and mPEG-maleimide 2B.
17b can be synthesized as described for 17cb using 16b and mPEG-maleimide 1B.

Example 8 Synthesis of pfp-Activated Permanent mPEG Linker Reagents 19aa and 19ab and Transient Permanent mPEG-Linker Reagent 19c

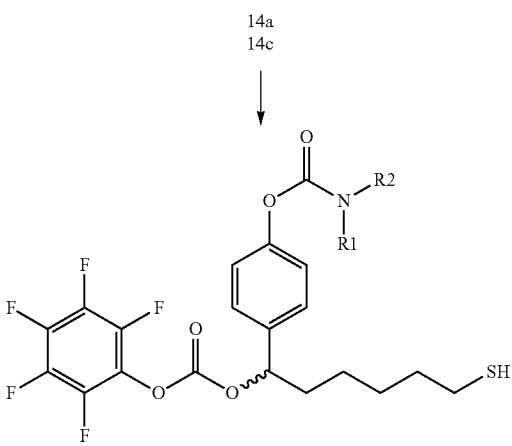

18a: R1 = R2 = Ethyl
18c: R1 = Me, R2 = 3-(dimethylamino)propyl

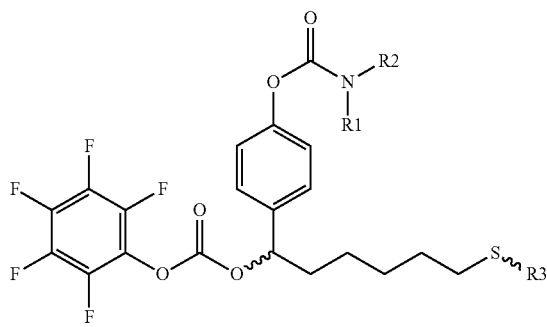

19aa: R1 = R2 = Ethyl, R3 = 3AA
19ab: R1 = R2 = Ethyl, R3 = 3BA
19c: R1 = Me, R2 = 3-(dimethylamino)propyl, R3 = 3AA Carbonate 14c (20 mg, 21 μmol) was stirred in 10 μL AcOH, 400 μL HFIP, and 5 μL TES for 10 min at room temperature and cooled to 0° C. Ice cold acetonitrile/water=9/1 (v/v) was added and 18c was separated by RP-HPLC and lyophilized.

18c: Yield 5.0 mg as TFA salt (7.2 μmol)
MS [M+H]⁺=579.6 (MW+H calculated=579.2 g/mol)
18a was synthesized as described above using carbonate 14a (24 mg, 31 μmol).
18a: Yield 8.0 mg (15 μmol)
MS [M+H]⁺=536.2 (MW+H calculated=536.5 g/mol)
205 mg (5 μmol) mPEG-maleimide 3A (NOF, Japan) were added to 18a (4.0 mg, 7.5 μmol) in 2 ml. 1/1 (v/v) acetonitrile/water+0.1% TFA. 100 μL of 0.5 M phosphate buffer (pH7.4) were added and the mixture was reacted for 10 min at room temperature. The reaction mixture was acidified to pH 2-3 by addition of TFA and 19aa was separated from unreacted PEGs by RP-HPLC and lyophilized.

19aa: Yield 125 mg (pfp-carbonate activity 85%)
19ab was prepared accordingly from 410 mg (5 μmol) mPEG-maleimide 3B (NOF, Japan) and 18a (4.0 mg, 7.5 μmol).
19ab: Yield 265 mg (pfp-carbonate activity 87%)
19c was prepared accordingly from 205 mg mPEG-maleimide 3A and 18c (5 mg, 7.2 μmol)
19c: Yield 120 mg (pfp-carbonate activity 88%)

Example 9: Synthesis of Permanent 4-Arm Branched 80 kDa mPEG-NHS Ester Derivative 22

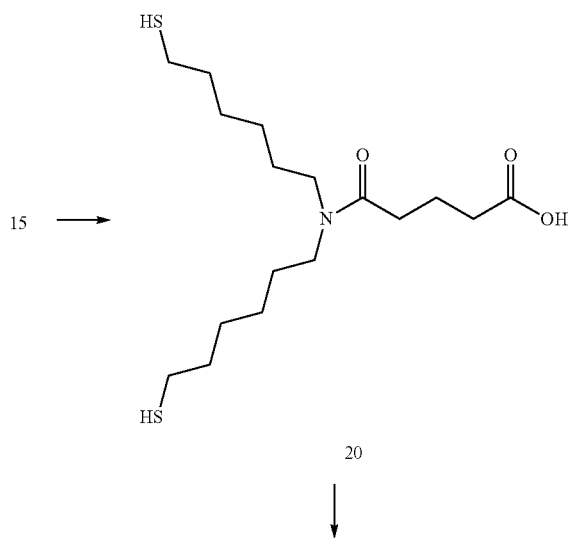

-continued

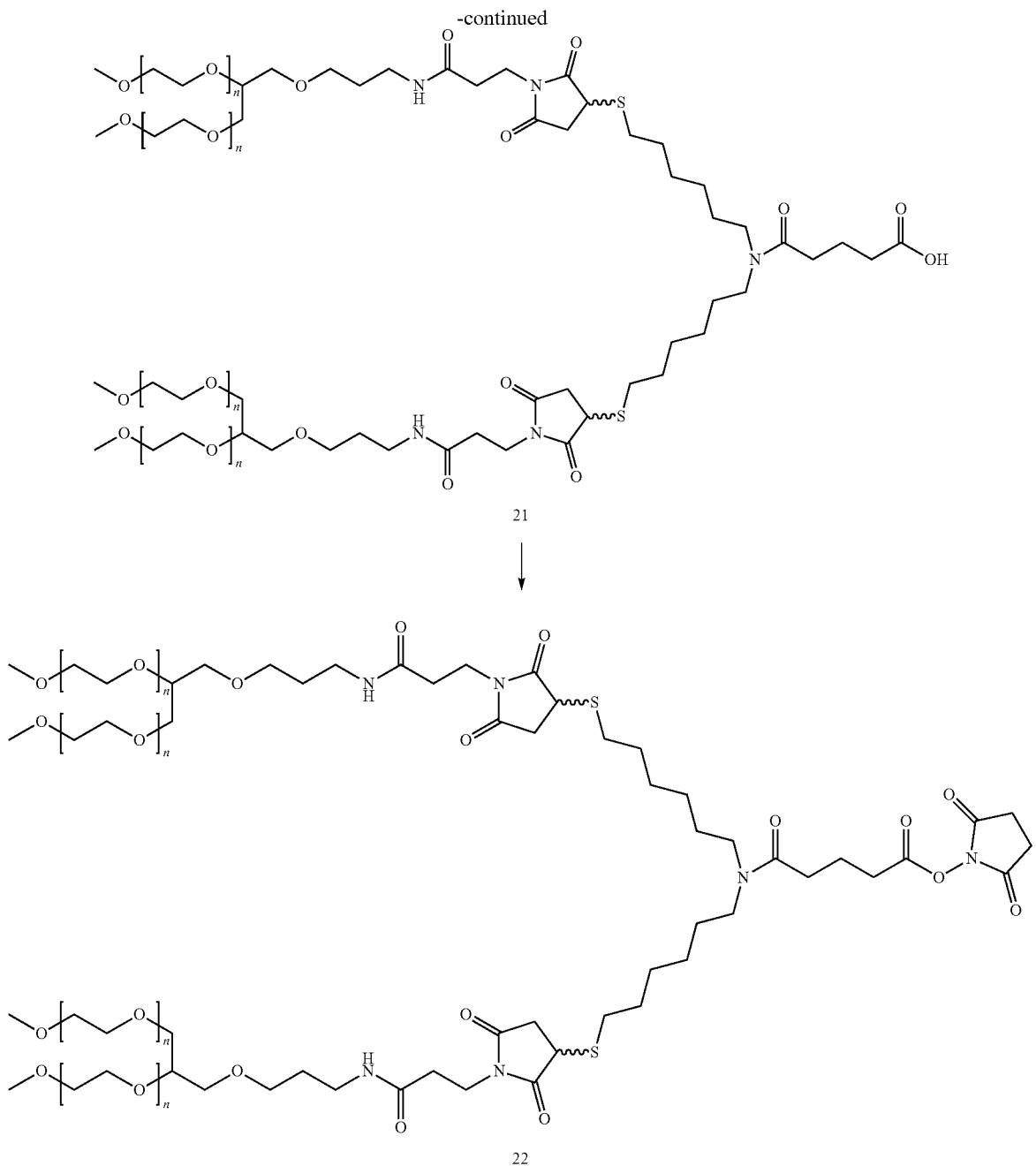

Acid 15 (12 mg, 14 µmol) was stirred in 1 ml. TFA, 1 ml. DCM, and 10 µL TES for 10 min at room temperature. The volatile components were removed in a nitrogen stream and the dithiol 20 was purified by RP-HPLC.

20: Yield 2.9 mg (8 µmol)

MS [M+Na]⁺=386.8 (MW+Na calculated=386.2 g/mol)

20 (1 mg, 2.8 µmol) in 170 µL acetonitrile was added to mPEG-maleimide 1B (NOF, Japan) (380 mg, 9.2 µmol) in 4 ml. 1/1 (v/v) acetonitrile/water+0.1% TFA. 200 µL of 0.5 M phosphate buffer pH7.4 were added and the mixture was reacted for 10 min at room temperature. 0.6 µL (7.8 µmol) mercaptoethanol were added and the reaction mixture was acidified to pH 4-5 by addition of TFA. The buffer was exchanged to 0.005% HCl (HiPREP Desalting column, 26/10 GE healthcare) and 21 was lyophilized without further purification.

21: Yield 320 mg 21 was dissolved in 50 ml. of toluene and the polymer solution was azeotropically dried for two hours under reflux using a Dean-Stark trap. The polymer solution was then cooled to room temperature. The dried mPEG-linker reagent 21 was precipitated by addition of chilled ether (60 mL).

dicyclohexylcarbodiimide (1.2 mg, 6 µmol) in DCM was added to a solution of 21 (240 mg, 3 µmol) and N-hydroxysuccinimide (0.7 mg, 6 µmol) in DCM (3 mL). The reaction mixture was stirred for 14 h at room temperature and 22 was precipitated by addition of cold ether (20 mL). Product 22 was dried in vacuo.

22: Yield 200 mg

Example 10: Synthesis of Permanent Amide-Linked mPEG-hGH Monoconjugate 23 and mPEG$_2$-hGH Bisconjugate 24 Using Linear 40 kDa mPEG-Succinimidyl Hexanoate Derivative

Figure 1:
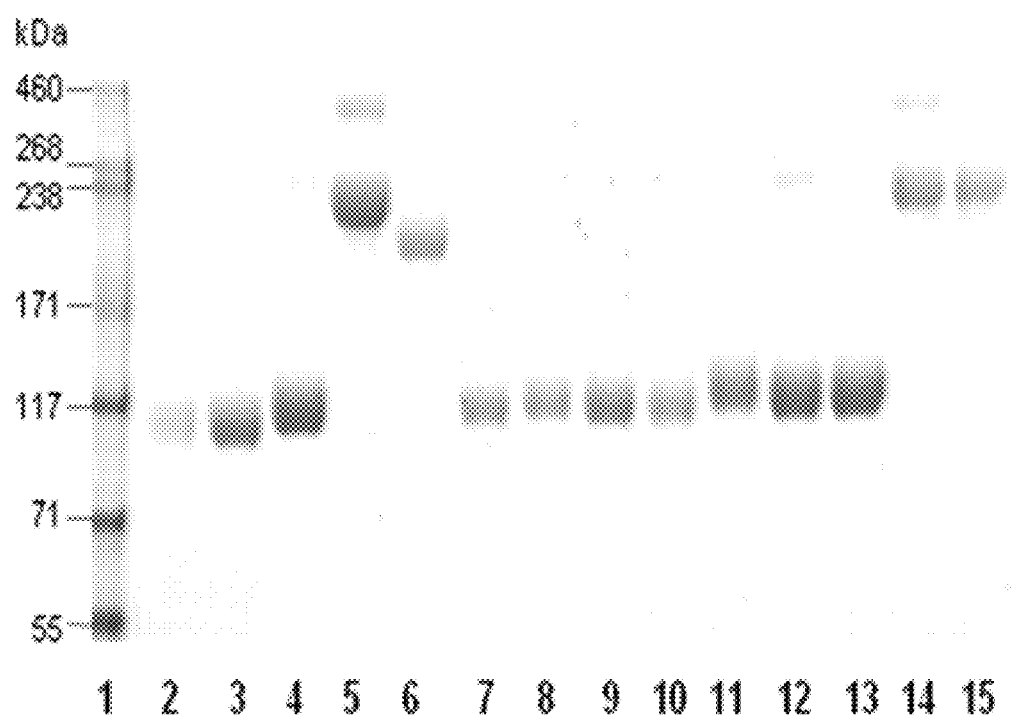

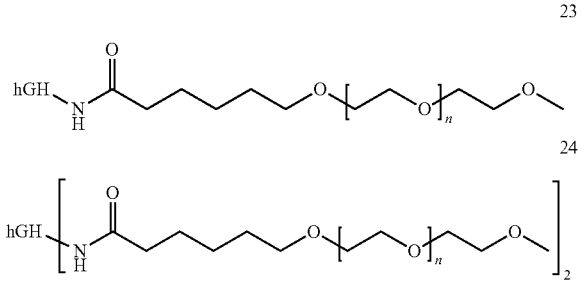

hGH was buffer exchanged to 50 mM sodium borate pH 8.5 (alternatively sodium borate pH 8 or sodium borate pH 9 can be used). The concentration of hGH was approximately 2.5 mg/ml. A three-fold molar excess of 40 kDa mPEG-succinimidyl hexanoate derivative (NOF, Japan) relative to the amount of hGH was dissolved in water to form a 20% (w/v) reagent solution (alternatively a four-fold or five-fold molar excess can be used). The reagent solution was added to the hGH solution and mixed. The reaction mixture was incubated for 2 h at room temperature and quenched with hydroxylamine at room temperature and pH 7 for two hours. The quenched reaction mixture was analyzed by size exclusion chromatography. The monoconjugate 23 and bisconjugate 24 were purified by cation exchange chromatography. Alternatively, anion exchange chromatography can be used for purification. The purified conjugates were analyzed by SDS-PAGE (FIG. 1).

Example 11: Synthesis of Permanent Amide-Linked mPEG-hGH Monoconjugate 25 and mPEG-hGH Bisconjugate 26 Using Branched 40 kDa mPEG-NHS Ester Derivative

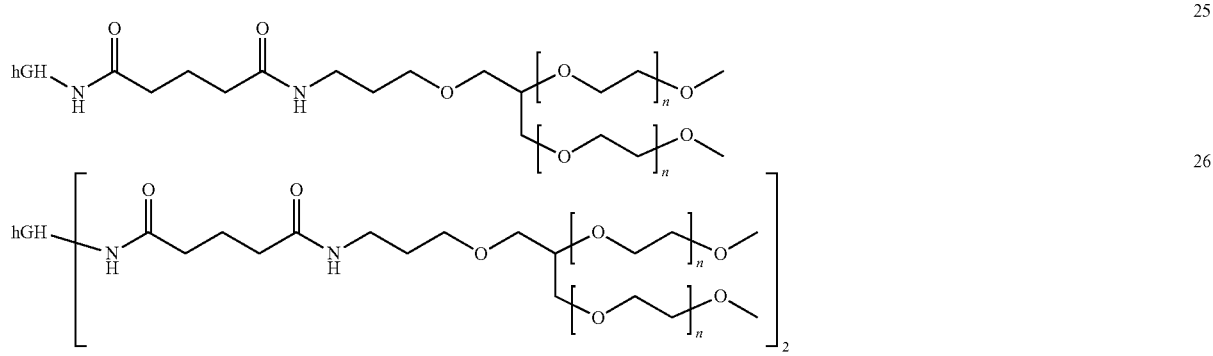

Permanent mPEG-hGH monoconjugate 25 and bisconjugate 26 were synthesized according to the procedure described in Example 10 using branched 40 kDa mPEG-NHS ester derivative (NOF, Japan). The purified conjugates were analyzed by SDS-PAGE (FIG. 1).

Example 12: Synthesis of Permanent Amide-Linked mPEG-hGH Monoconjugate 27 Using 4-Arm Branched 80 kDa mPEG-NHS Ester Derivative

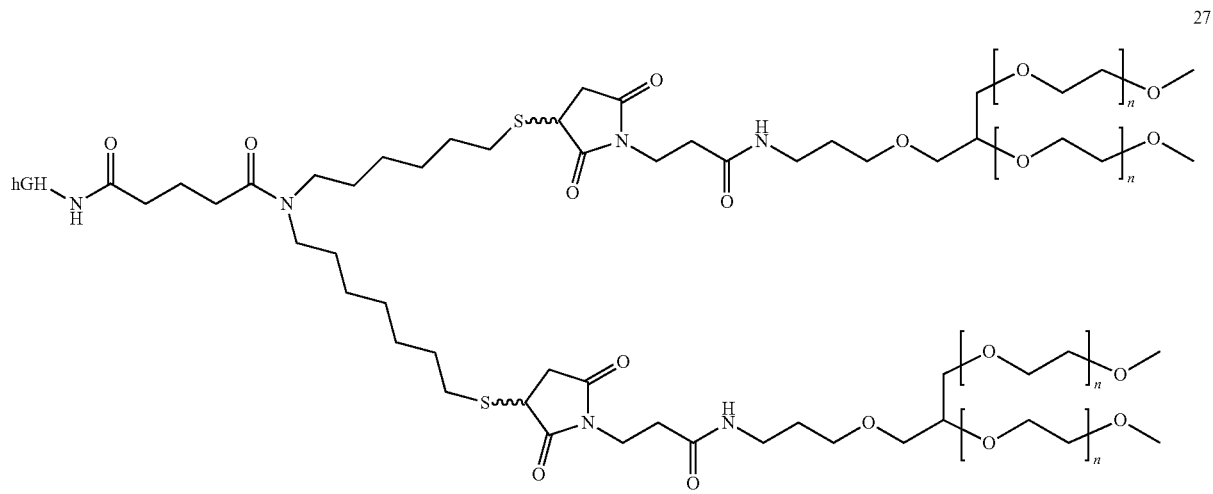

Permanent mPEG-hGH monoconjugate 27 was described according to Example 10 using 4-arm branched 80 kDa mPEG-NHS ester derivative 22. Purified 27 was analyzed by SDS-PAGE (FIG. 1).

Example 13: Synthesis of Permanent Carbamate-Linked mPEG-hGH Monoconjugate 28 Using 4-Arm Branched 40 kDa mPEG-Pentafluorophenylcarbonate Derivative 17aa

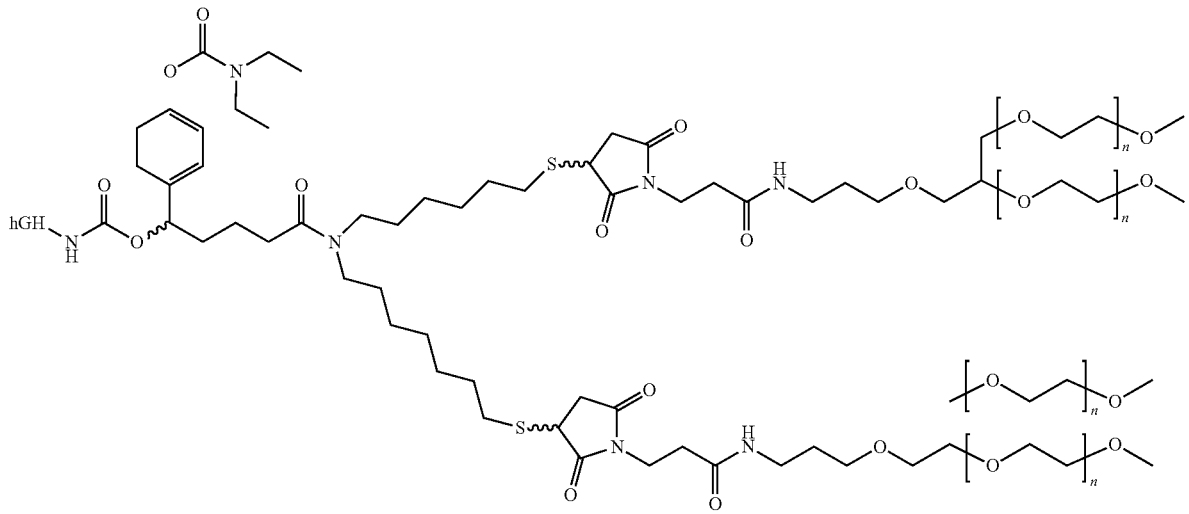

Figure 2:
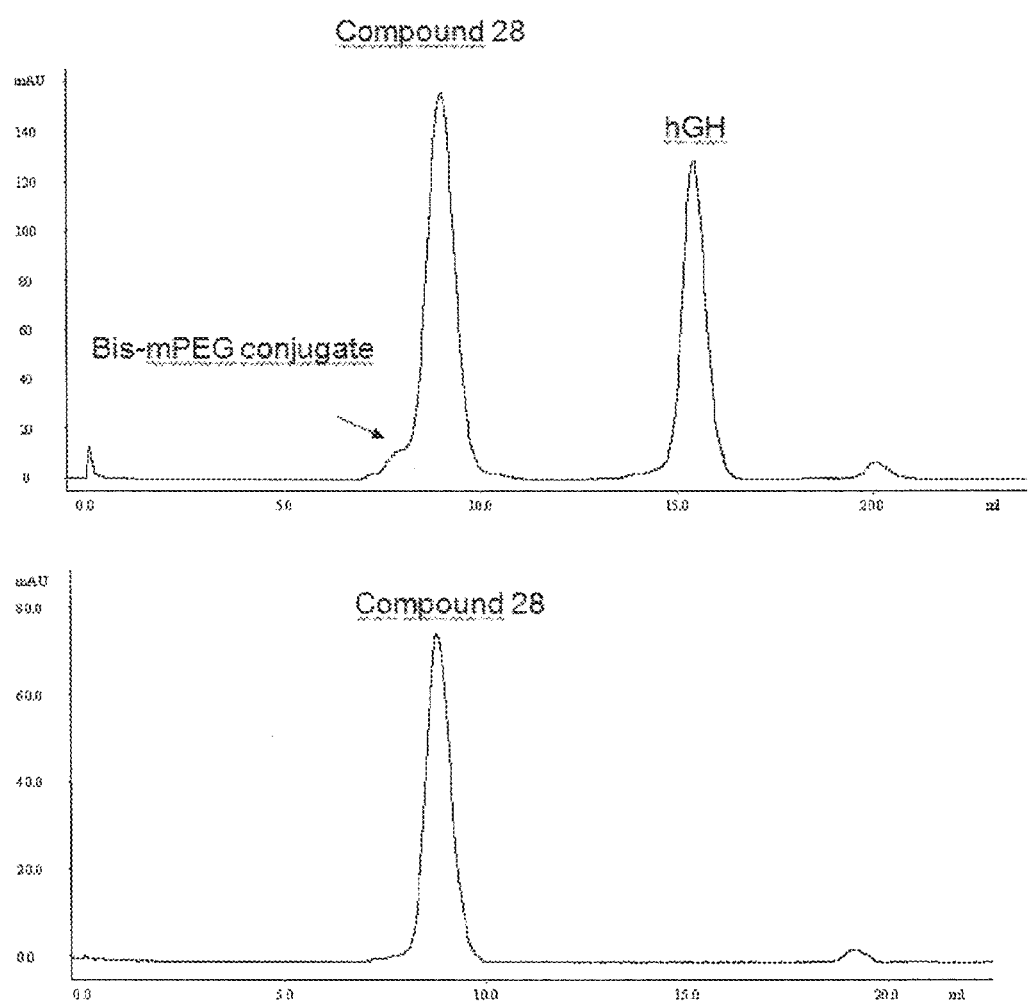
FIG. 2 shows size exclusion chromatogram of quenched reaction solution of the synthesis of conjugate 28 and size exclusion chromatogram of purified 28

28 hGH was buffer exchanged to 50 mM sodium borate pH 9 (alternatively sodium borate pH 8.5 or sodium borate pH 8 can be used). The concentration of hGH was approximately 2.5 mg/ml. A four-fold molar excess of permanent 4-arm branched 40 kDa mPEG-linker reagent 17aa relative to the amount of hGH was dissolved in water to form a 20% (w/v) reagent solution. The reagent solution was added to the hGH solution and mixed. The reaction mixture was incubated for 1.5 h at room temperature and quenched by incubating in 100 mM hydroxylamine at pH 7 and room temperature for 2 h. The quenched reaction mixture was analyzed by size exclusion chromatography (FIG. 2 top). Permanent mPEG-linker-hGH monoconjugate 28 was purified by anion exchange chromatography at pH 7.5 and analyzed by SDS-PAGE (FIG. 1) and size exclusion chromatography (FIG. 2 bottom).

Example 14: Synthesis of Permanent Carbamate-Linked mPEG-hGH Monoconjugate 29 Using 4-Arm Branched 80 kDa mPEG-Pentafluorophenylcarbonate Derivative

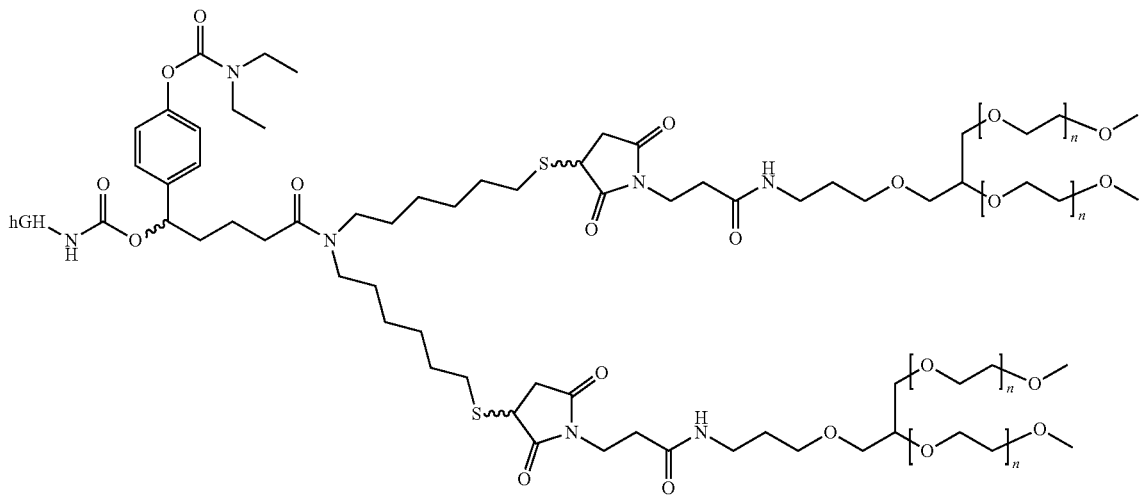

29

Permanent carbamate-linked mPEG-hGH monoconjugate 29 was synthesized according to Example 13 using 4-arm branched 80 kDa mPEG-pentafluorophenyl carbonate derivative 17ab. Purified 29 was analyzed by SDS-PAGE (FIG. 1).

Example 15: Synthesis of Permanent Carbamate-Linked mPEG-hGH Monoconjugate 30 Using 4-Arm Branched 40 kDa mPEG-Pentafluorophenylcarbonate Derivative 17Ac

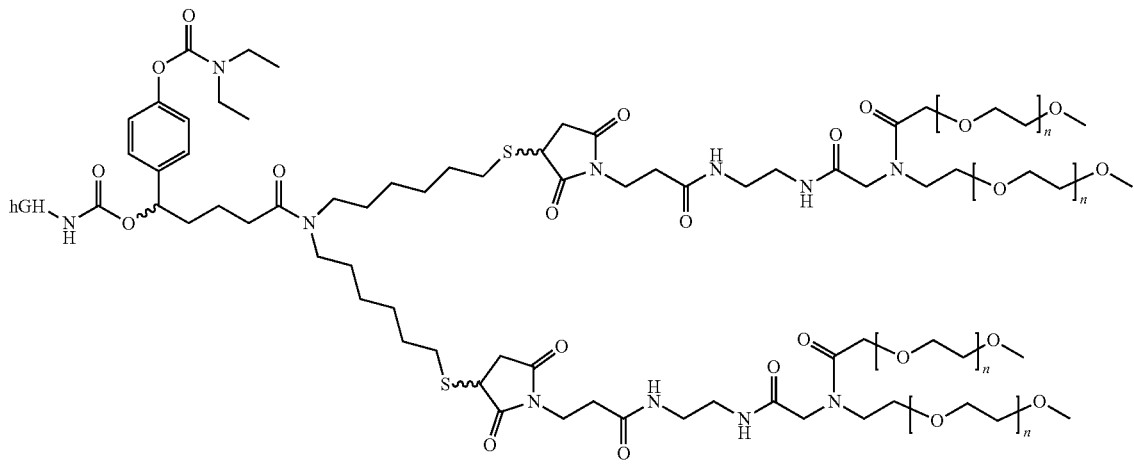

30

Permanent mPEG-hGH monoconjugate 30 was synthesized according to Example 13 using 4-arm branched 40 kDa mPEG-pentafluorophenyl carbonate derivative 17ac. Purified 30 was analyzed by SDS-PAGE (FIG. 1).

Example 16: Synthesis of Permanent mPEG-hGH Monoconjugate 31 Using 4-Arm Branched 80 kDa mPEG-Pentafluorophenylcarbonate Derivative

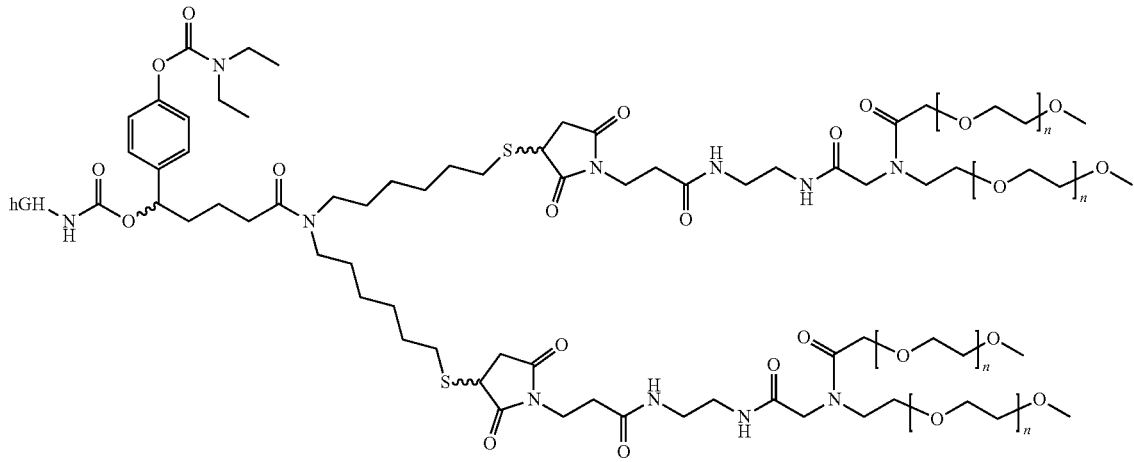

31

Permanent mPEG-hGH monoconjugate 31 can be synthesized according to Example 13 using 4-arm branched 80 kDa mPEG-pentafluorophenyl carbonate derivative 17ad.

Example 17: Synthesis of Permanent Carbamate-Linked mPEG-hGH Monoconjugate 32 Using 4-Arm Branched 40 kDa mPEG-Pentafluorophenylcarbonate Derivative

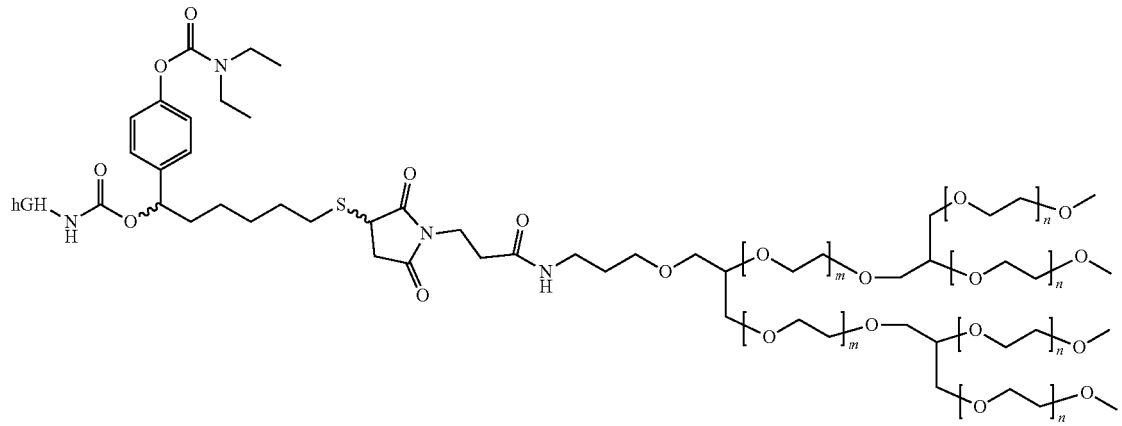

32

Permanent carbamate-linked mPEG-hGH monoconjugate 32 was synthesized according to Example 13 using 4-arm branched 40 kDa mPEG-pentafluorophenyl carbonate derivative 19aa. Purified 32 was analyzed by SDS-PAGE (FIG. 1).

Example 18: Synthesis of Permanent Carbamate-Linked mPEG-hGH Monoconjugate 33 Using 4-Arm Branched 80 kDa mPEG-Pentafluorophenylcarbonate Derivative

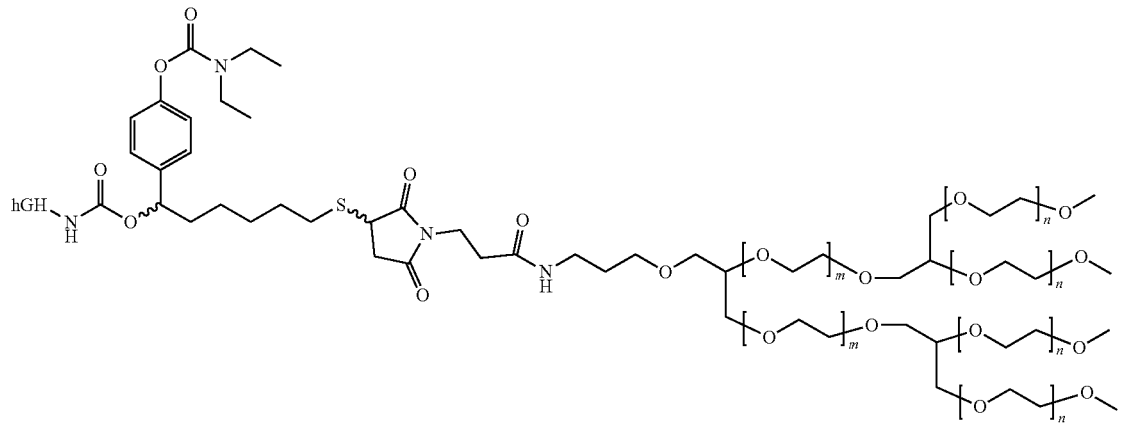

33

Permanent mPEG-hGH monoconjugate 33 was synthesized according to Example 13 using 4-arm branched 80 kDa mPEG-pentafluorophenyl carbonate derivative 19ab. Purified 33 was analyzed by SDS-PAGE (FIG. 1).

Example 19: Synthesis of Permanent Amine-Linked mPEG-hGH Monoconjugate 34 Using Branched 40 kDa mPEG-Propionaldehyde Derivative

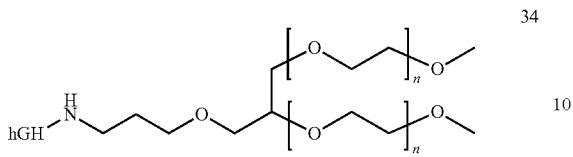

34 hGH was buffer exchanged to 50 mM MES buffer pH 6 (alternatively HEPES buffer pH 7 was used) and the concentration of hGH was adjusted to 1.5 mg/ml. A three-fold molar excess of 40 kDa mPEG-propionaldehyde (GL2-400AL3, NOF, Japan) relative to the amount of hGH was dissolved in water to form a 25% (w/v) reagent solution. The reagent solution was added to the hGH solution and mixed. An aliquot of a 1M stock solution of sodium cyanoborohydride in water was added to give a final concentration of 25 mM in the reaction mixture. The solution was incubated for 18 h at room temperature in the dark. The reaction was quenched by the addition of Tris buffer. The reaction mixture was analyzed by size exclusion chromatography and conjugate 34 was purified by cation exchange chromatography. Purified mPEG-hGH monoconjugate 34 was analyzed by SDS-PAGE (FIG. 1).

Example 20: Synthesis of Transient Carbamate-Linked mPEG-hGH Monoconjugate 35 Using Transient 4-Arm Branched 40 kDa mPEG-Pentafluorophenylcarbonate Derivative 19c

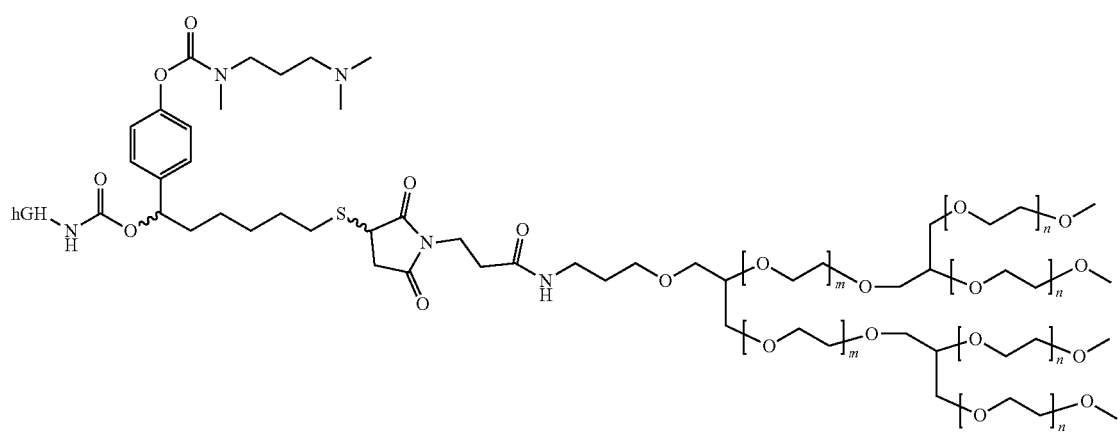

Figure 3:
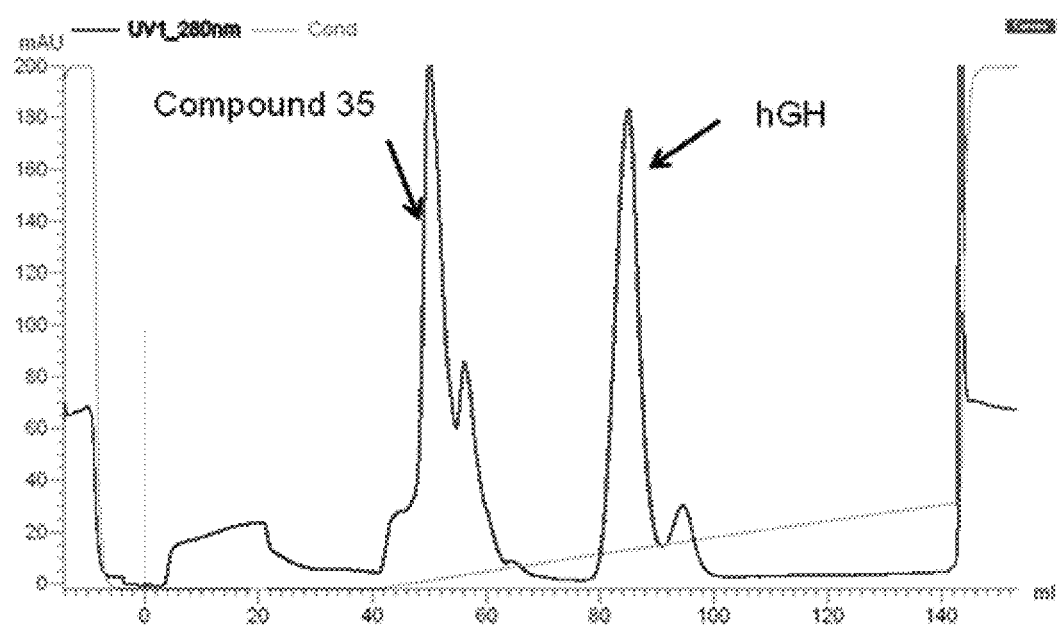
FIG. 3 shows cation exchange chromatography purification of conjugate 35 and size exclusion chromatogram of purified 35
Figure 3:
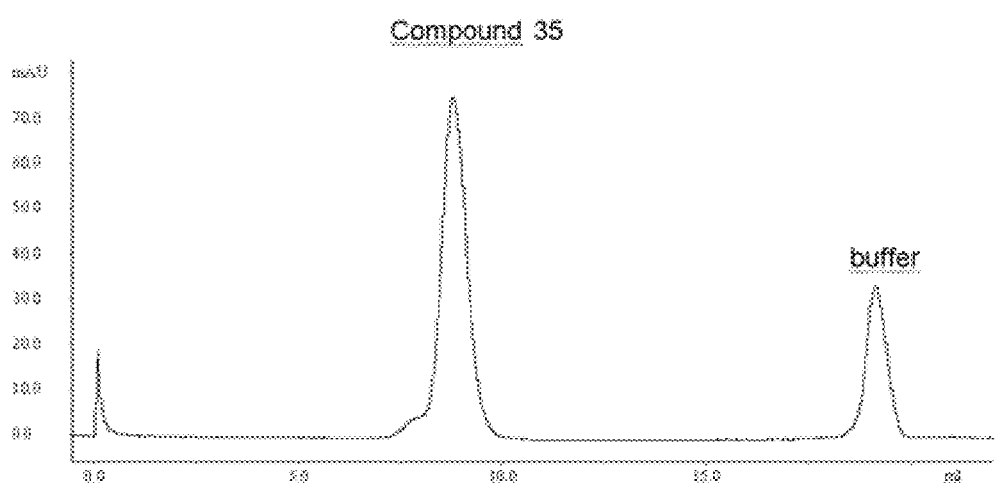

35 hGH was buffer exchanged to 50 mM sodium borate pH 9 (alternatively sodium borate pH 8.5 or sodium borate pH 8 can be used) and the concentration of hGH was adjusted to 2.5 mg/ml. A four-fold molar excess of transient mPEG-linker reagent 19c relative to the amount of hGH was dissolved in water to form a 20% (w/v) reagent solution. The reagent solution was added to the hGH solution and mixed. The reaction mixture was incubated for 1 h at room temperature and quenched by incubating in 100 mM hydroxylamine at pH 7 and room temperature for 2 h. mPEG-linker-hGH monoconjugate was purified by anion exchange chromatography at pH 6.5 (FIG. 3 top) and analyzed by size exclusion chromatography (FIG. 3 bottom).

Example 21: Synthesis of Transient mPEG-Linker-hGH Monoconjugate 36 Using 4-Arm Branched 80 kDa mPEG-Pentafluorophenylcarbonate Derivative

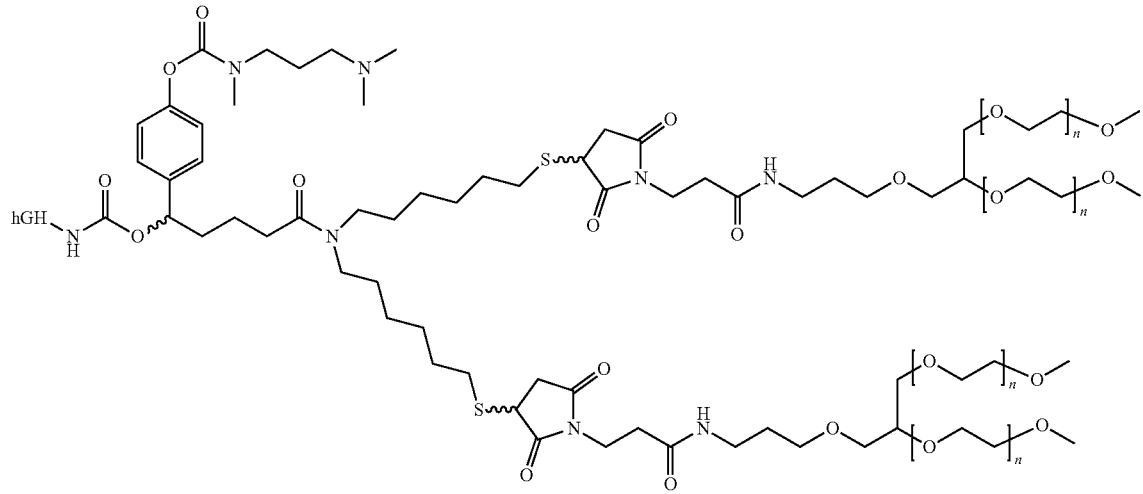

Figure 4:
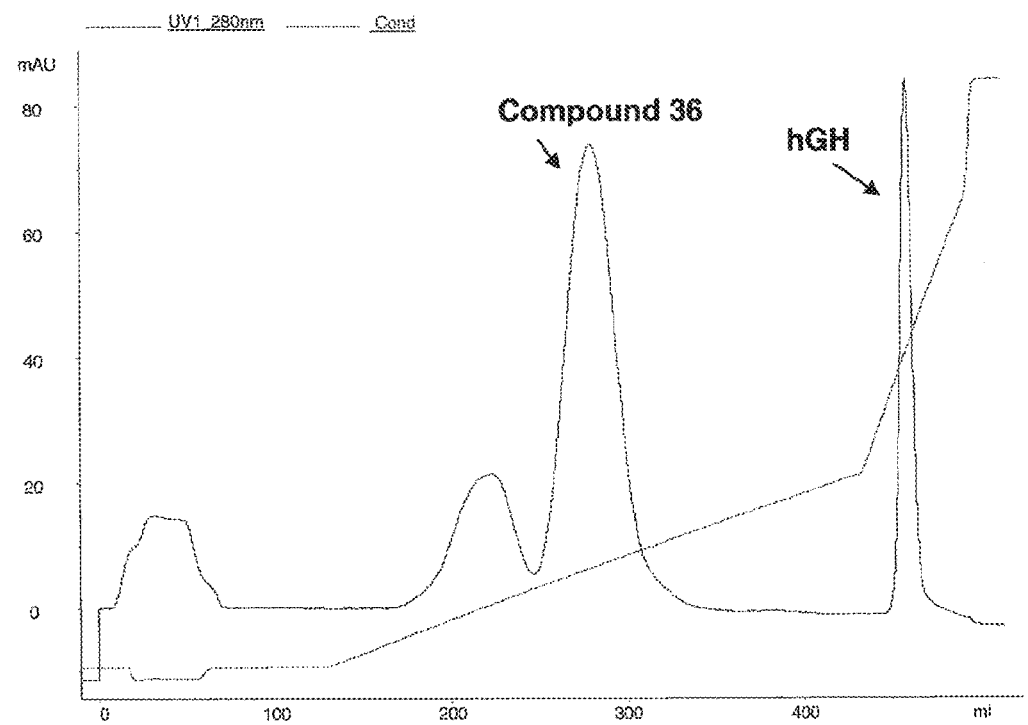
FIG. 4 shows cation exchange chromatography purification of conjugate 36 and size exclusion chromatogram of purified 36
Figure 4:
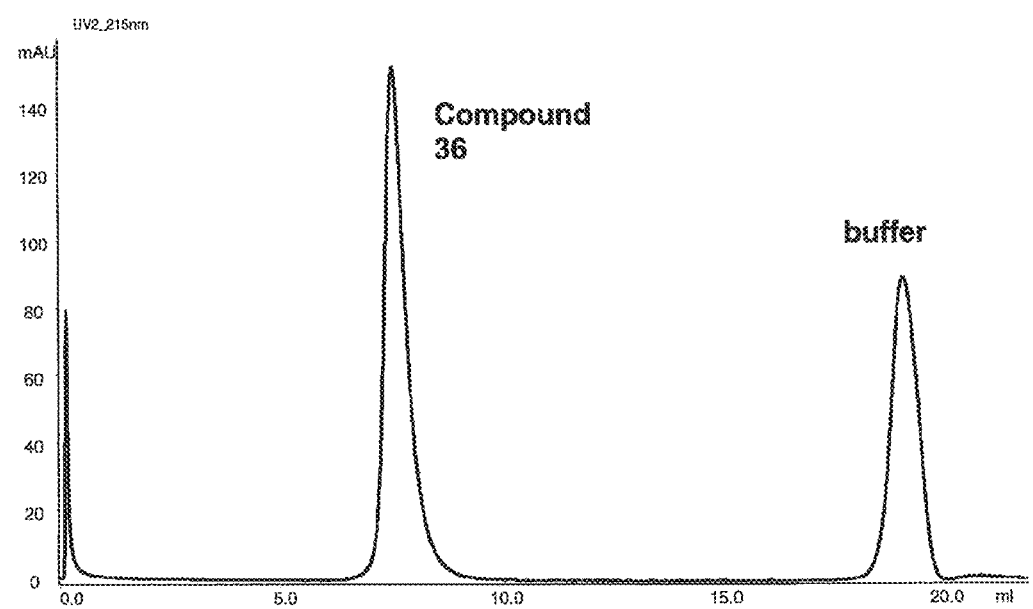

36 hGH was buffer exchanged to 100 mM sodium borate pH 9 (alternatively sodium borate pH 8.5 or sodium borate pH 8 can be used) and the concentration of hGH was adjusted to 10 mg/ml. A four-fold molar excess of transient 4-arm branched 80 kDa mPEG-linker reagent 17ca relative to the amount of hGH was dissolved in water to form a 25% (w/v) reagent solution. The reagent solution was added to the hGH solution and mixed. The reaction mixture was incubated for 45 min at room temperature and quenched by incubating in 100 mM hydroxylamine at pH 7 and room temperature for 2 h. mPEG-linker-hGH monoconjugate 36 was purified by cation exchange chromatography (FIG. 4 top) and analyzed by size exclusion chromatography (FIG. 4 bottom).

Example 22: Synthesis of Transient mPEG-hGH Monoconjugate 37 Using 4-Arm Branched 80 kDa mPEG-Pentafluorophenylcarbonate Derivative 17cb

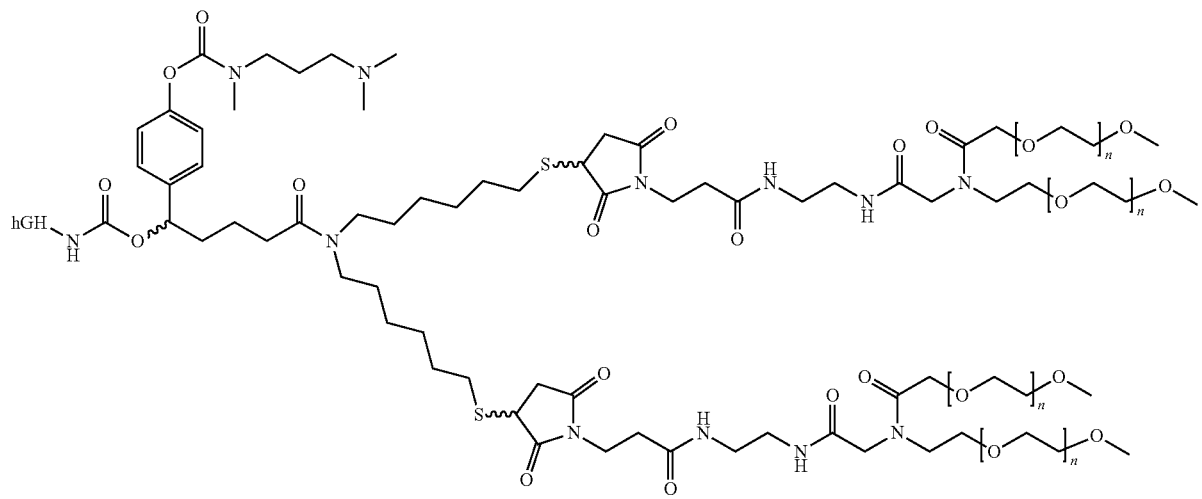

37

PEG-linker-hGH conjugate 37 was synthesized as described according to the procedure described in Example 21 using activated mPEG-linker reagent 17cb.

Figure 5:
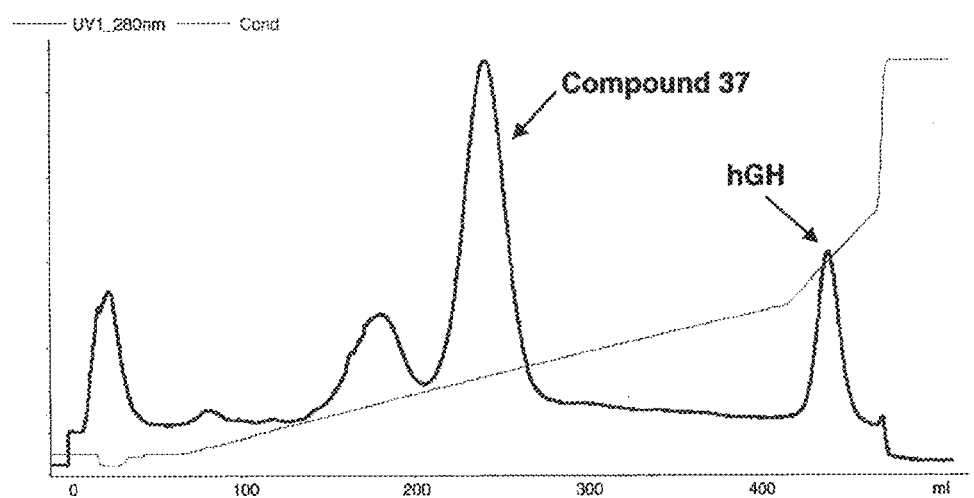
FIG. 5 shows cation exchange chromatography purification of conjugate 37 and size exclusion chromatogram of purified 37
Figure 5:
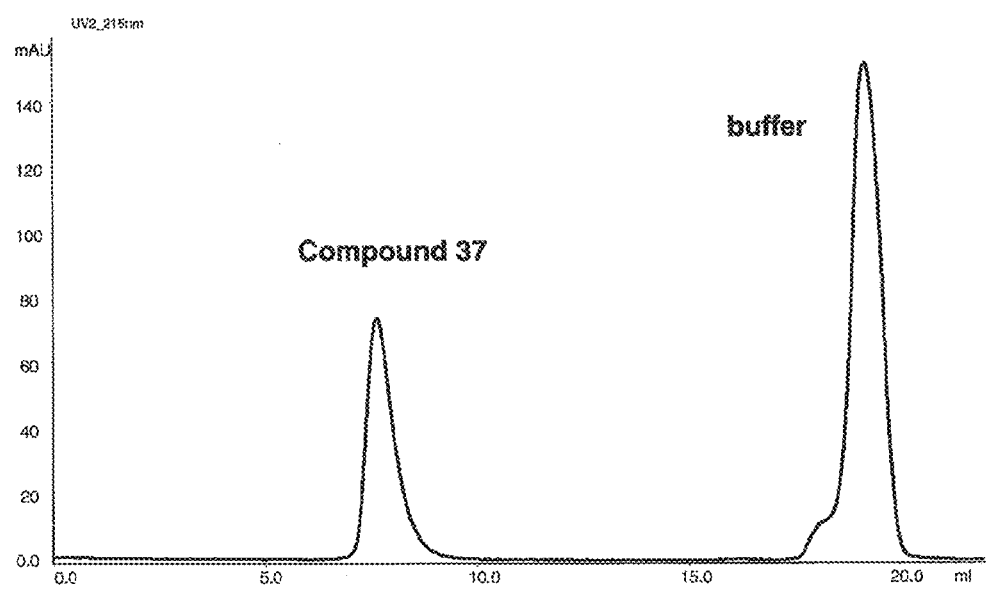

The cation exchange chromatogram and analytical size exclusion chromatogram are shown in FIG. 5 top and bottom, respectively.

Example 23: Synthesis of Transient Carbamate-Linked mPEG-hGH Monoconjugate 38 Using 4-Arm Branched 80 kDa mPEG-Pentafluorophenylcarbonate Derivative 17b

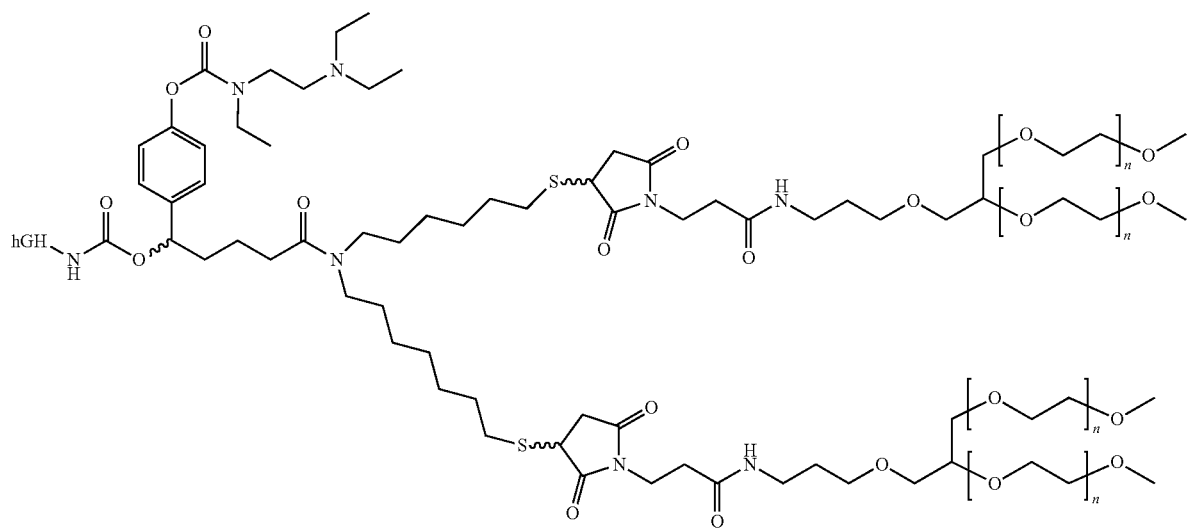

38

Transient carbamate-linked mPEG-linker-hGH conjugate 38 can be synthesized as described in Example 21 using transient 4-arm branched 80 kDa mPEG-linker reagent 17b.

Example 24: Assay to Measure hGH PEGylated Prodrug and hGH Activity

It is routine work for the skilled person to determine the residual activity of the polymeric prodrug as expressed by the activity of the corresponding permanent polymer conjugate using standard assays as described in example 1.

Specifically, NB2-1 1 cells were grown in serum free media with 100 ng/ml hGH supplement. For the in vitro proliferation assay, cell suspension containing $2 \times 10^5$ cells/ml were washed twice with serum free and hGH free medium and dispensed into a 96-well flat bottom microtitre plate ($10^4$ cells/well). Compounds were tested in triplicate in a series of titration steps (9 steps, using a factor 3 dilution between each step). The cells with compound solutions were incubated for 48 hours followed by incubation for 2.5 hours with cell proliferation reagent WST-1. NB2-1 1 proliferation was determined by optical density reading in an ELISA reader and the response plotted as a function of concentration and EC50 values determined. The results are shown as % residual in vitro bioactivity in relation to unmodified hGH is provided in table 1.

In the in vitro experiments as described above, native hGH (source Novo Nordisk, Denmark) was used as reference compound. The same hGH preparation was used for the synthesis of the permanent PEG-hGH conjugates.

TABLE 1

Table 1: In vitro bioactivity of permanently PEGylated hGH conjugates as compared to native hGH (Norditropin, Novo Nordisk, Denmark).

| Compound | In vitro characterization: In vitro activity of permanent conjugates |
|---|---|
| Native hGH (hGH, Novo Nordisk, Denmark) | 100% |
| 23 | 10.3% |
| 24 | 0.4% |
| 25 | 4.4% |
| 26 | 0.2% |
| 27 | 0.7% |
| 28 | 2.3% |
| 29 | 0.7% |
| 30 | 2.0% |
| 32 | 6.3% |
| 33 | 2.2% |
| 34 | 4.8% |

Table 1: In vitro bioactivity of permanently PEGylated hGH conjugates as compared to native hGH (Norditropin, Novo Nordisk, Denmark).

Conclusion:

As seen from table 1, by conjugation of a suitable PEG molecule to hGH, the in vitro activity of the PEGylated hGH can be reduced to less than 5% of the activity of the native unconjugated hGH. For example, conjugation of a branched PEG 4×20 kDa to hGH reduces the residual activity to 0.7% of the unconjugated hGH standard.

Furthermore, from these results it was also surprisingly discovered, that the residual activity of the PEGylated growth hormone is related not only to the size of the attached PEG, but also to the degree of branching and the spacing between the hGH and the branching points within the PEG structure.

Linear PEG

Specifically, attachment of a 40 kDa linear PEG to hGH results in an in vitro activity of 10.3% (compound 23) compared to native hGH.

Branched PEG

When a branched 2×20 kDa PEG is attached (compound 25), the in v/fro activity is further reduced to 4.4% compared to native hGH.

Further, when a 4×20 kDa PEG with a short spacing between the hGH and the branching points within the PEG reagent is attached (compound 27 and 29) the in vitro activity is even further reduced to respectively 0.7% compared to native hGH.

Surprisingly, when a 4×20 kDa PEG with a relative long spacer between the human growth hormone and the first branching point within the PEG reagent is attached (e.g. compound 33) the in vitro activity is less reduced (2.2%) showing the importance of the spacer between the hGH functional group and the first branching point within the branched PEG reagent.

Conjugation of more than one PEG moiety to the hGH to form bisPEG-conjugates reduces the in vitro activity to lower than 0.5%. (e.g. compound 24 and 26).

Example 25: Determination of In Vitro Autocleavage Rate of Conjugate 35, 36, 37, and 38

Figure 6:
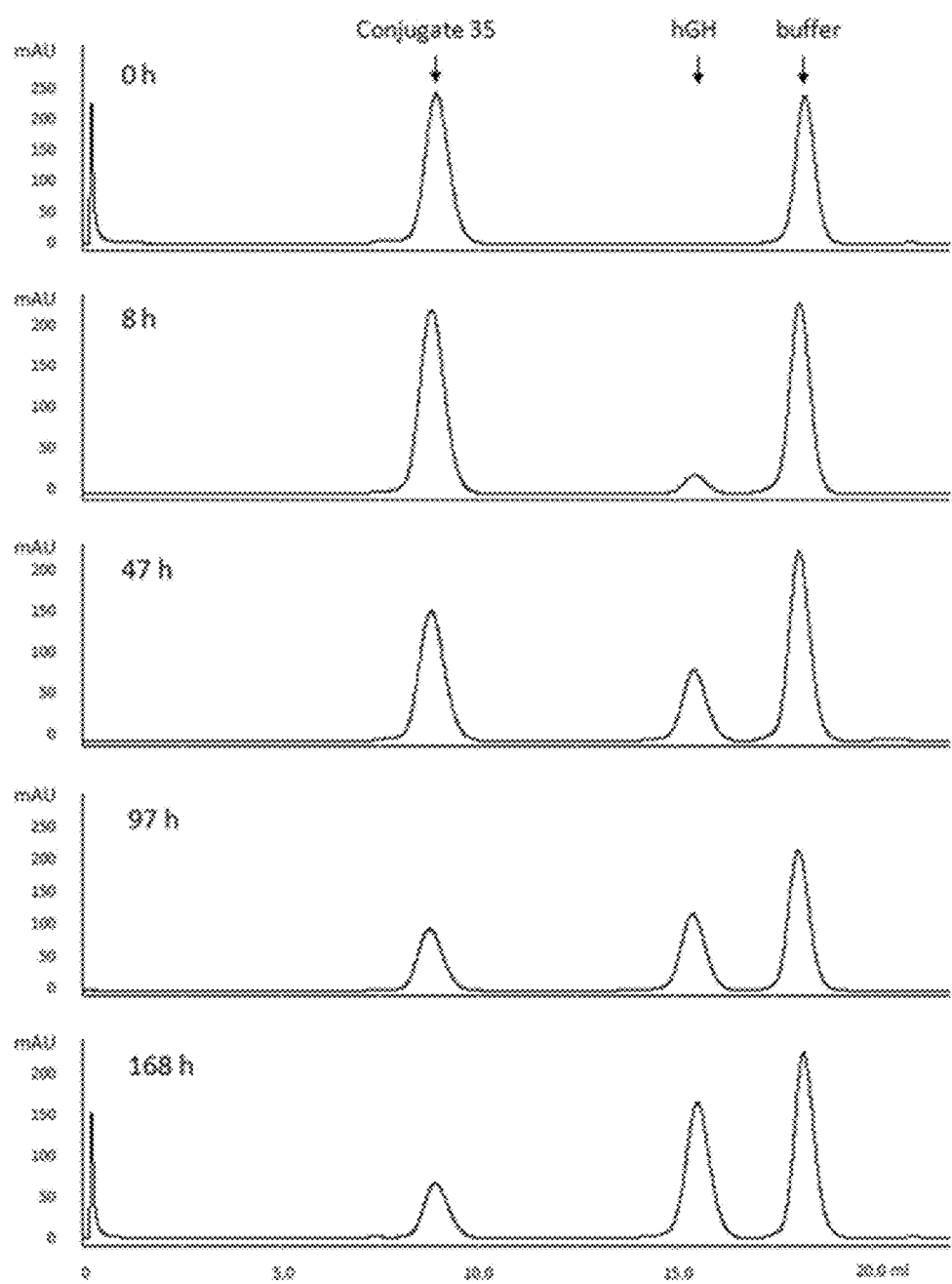
FIG. 6 shows size exclusion chromatograms of samples of conjugate 35 incubated in buffer at pH 7.4 and 37° C. at various time points

The autocleavage rate of conjugate 35, 36 and 37 at pH 7.4 and 37° C. was determined as described in Example 2. Autocleavage half-lives of approximately 75 h were determined for these conjugates. FIG. 6 shows size exclusion chromatograms of samples of incubated 35 analyzed after 0 h, 8 h, 47 h, 97 h, and 168 h showing slow release of hGH from conjugate 35 over time. Autocleavage rate of conjugate 38 can be determined accordingly and give half-lives of ca. 50 h.

Example 26: Assay to Measure Terminal In Vivo Half Life of the hGH PEGylated Prodrugs as Expressed by the Half Life of the Corresponding Permanent Conjugate In Vivo The pharmacokinetics of the permanent conjugates were determined after intravenous injection of 0.25 mg (hGH equivalents) into rats. In order to select a conjugate suitable for weekly injections in humans, a plasma half life of more than 10 hours in the rat is desirable.

A single dose of 0.25 mg hGH or 0.25 mg permanent PEG-hGH conjugate (dose based on hGH) per rat was administered intravenously to male Wistar rats (200-250 g). Two groups of two animals each were used for each compound. 200-300 µl whole blood was withdrawn sublingually to obtain 100 µl Ca-Heparin plasma per animal and time point. Samples were collected after 0.5, 3, 24, 48, 72 and 96 h for group 1 and after 5, 8, 32, 56, 80 and 168 h for group 2. Plasma samples were stored at −80° C. until assayed.

hGH and PEG-hGH conjugate concentrations were measured using a hGH ELISA kit (DSL). Plasma concentrations were calculated from a calibration curve of the respective conjugate or hGH and plotted against time, and the terminal half-life ($t_{1/2}$) was calculated using a single compartment model. The result of the half life determination is tabulated in table 2.

In order to select a conjugate suitable for weekly injections in humans pharmacokinetic studies in rats were performed. As the half life of PEGylated conjugates in rats are in the range of 5 times faster than in humans, the half life of a PEGylated hGH in rats should be about 10 hours or longer. In order to obtain an estimate of the half life of the conjugated hGH PEGylated prodrug without linker cleavage, the permanently conjugated corresponding conjugate is injected into rat.

The results of the in vivo half-life determinations are tabulated in Table 2.

TABLE 2

Table 2: Half life of permanent PEG-hGH conjugates in rats

| Compound | In vivo characterization: in vivo half-life of permanent conjugates |
| --- | --- |
| Native hGH (Novo Nordisk, Denmark) | 20 minutes |
| 23 | 4 hours |
| 25 | 5 hours |
| 26 | 11 hours |
| 27 | 13 hours |

Table 2: Half Life of Permanent PEG-hGH Conjugates in Rats

Conclusion:

From table 1 and table 2 it is obvious that residual activity correlates inversely with half life e.g. a high degree of residual activity causes faster elimination. This is typical for conjugates eliminated by receptor mediated clearance mechanisms.

Furthermore, in order to obtain a hGH PEGylated prodrug that can be administered once weekly in humans and with a low residual activity, a PEG molecule with one or more branching points and with a molecular weight of 40 kDa or above is preferred. Alternatively, conjugation of PEG to more than one site on hGH to form bisPEG-hGH conjugates results in a long terminal half-life.

Example 27 Pharmacodynamic Study of Transient Carbamate-Linked mPEG-Linker-hGH Conjugate 36 and Human Growth Hormone in Cynomolgus Monkeys The objective of this study was to compare the pharmacodynamic response in cynomolgus monkeys of one dose of transient carbamate-linked mPEG-linker-hGH conjugate 36 with once-daily human growth hormone dosing for one week.

The following dosing groups were studied:

| Test article | Dose | Dosing route | Dose occasion |
| --- | --- | --- | --- |
| Human growth hormone | 0.3 mg/kg/day | SC | Day 1, 2, 3, 4, 5, 6, 7 |
| Transient carbamate-linked mPEG-linker-hGH conjugate 36 | 5 mg/kg | SC | Day 1 |
| Transient carbamate-linked mPEG-linker-hGH conjugate 36 | 10 mg/kg | SC | Day 1 |
| Vehicle (10 mM succinic acid, 92 mg/mL trehalose, pH 4.0) | 0 mg/kg | SC | Day 1 |

Since transient carbamate-linked mPEG-linker-hGH conjugate 36 is transiently PEGylated using a 80 kDa PEG group, the hGH amounts in the 5 and 10 mg/kg transient carbamate-linked mPEG-linker-hGH conjugate 36 dosing groups were approximately 1 and 2 mg/kg, respectively. Hence, the hGH amount in the 10 mg/kg group of transient carbamate-linked mPEG-linker-hGH conjugate 36 was equivalent to a daily dose of 0.3 mg/kg hGH.

Each test article was injected subcutaneously into 2 cynomolgus monkeys (1 male, 1 female) using a dose volume of 1 ml/kg. The age and weight of the animals were 2.5-3 years and 2.0-2.5 kgs, respectively.

Blood samples were collected from the femoral artery/vein for determination of serum concentrations of IGF-1, a pharmacodynamic marker for human growth hormone. The blood sample were collected at the following timepoints: 0 (predose), 3, 6, 12, 24, 36, 48, 72, 96, 120, and 144 hours after dosing on Day 1

Blood samples were collected, allowed to clot, and then stored on an ice block or wet ice until centrifuged. After centrifugation, the serum samples were aliquoted into pre-labeled vials and tightly capped. The vials were stored at −70° C. upon aliquoting into vials.

IGF-1 levels in the serum samples were measured using the Quantikine Human IGF-1 ELISA kit (R&D systems) that had been adapted and validated for use in determining IGF-1 levels in cynomolgus monkey serum.

Figure 11:
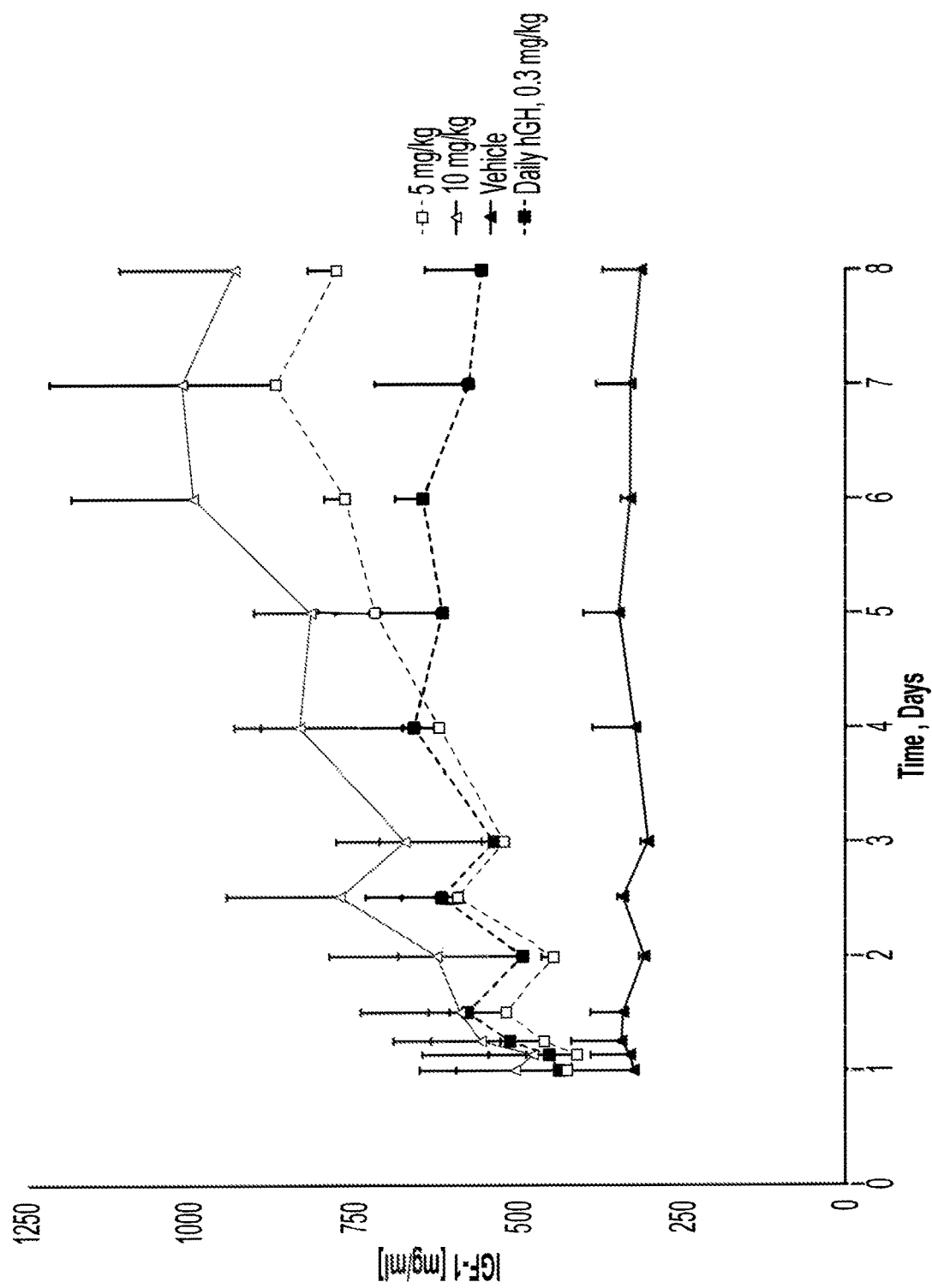
FIG. 11 shows pharmacodynamic response curves of conjugate 36.

The pharmacodynamic response of the test articles is shown on FIG. 11. Both daily hGH administration and one administration of transient carbamate-linked mPEG-Linker-hGH conjugate 36 increased the IGF-1 levels over the levels measured in the vehicle group. One administration of 5 mg/kg transient carbamate-linked mPEG-Linker-hGH conjugate 36 was equivalent to daily hGH administration while one administration of 10 mg/kg transient carbamate-linked mPEG-linker-hGH conjugate 36 was shown to be superior to daily hGH. This clearly indicated that a once-weekly dose of transient carbamate-linked mPEG-linker-hGH conjugate 36 was superior to an equivalent daily dose of hGH.

Abbreviations

DBU 1,3-diazabicyclo[5.4.0]undecene
DCM dichloromethane
DIEA diisopropylethylamine
DMAP dimethylamino-pyridine
DMF N,N-dimethylformamide
DMSO dimethylsulfoxide
eq stoichiometric equivalent
fmoc 9-fluorenylmethoxycarbonyl
HFIP hexafluoroisopropanol
HOSu N-hydroxysuccinimide
LCMS mass spectrometry-coupled liquid chromatography
Mal maleimidopropionyl
MS mass spectrum
MW molecular mass
PEG polyethylene glycol
RP-HPLC reversed-phase high performance liquid chromatography
Rt retention factor
r.t. room temperature
SEC size exclusion chromatography
Sue succinimidopropionyl
TES triethylsilane
TFA trifluoroacetic acid
THF tetrahydrofurane
Trt trityl

REFERENCE LIST

1. Büyükgebiz A. et al J. Pediatr. Endocrinol. Metab. 1999 January-February; 12(1):95-7
2. Clark et al, 1996, Journal of Biological Chemistry 271: 21969-21 977
3. Girard, J. Mehls, O., J. Clin Invest. 1994 March; 93(3): 1163-1 171
4. Philip Harris et al. Horm. Res. 2006; 65 (suppl. 4): 1-213, CF1-98 GH/IGF Treatment with title "First in-human study of PEGylated recombinant human growth hormone".
5. Veronese, F. M. "Enzymes for Human Therapy: Surface Structure Modifications," Chimica Oggi, 7:53-56 (1989).

The invention claimed is:

1. A method of treating a growth hormone (GH) related disease, wherein the method comprises administering once weekly an effective amount of a prodrug conjugate of the human growth hormone (hGH) to a patient having a GH related disease and wherein the prodrug conjugate of the human growth hormone (hGH) is of formula (AA)

hGH-NH-L$^a$-S$^0$      (AA), wherein hGH-NH represents the hGH residue;

L$^a$ represents a functional group, which is self hydrolysable (auto-cleavable) by an auto-cleavage inducing group Ga; and S$^0$ is a polymer chain having a molecular weight of at least 5 kDa and comprising an at least first branching structure BS$^1$, the at least first branching structure BS$^1$ comprising an at least second polymer chain S$^1$ having a molecular weight of at least 4 kDa, wherein at least one of S$^0$, BS$^1$, S$^1$ further comprises the auto-cleavage inducing group G$^a$ and wherein the branching structure BS$^1$ further comprises an at least third polymer chain S$^2$ having a molecular weight of at least 4 kDa or at least one of S$^0$, S$^1$ comprises an at least second branching structure B S 2 comprising the at least third polymer chain S$^2$ having a molecular weight of at least 4 kDa and wherein the molecular weight of the prodrug conjugate without the hGH-NH is at least 25 kDa and at most 1000 kDa.

2. The method of claim 1, wherein the molecular weight of the prodrug without the hGH-NH is at least 30 kDa and at most 120 kDa.

3. The method of claim 1, wherein the molecular weight of the prodrug without the hGH-NH is at least 40 kDa and at most 100 kDa.

4. The method of claim 1, wherein the molecular weight of the prodrug without the hGH-NH is at least 40 kDa and at most 90 kDa.

5. The method of claim 1, wherein L$^a$ is selected from the group consisting of and C(O)—O—, and C(O)—, which form together with the primary amino group of hGH a carbamate or amide group resulting in formula (AA1) or (AA2)

hGH-NH—C(O)O—S$^0$      (AA1),

hGH-NH—C(O)—S$^0$      (AA2).

6. The method of claim 1, wherein L$^a$ forms together with the amino group of hGH a carbamate functional group, the cleavage of said group is induced by a hydroxyl or amino group of G$^a$ via 1,4- or 1,6 benzyl elimination of S$^0$, wherein G$^a$ contains ester, carbonate, carbamate, or amide bonds that undergo rate-limiting transformation.

7. The method of claim 1, wherein $G^a$ is an aromatic ring or fluorenylmethyl directly attached to a carbamate functional group formed by $L^a$ and the primary amino group of hGH.

8. The method of claim 1, wherein at least one of the branching structures $BS^1$, $BS^2$ comprises a further fourth polymer chain $S^3$ having a molecular weight of at least 4 kDa or one of $S^0$, $S^1$, $S^2$ comprises a third branching structure $BS^3$ comprising the at least fourth polymer chain $S^3$ having a molecular weight of at least 4 kDa.

9. The method of claim 1, wherein the at least three chains $S^0$, $S^1$, $S^2$ are independently based on a polymer selected from the group consisting of polyalkyloxy polymers, hyaluronic acid and derivatives thereof, polyvinyl alcohols, polyoxazolines, polyanhydrides, poly(ortho esters), polycarbonates, polyurethanes, polyacrylic acids, polyacrylamides, polyacrylates, polymethacrylates, polyorganophosphazenes, polysiloxanes, polyvinylpyrrolidone, polycyanoacrylates, and polyesters.

10. The method of claim 1, wherein the at least three chains $S^0$, $S^1$, $S^2$ are based on a polyalkoxy polymer.

11. The method of claim 1, wherein the shortest distance between the attachment site of $S^0$ to $L^a$ and the first branching structure $BS^1$ measured as connected atoms is less than 50 atoms.

12. The method of claim 11, wherein the shortest distance is less than 20 atoms.

13. The method of claim 1, wherein $S^0$ is of formula (AAA1)

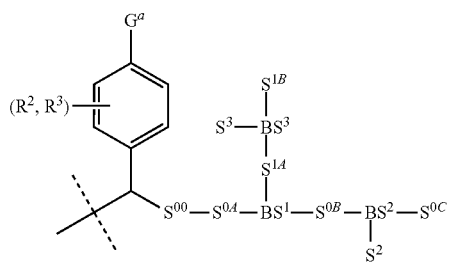

wherein
$G^a$ is an auto-cleavage inducing group;
$S^{00}$ is $CH_2$; or $C(O)$;
$S^{0A}$ is an alkylene chain having from 1 to 20 carbon atoms, which is optionally interrupted or terminated by one or more groups, cycles or heteroatoms selected from the group consisting of optionally substituted heterocycle; O; S; C(O); and NH;
$BS^1$, $BS^2$, $BS^3$ are independently selected from the group consisting of N; and CH;
$S^{0B}$, $S^{1A}$ are independently an alkylene chain having from 1 to 200 carbon atoms, which is optionally interrupted or terminated by one or more groups, cycles or heteroatoms selected from the group consisting of optionally substituted heterocycle; O; S; C(O); and NH;
$S^{0C}$, $S^{1B}$, are $(C(O))_{n2}(CH_2)_{n1}(OCH_2CH_2)_nOCH_3$, wherein each n is independently an integer from 100 to 500, each n1 is independently 0, 1, 2, 3, 4, 5, 6, 7, or 8, and n2 is 0 or 1;
$S^2$, $S^3$ are independently hydrogen; or $(C(O))_{n2}(CH_2)_{n1}(OCH_2CH_2)_nOCH_3$, wherein each n is independently an integer from 100 to 500, each n1 is independently 0, 1, 2, 3, 4, 5, 6, 7, or 8, and n2 is 0 or 1, provided that at least one of $S^2$, $S^3$ is other than hydrogen;

$R^2$, $R^3$ are selected independently from hydrogen, methyl, ethyl, propyl, isopropyl, butyl, iso-butyl, tertiary butyl.

14. The method of claim 1, wherein $G^a$ is OC(O)—R and R is of formula (I), which is

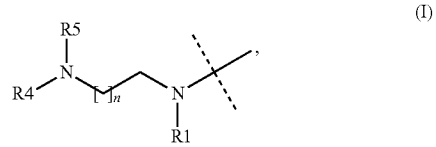

wherein R1, R4, R5 are selected independently from hydrogen, methyl, ethyl, propyl, isopropyl, butyl, isobutyl, tertiary butyl; and
n=1 or 2.

15. The method of claim 14, wherein R is selected from the group consisting of:

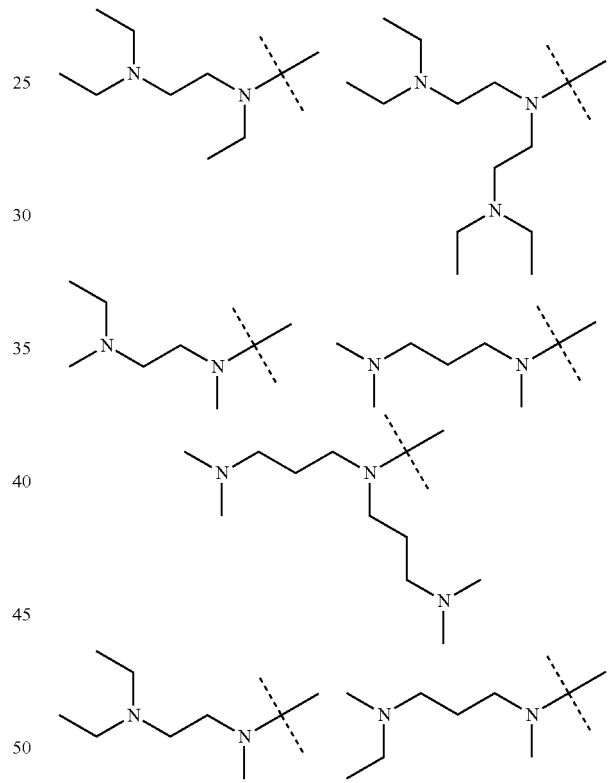

16. The method of claim 1, wherein $L^a$-$S^0$ is represented by formula (AAA2),

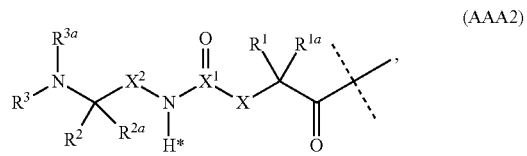

wherein the dashed line indicates the attachment to the primary amino group of hGH so that $L^a$ and the amino group form an amide bond;

X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;

$X^1$ is C; or S(O);

$X^2$ is $C(R^7, R^{7a})$; or $C(R^7, R^{7a})$—$C(R^8, R^{8a})$;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl; or optionally, one or more of the pairs $R^{1a}/R^{4a}$, $R^{1a}/R^{5a}$, $R^{4a}/R^{5}$, $R^{4a}/R^{5a}$, $R^{7a}/R^{8a}$ form a chemical bond;

optionally, one or more of the pairs $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-7}$ cycloalkyl; or 4 to 7 membered heterocyclyl;

optionally, one or more of the pairs $R^1/R^4$, $R^1/R^5$, $R^1/R^6$, $R^4/R^5$, $R^7/R^8$, $R^2/R^3$ are joined together with the atoms to which they are attached to form a ring A;

optionally, $R^3/R^{3a}$ are joined together with the nitrogen atom to which they are attached to form a 4 to 7 membered heterocycle;

A is selected from the group consisting of phenyl; naphthyl; indenyl; indanyl; tetralinyl; $C_{3-10}$ cycloalkyl; 4 to 7 membered heterocyclyl; and 9 to 11 membered heterobicyclyl; and wherein $S^0$ is substituted with one group $L^2$-Z and optionally further substituted, provided that the hydrogen marked with the asterisk in formula (I) is not replaced by a substituent; wherein $L^2$ is a single chemical bond or a spacer; and Z is of formula (AAA2a)

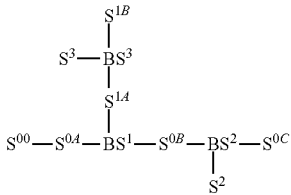

(AAA2a)

wherein $S^{00}$ is $CH_2$; or C(O);

$S^{0A}$ is an alkylene chain having from 1 to 20 carbon atoms, which is optionally interrupted or terminated by one or more groups, cycles or heteroatoms selected from the group consisting of optionally substituted heterocycle; O; S; C(O); and NH;

$BS^1$, $BS^2$, $BS^3$ are independently selected from the group consisting of N; and CH;

$S^{0B}$, $S^{1A}$ are independently an alkylene chain having from 1 to 200 carbon atoms, which is optionally interrupted or terminated by one or more groups, cycles or heteroatoms selected from the group consisting of optionally substituted heterocycle; O; S; C(O); and NH;

$S^{0C}$, $S^{1B}$ are $(C(O))_{n2}(CH_2)_{n1}(OCH_2CH_2)_nOCH_3$, wherein each n is independently an integer from 100 to 500, each n1 is independently 0, 1, 2, 3, 4, 5, 6, 7, or 8, and n2 is 0 or 1; and $S^2$, $S^3$ are independently hydrogen; or $(C(O))_{n2}(CH_2)_{n1}(OCH_2CH_2)_nOCH_3$, wherein each n is independently an integer from 100 to 500, each n1 is independently 0, 1, 2, 3, 4, 5, 6, 7, or 8, and n2 is 0 or 1, provided that at least one of $S^2$, $S^3$ is other than hydrogen.

17. The method of claim 1, wherein the GH related disease is selected from the group consisting of growth hormone deficiency ("GHD"), adult onset growth hormone deficiency, Turner syndrome, Prader-Willi syndrome, short bowel syndrome, chronic renal insufficiency, small for gestational age ("SGA"), AIDS wasting, anti-ageing, rheumatoid arthritis, idiopathic small stature, short stature homeobox gene, somatopause, Noonan syndrome, skeletal dysplasia, Down syndrome, short stature associated with prolonged steroid use, Aarskog's syndrome, chronic renal disease, juvenile rheumatoid arthritis; cystic fibrosis, HIV-infection in children receiving HAART treatment; short stature in children born with very low birth weight but SGA; skeletal dysplasia; hypochondroplasia; achondroplasia; idiopathic short stature; GHD in adults; fractures in or of long bones, such as tibia, fibula, femur, humerus, radius, ulna, clavicula, metacarpea, metatarsea, and digit; fractures in or of spongious bones, such as the scull, base of hand, and base of food; patients after tendon or ligament surgery in hand, knee, or shoulder; distraction osteogenesis; disorders resulting from hip or discus replacement, meniscus repair, spinal fusions or prosthesis fixation; disorders resulting from fixing of osteosynthesis material; non-union or mal-union of fractures; disorders resulting from osteotomia; disorders resulting from graft implantation; articular cartilage degeneration in knee caused by trauma or arthritis; osteoporosis in patients with Turner syndrome; osteoporosis in men; adult patients in chronic dialysis ("APCD"); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome; male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; and short stature due to glucocorticoid treatment in children.

18. The method of claim 1, wherein the GH related disease is growth hormone deficiency.

* * * * *